US012564591B2

(12) United States Patent
Treon et al.

(10) Patent No.: US 12,564,591 B2
(45) Date of Patent: Mar. 3, 2026

(54) HCK AS A THERAPEUTIC TARGET IN MYD88 MUTATED DISEASES

(71) Applicant: Dana-Farber Cancer Institute, Inc., Boston, MA (US)

(72) Inventors: Steven P. Treon, Jamaica Plain, MA (US); Guang Yang, Natick, MA (US); Jinhua Wang, Winchester, MA (US); Li Tan, Shanghai (CN); Nathanael S. Gray, Stanford, CA (US); Sara Jean Buhrlage, Somerville, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 661 days.

(21) Appl. No.: 17/767,408

(22) PCT Filed: Oct. 7, 2020

(86) PCT No.: PCT/US2020/054541
§ 371 (c)(1),
(2) Date: Apr. 7, 2022

(87) PCT Pub. No.: WO2021/071922
PCT Pub. Date: Apr. 15, 2021

(65) Prior Publication Data

US 2022/0395509 A1 Dec. 15, 2022

Related U.S. Application Data

(60) Provisional application No. 62/912,474, filed on Oct. 8, 2019.

(51) Int. Cl.

| | |
|---|---|
| ***A61K 31/635*** | (2006.01) |
| ***A61K 31/519*** | (2006.01) |
| ***A61K 45/06*** | (2006.01) |
| ***A61P 35/00*** | (2006.01) |
| ***A61P 35/02*** | (2006.01) |
| ***C07D 487/04*** | (2006.01) |

(52) U.S. Cl.
CPC ............ *A61K 31/519* (2013.01); *A61K 45/06* (2013.01); *A61P 35/00* (2018.01); *A61P 35/02* (2018.01); *C07D 487/04* (2013.01)

(58) Field of Classification Search
None
See application file for complete search history.

(56) References Cited

U.S. PATENT DOCUMENTS

| | | | |
|---|---|---|---|
| 6,660,744 B1 | 12/2003 | Hirst et al. | |
| 10,525,060 B2 * | 1/2020 | Treon | A61P 35/02 |
| 2002/0156081 A1 | 10/2002 | Hirst et al. | |
| 2004/0137489 A1 | 7/2004 | Shaughnessy | |
| 2007/0281907 A1 | 12/2007 | Watkins | |
| 2009/0156469 A1 | 6/2009 | Ghobrial et al. | |
| 2010/0009350 A1 | 1/2010 | Chow | |
| 2010/0216115 A1 | 8/2010 | Yan et al. | |
| 2012/0065201 A1 | 3/2012 | Honigberg et al. | |

(Continued)

FOREIGN PATENT DOCUMENTS

| | | |
|---|---|---|
| CN | 107056786 B | 5/2019 |
| EP | 2878601 A1 | 6/2015 |

(Continued)

OTHER PUBLICATIONS

Yang et al., Blood (2016) 127 (25): (3237-3252) (Year: 2016).*
Office Action received in corresponding Chinese patent application No. 202080080330.X, dated Jun. 30, 2023.
Office Action received in corresponding Chinese patent application No. 202080080330.X, dated Jan. 16, 2024.
Office Action received in corresponding Chinese patent application No. 202080080330.X, dated Jun. 17, 2024.
Advani et al., Bruton tyrosine kinase inhibitor ibrutinib (PCI-32765) has significant activity in patients with relapsed/refractory B-cell malignancies. J Clin Oncol. Jan. 1, 2013;31(1):88-94. doi:10.1200/JCO.2012.42.7906. Epub Oct. 8, 2012.

(Continued)

*Primary Examiner* — Kortney L. Klinkel
*Assistant Examiner* — Alison Azar Salamatian
(74) *Attorney, Agent, or Firm* — Amy H. Fix; Steven Sturlis; Barnes & Thornburg LLP

(57) ABSTRACT

Provided herein are methods of treating diseases (e.g., proliferative disease (e.g., cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenstrom's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), and leukemia (e.g., chronic lymphocytic leukemia (CLL), acute lymphoblastic leukemia, myelogenous leukemia (e.g., chronic myelogenous leukemia, acute myelogenous leukemia))))) comprising administering to the subject in need thereof a therapeutically effective amount of Compound (I). Further provided are methods for treating disease resistant to treatment with BTK inhibitors (e.g., ibmtinib). Formula (I)

(I)

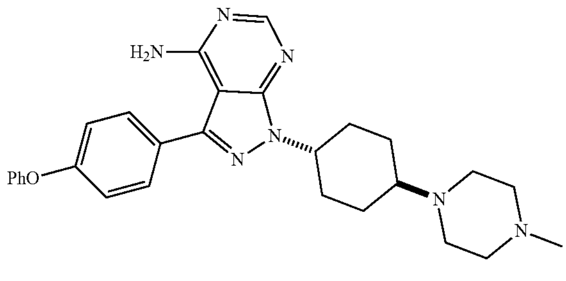

17 Claims, 35 Drawing Sheets

(56) References Cited

U.S. PATENT DOCUMENTS

| | | | |
|---|---|---|---|
| 2012/0071497 A1 | 3/2012 | Buggy et al. | |
| 2014/0249142 A1 | 9/2014 | Treon | |
| 2015/0210698 A1 | 7/2015 | Ishikawa et al. | |
| 2016/0222465 A1 | 8/2016 | Treon et al. | |
| 2016/0304958 A1 | 10/2016 | Treon et al. | |
| 2017/0333436 A1 | 11/2017 | Treon et al. | |
| 2019/0276459 A1 * | 9/2019 | Crews | A61K 47/10 |

FOREIGN PATENT DOCUMENTS

| | | | | |
|---|---|---|---|---|
| EP | 2878601 B1 | 3/2018 | | |
| JP | 2003509428 A | 3/2003 | | |
| JP | 2010/235628 | 10/2010 | | |
| JP | 2019518006 A5 | 6/2019 | | |
| WO | 2001/019829 A2 | 3/2001 | | |
| WO | WO-0119829 A2 * | 3/2001 | | A61P 1/04 |
| WO | 2006/067091 A1 | 6/2006 | | |
| WO | 2008/060367 A2 | 5/2008 | | |
| WO | 2011/095556 A1 | 8/2011 | | |
| WO | 2013/006443 A2 | 1/2013 | | |
| WO | 2013/071068 A2 | 5/2013 | | |
| WO | 2014/017659 | 1/2014 | | |
| WO | 2015/038887 A1 | 3/2015 | | |
| WO | 2017/172826 A1 | 10/2017 | | |
| WO | 2017/189999 A1 | 11/2017 | | |
| WO | 2021/071919 A1 | 4/2021 | | |

OTHER PUBLICATIONS

Anderson et al., Multiple myeloma, version Jan. 2013. J Natl Compr Canc Netw. Jan. 1, 2013;11(1):11-7.

Arcaini et al., Distinctive clinical and histological features of Waldenstrom's macroglobulinemia and splenic marginal zone lymphoma. Clin Lymphoma Myeloma Leuk. Feb. 2011;l 1(1):103-5. doi: 10.3816/CLML.2011.n.020.

Argentou et al., Rapid detection of MYD88-L265P mutation by PCR-RFLP in B-cell lymphoproliferative disorders. Leukemia. Feb. 2014;28(2):447-9. doi: 10.1038/Пeu.2013.294. Epub Oct. 18, 2013.

Argyropoulos et al., Clonal B cells in W aldenstrom's macroglobulinemia exhibit functional features of chronic active B-cell receptor signaling. Leukemia. May 2016;30(5): 1116-25. doi:10.1038/Пeu.2016.8. Epub Feb. 12, 2016.

Balabanian et al., WHIM syndromes with different genetic anomalies are accounted for by impaired CXCR4 desensitization to CXCL12. Blood. Mar. 15, 2005;105(6):2449-57. Epub Nov. 9, 2004.

Bam et al., Role of Bruton's tyrosine kinase in myeloma cell migration and induction of bone disease. Am J Hematol. Jun. 2013;88(6):463-71. doi: 10.1002/ajh.23433. Epub Mar. 28, 2013.

Baxter et al., Acquired mutation of the tyrosine kinase JAK2 in human myeloproliferative disorders. Lancet. Mar. 19-25, 2005;365(9464):1054-61.

Berger et al., Clinicopathologic features of Waldenstrom's macroglobulinemia and marginal zone lymphoma: are they distinct or the same entity? Clin Lymphoma. Mar. 2005;5(4):220-4. Abstract.

Bergsagel et al., Comprehensive identification of somatic mutations in chronic lymphocytic leukemia. Cancer Cell. Jul. 12, 2011;20(1):5-7. doi: 10.1016/j.ccr.2011.06.023.

Bohers et al., Targetable activating mutations are very frequent in GCB and АБС diffuse large B-cell lymphoma. Genes Chromosomes Cancer. Feb. 2014;53(2):144-53. doi:10.1002/gcc.22126. Epub Nov. 5, 2013.

Brikos et al., Mass spectrometric analysis of the endogenous type I interleukin-1 (IL-1) receptor signaling complex formed after IL-1 binding identifies IL-IRAcP, MyD88, and IRAK-4 as the stable components. Mol Cell Proteomics. Sep. 2007;6(9):1551-9. Epub May 15, 2007.

Burchat, A.F., et al., "Pyrazolo[3,4-d]pyrimidines containing an extended 3-substituent as potent inhibitors of LCK—a selectivity insight", Biorganic & Medicinal Chemistry Letters, (Jan. 1, 2002), vol. 12, pp. 1687-1690.

Burger et al., B cell receptor signaling in chronic lymphocytic leukemia. Trends Immunol. Dec. 2013;34(12):592-601. doi: 10.1016/j.it.2013.07.002. Epub Aug. 5, 2013.

Busillo et al., Regulation of CXCR4 signaling. Biochim Biophys Acta. Apr. 2007; 1768( 4 ):952-63. Epub Nov. 10, 2006.

Busillo et al., Site-specific phosphorylation of CXCR4 is dynamically regulated by multiple kinases and results in differential modulation of CXCR4 signaling. J Biol Chem. Mar. 5, 2010;285(10):7805-17. doi: 10.1074/jbc.M109.091173. Epub Jan. 4, 2010.

[No Author Listed] Package Insert. Campath (Alemtuzumab). Millennium and ILEX Partners, LP. Date created Segtember 26, 2003; 1-11.

Cao et al., CXCR4 WHIM-like frameshift and nonsense mutations promote ibrutinib resistance but do not supplant MYD88(L265P)—directed survival signalling in Waldenstrom macroglobulinaemia cells. Br J Haematol. Mar. 2015;168(5):701-7.doi:10.1111/bjh.13200. Epub Nov. 5, 2014.

Cao et al., The WHIM-like CXCR4(S338X) somatic mutation activates AKT and ERK, and promotes resistance to ibrutinib and other agents used in the treatment of Waldenström's Macroglobulinemia. Leukemia. Jan. 2015;29(1):169-76. doi: 10.1038/leu.2014.187. Epub Jun. 10, 2014.

Cao et al., Whole Genome Sequencing Identifies Recurring Somatic Mutations in the C-Terminal Domain of CXCR4, Including a Gain of Function Mutation in Waldenstrom's Macroglobinemia. Blood. 2012;120: Abstract 2715.

Carnevali et al., Computational techniques for human genome resequencing using mated gapped reads. J Comput Biol. Mar. 2012;l9(3):279-92. doi: 10.1089/cmb.2011.0201. Epub101 Dec. 1, 2016.

Chen, Treatment for Waldenstrom's macroglobulinemia. Ann Oncol. Apr. 2014;l5(4):550-8.

Cheng et al., Binding of Bruton's tyrosine kinase to Fyn, Lyn, or Hck through a Src homology 3 domain-mediated interaction. Proc Natl Acad Sci U S A. Aug. 16, 1994;91(17):8152-5.

Chng et al., Gene-expression profiling of W aldenstrom macroglobulinemia reveals a phenotype more similar to chronic lymphocytic leukemia than multiple myeloma. Blood. Oct. 15, 2006;108(8):2755-63. Epub Jun. 27, 2006.

Dasmahaptra et al., The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib. Br J. Haematol. Apr. 2013;161(1):43-56. Abstract only.

Dave et al., Molecular diagnosis of Burkitt's lymphoma. N Engl J Med. Jun. 8, 2006;354(23):2431-42.

Davies et al., Preclinical pharmacology of AZD5363, an inhibitor of AKT: pharmacodynamics, antitumor activity, and conelation of monotherapy activity with genetic background. Mol Cancer Ther. Apr. 2023;l1(4):873-87. doi: 10.1158/1535-7163.MCT-11-0824-T. Epub Jan. 31, 2012.

Ditzel et al., Establishment of BCWM.1 cell line for Waldenstrom's macroglobulinemia with productive in vivo engraftment in SCID-hu mice. Exp Hematol. Sep. 2007;35(9):1366-75.

DottaA et al., Clinical and genetic features of Warts, Hypogammaglobulinemia, Infections and Myelokathexis (WHIM) syndrome. Cun Mol Med. Jun. 2011;l 1(4):317-25.

Drmanac et al., Human genome sequencing using unchained base reads on self-assembling DNA nanoanays. Science. Jan. 1, 2010;327(5961):78-81.

Extended European Search Report for EP12807230.3 mailed Feb. 2, 2015 (D0504.70024EP00).

Extended European Search Report for EP14844516.6 mailed Mar. 28, 2017 (D0504.70048EP00).

Evans et al., Inhibition of Btk with CC-292 provides early pharmacodynamic assessment of activity in mice and humans. J Pharmacol Exp Ther. Aug. 2013;346(2):219-28. doi:10.1124/jpet.113.203489. Egub May 24, 2013.

Farre et al., Identification of patterns in biological sequences at the ALGGEN server: PROMO and MALGEN. Nucleic Acids Res. Jul. 1, 2003;31(13):3651-3.

(56) References Cited

OTHER PUBLICATIONS

Futahashi et al., Separate elements are required for ligand-dependent and -independent internalization of metastatic potentiator CXCR4. Cancer Sci. Mar. 2007;98(3):373-9.
Gachard et al., IGHV gene features and MYD88 L265P mutation separate the three marginal zone lymphoma entities and W aldenstrom macroglobulinemia/lymphoplasmacytic lymphomas. Leukemia. Jan. 2013;27(1):183-9. doi: 10.1038/leu.2012.257. Epub Sep. 4, 2012.
Gay et al., Assembly and localization of Toll-like receptor signalling complexes. Nat Rev Immunol. Aug. 2014;14(8):546-58. doi: 10.1038/nri3713.
Genbank Submission; NIH/NCBI, Accession No. NM_001008540. Micucci et al., Mar. 18, 2016.
Gertz et al., Waldenstrom's macroglobulinemia. Oncologist. 2000;5(1):63-7.
Gopal et al., PI3K8 inhibition by idelalisib in patients with relapsed indolent lymphoma. N Engl J Med. Mar. 13, 2014;370(11):1008-18. doi: 10.1056/NEJMoa1314583. Epub Jan. 22, 2014.
Gutierrez et al., Gene expression profiling of B lymphocytes and plasma cells from Waldenstrom's macroglobulinemia: comparison with expression patterns of the same cell counterparts from chronic lymphocytic leukemia, multiple myeloma and normal individuals. Leukemia. Mar. 2007;21(3):541-9. Epub Jan. 25, 2007.
Hallek et al., Signal transduction of interleukin-6 involves tyrosine phosphorylation of multiple cytosolic proteins and activation of Src-family kinases Fyn, Hck, and Lyn in multiple myeloma cell lines. Exp Hematol. Dec. 1997;25(13): 1367-77.
Hanke et al., Discovery of a novel, potent, and Src family-selective tyrosine kinase inhibitor. Study of Lck- and FynT-dependent T cell activation. J Biol Chem. Jan. 12, 1996;271(2):695-701.
Harris et al., A revised European-American classification of lymphoid neoplasms: a proposal from the International Lymphoma Study Group. Blood. Sep. 1, 1994;84(5):1361-92.
Herman et al., Bruton tyrosine kinase represents a promising therapeutic target for treatment of chronic lymphocytic leukemia and is effectively targeted by PCI-32765. Blood. Jun. 9, 2011;117(23):6287-96. doi: 10.1182/blood-2011-01-328484. Epub Mar. 21, 2011.
Hodge et al., IL-21 in the bone marrow microenvironment contributes to IgM secretion and proliferation of malignant cells in Waldenstrom macroglobulinemia. Blood. Nov. 1, 2012;120(18):3774-82. doi: 10.1182/blood-2012-03-419440. Epub Sep. 13, 2012.
Hong et al., The Src family kinase Hck regulates mast cell activation by suppressing an inhibitory Src family kinase Lyn. Blood. Oct. 1, 2007;110(7):2511-9. Epub May 19, 2007. Enatum in: Blood. Mar. 15, 2008;111(6):3299.
Honinberg et al., The Bruton tyrosine kinase inhibitor PCI-32765 blocks B-cell activation and is efficacious in models of autoimmune disease and B-cell malignancy. Proc Natl Acad Sci U S A Jul. 20, 2010;107(29):13075-80. doi:10.1073/pnas.1004594107. Epub Jul. 6, 2010.
Hunter et al., Recuning activation mutations and somatic deletions revealed through whole genome sequencing in Waldenstrom's Macroglobulinemia. Hematol Oncol. Jun. 2013;31(Sl): Abstract 093.
Hunter et al., The genomic landscape of Waldenstrom macroglobulinemia is characterized by highly recuning MYD88 and WHIM-like CXCR4 mutations, and small somatic deletions associated with B-cell lymphomagenesis. Blood. Mar. 13, 2014; 123(11 ): 1637-46. doi:10.1182/blood-2013-09-525808. Epub Dec. 23, 2013.
Hunter et al., Use of whole genome sequencing to identify highly recunent somatic mutations in Waldenstrom's macroglobulinemia. 2012 ASCO Annual Meeting. Jun. 1-Jun. 5. Chicago, Illinois: Abstract 8107.
Invitation to Pay Additional Fees for PCT/US2012/044956 mailed Oct. 1, 2012 (D0504.70024WO00).
International Preliminary Report on Patentability for PCT/US2012/044956 mailed Jan. 16, 2014 (D0504.70024WO00).
International Preliminary Report on Patentability for PCT/US2014/055386 mailed Mar. 24, 2016 (D0504.70048WO00).
International Preliminary Report on Patentability for PCT/US2014/068579 mailed Jun. 16, 2016 (D0504.70054WO00).
International Report on Patentability for Application No. PCT/US2017/030116 mailed Nov. 8, 2018 (D0504.70116WO00).
International Preliminary Report on Patentability for Application No. PCT/US2020/054538 dated Apr. 12, 2022.
International Preliminary Report on Patentability for Application No. PCT/US2020/054541 dated Apr. 12, 2022.
International Search Report and Written Opinion for PCT/US2012/044956 mailed Dec. 17, 2012 (D0504.70024WO00).
International Search Report and Written Opinion for PCT/US2014/055386 mailed Dec. 23, 2014 (D0504.70048WO00).
International Search Report and Written Opinion for PCT/US2014/068579 mailed Mar. 3, 2015 (D0504.70054WO00).
International Search Report and Written Opinion for PCT/US2017/030116 mailed Aug. 21, 2017 (D0504.70116WO00).
International Search Report and Written Opinion for PCT/US2020/054538 dated Mar. 30, 2021.
International Search Report and Written Opinion for PCT/US2020/054541 dated Feb. 17, 2021.
Janz, Waldenstrom macroglobulinemia: clinical and immunological aspects, natural history, cell of origin, and emerging mouse models. ISRN Hematol. Sep. 9, 2013;2013:815325. doi: 10.1155/2013/815325.
Jeelall et al., Oncogenic MYD88 mutation drives Toll pathway to lymphoma. Immunol Cell Biol. Aug. 2011;89(6):659-60. doi: 10.1038/icb.2011.31. Epub Apr. 26, 2011.
Jimenez et al., MYD88 L265P is a marker highly characteristic of, but not restricted to, Waldenstrom's macroglobulinemia. Leukemia. Aug. 2013;27(8): 1722-8. doi: 10.1038/Пeu.2013.62. Epub Feb. 28, 2013.
Jourdan et al., Characterization of a transitional preplasmablast population in the process of human B cell to plasma cell differentiation. J Immunol. Oct. 15, 2011;187(8):3931-41. doi:10.4049/jimmunol.1101230. Epub Sep. 14, 2011.
Juilland et al., CARMAI- and MyD88-dependent activation of Jun/ATF-type AP-1 complexes is a hallmark of АБС diffuse large B-cell lymphomas. Blood. Apr. 7, 2016;127(14):1780-9. doi:10.1182/blood-2015-07-655647. Epub Jan. 8, 2016.
Kawagoe et al., Sequential control of Toll-like receptor-dependent responses by IRAKI and IRAK2. Nat Immunol. Jun. 2008;9(6):684-91.
Ke, J., et al., "Anomalous constitutive Src kinase activity promotes B lymphoma survival and growth", Molecular Cancer, (Dec. 31, 2009), vol. 8, No. 1, p. 132.
Kiss et al., Comparative testing of peripheral blood and bone manow for BCR-ABL transcripts in patients post allogeneic bone manow transplantation and during interferon treatment for chronic myeloid leukemia. Leuk Lymphoma. Aug. 1999;34(5-6):493-500.
Kriangkum et al., Clonotypic IgM V/D/J sequence analysis in Waldenstrom macroglobulinemia suggests an unusual B-cell origin and an expansion of polyclonal B cells in peripheral blood. Blood. Oct. 1, 2004;104(7):2134-42. Epub Feb. 5, 2004.
Kyle et al., IgM monoclonal gammopathy of undetermined significance and smoldering Waldenstrom's macroglobulinemia. Clin Lymphoma Myeloma. Mar. 2009;9(1):1 7-8.
Kyle et al., Prognostic markers and criteria to initiate therapy in W aldenstrom's macroglobulinemia: consensus panel recommendations from the Second International W orkshop on W aldenstrom's Macroglobulinemia. Semin Oncol. Apr. 2003;30(2): 116-20.
Kyrtsonis et al., CD138 expression helps distinguishing Waldenstrom's macroglobulinemia (WM) from splenic marginal zone lymphoma (SMZL). Clin Lymphoma Myeloma Leuk. Feb. 2011;1 1(1):99-102. doi: 10.3816/CLML.2011.n.Q19.
Lagane et al., CXCR4 dimerization and beta-anestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.
Lam et al., Cooperative signaling through the signal transducer and activator of transcription 3 and nuclear factor-{kappa}B pathways in subtypes of diffuse large B-cell lymphoma. Blood. Apr. 1, 2008;111(7):3701-13. Epub Dec. 26, 2007.

(56) References Cited

OTHER PUBLICATIONS

Landgren et al., MYD88 L265P somatic mutation in IgM MGUS. N Engl J Med. Dec. 6, 2012;367(23):2255-6; author reply 2256-7. doi: 10.1056/NEJMc1211959#SA1.
Lee et al., The mutation spectrum revealed by paired genome sequences from a lung cancer patient. Nature. May 27, 2010;465(7297):473-7.
Leleu et al., Targeting NF-kappaB in Waldenstrom macroglobulinemia. Blood. May 15, 2008; 111(10):5068-77.
Leleu et al., The Akt pathway regulates survival and homing in Waldenstrom macroglobulinemia. Blood. Dec. 15, 2007;110(13):4417-26. Epub Aug. 30, 2007.
Lin et al., Helical assembly in the MyD88-IRAK4-IRAK2 complex in TLR/IL-IR signaling. Nature. Jun. 17, 2010;465(7300):885-90.
Lin et al., Lymphoid neoplasms associated with IgM paraprotein: a study of 382 patients. Am J Clin Pathol. Feb. 2005;123(2):200-5.
Loiarro et al., Identification of critical residues of the MyD88 death domain involved in the recruitment of downstream kinases. J Biol Chem. Oct. 9, 2009;284(41):28093-103.
Loiarro et al., Peptide-mediated interference of TIR domain dimerization in MyD88 inhibits interleukin-1-dependent activation of NF-{kappa}B. J Biol Chem. Apr. 22, 2005;280(16):15809-14. Epub Mar. 8, 2005.
Loiarro et al., Pivotal Advance: Inhibition of MyD88 dimerization and recruitment of IRAKI and IRAK4 by a novel peptidomimetic compound. J Leukoc Biol. Oct. 2007;82(4):801-10. Epub Jun. 4, 2007.
Martinez et al., Whole-exome sequencing in splenic marginal zone lymphoma reveals mutations in genes involved in marginal zone differentiation. Leukemia. Jun. 2014;28(6):1334-40. doi: 10.1038/leu.2013.365. Epub Dec. 3, 2013.
Mcdermott et al., A phase 1 clinical trial of long-term, low-dose treatment of WHIM syndrome with the CXCR4 antagonist plerixafor. Blood. Apr. 10, 2014;123(15):2308-16. doi: 10.1182/blood-2013-09-527226. Epub Feb. 12, 2014.
Mcdermott et al., AMD3100 is a potent antagonist at CXCR4(R334X) , a hyperfunctional mutant chemokine receptor and cause of WHIM syndrome. J Cell Mol Med. Oct. 2011; 15(10);2071-81. doi: 10.1111/j.1582-4934.2010.Q1210.x.
Mcdermott et al., The CXCR4 antagonist plerixafor conects panleukopenia in patients with WHIM syndrome. Blood. Nov. 3, 2011;118(18):4957-62. doi: 10.1182/blood-2011-07-368084. Epub Sep. 2, 2011.
Mcmaster et al., Long-term evaluation of three multiple-case Waldenstrom macroglobulinemia families. Clin Cancer Res. Sep. 1, 2007; 13(17):5063-9.
Messeguer et al., PROMO: detection of known transcription regulatory elements using species-tailored searches. Bioinformatics. Feb. 2002;l8(2):333-4.
Montesinos-Rongen et al., Activating L265P mutations of the MYD88 gene are common in primary central nervous system lymphoma. Acta Neuropathol. Dec. 2011;122(6):791-2. doi:10.1007/s00401-01 1-0891-2. Epub Oct. 22, 2011.
Mueller et al., Hierarchical organization of multi-site phosphorylation at the CXCR4 C terminus. PLoS One. May 29, 2013;8(5):e64975. doi: 10.1371/journal.pone.0064975. Print 2013.
Musumeci et al., Hck inhibitors as potential therapeutic agents in cancer and HIV infection. Cun Med Chem. 2015;22(13):1540-64
Ngo et al., Oncogenically active MYD88 mutations in human lymphoma. Nature. Feb. 3, 2011;470(7332):115-9. doi: 10.1038/nature09671.
Ngo et al., SDF-1/CXCR4 and VLA-4 interaction regulates homing in Waldenstrom macroglobulinemia. Blood. Jul. 1, 2008;112(1):150-8. doi: 10.1182/blood-2007-12-129395. Epub Apr. 30, 2008.
Ngo et al., Src tyrosine kinase regulates adhesion and chemotaxis in Waldenstrom macroglobulinemia. Clin Cancer Res. Oct. 1, 2009;15(19):6035-41. doi: 10.1158/1078-0432.CCR-09-0718. Epub Sep. 15, 2009.
O'Boyle et al., Open Babel: An open chemical toolbox. J Cheminform. Oct. 7, 2011;3:33. doi: 10.1186/1758-2946-3-33.
Okada et al., Autopsy case of lymphoplasmacytic lymphoma with a large submucosal tumor in the stomach. Pathol Int. Oct. 2001;51(10):802-6.
Okuzumi et al., Inhibitor hijacking of Akt activation. Nat Chem Biol. Jul. 2009;5(7):484-93. doi:10.1038/nchembio.183. Epub May 24, 2009.
Ondrejka et al., MYD88 L265P somatic mutation: its usefulness in the differential diagnosis of bone manow involvement by B-cell lymphoproliferative disorders. Am J Clin Pathol. Sep. 2013;140(3):387-94. doi: 10.1309/AJCPIOZCLFZGYZIP.
Owen et al., Clinicopathological definition of Waldenstrom's macroglobulinemia: consensus panel recommendations from the Second International Workshop on Waldenstrom's Macroglobulinemia. Semin Oncol. Apr. 2003;30(2): 110-5.
Passamonti, How I treat polycythemia vera. Blood. Jul. 12, 2012;120(2):275-84. doi: 10.1182/blood-2012-02-366054. Epub May 18, 2012.
Patricelli et al., In situ kinase profiling reveals functionally relevant properties of nati ve kinases. Chem Biol. Jun. 24, 2011;18(6):699-710. doi:10.1016/j.chembiol.2011.04.011.
Pecquet et al., The Src tyrosine kinase Hck is required for Tel-Abl—but not for Tel-Jak2-induced cell transformation. Oncogene. Mar. 8, 2007;26(11):1577-85. Epub Sep. 4, 2006.
Pene-Dumitrescu et al., An inhibitor-resistant mutant of Hck protects CML cells against the antiproliferative and apoptotic effects of the broad-spectrum Src family kinase inhibitor A-419259. Oncogene. Nov. 27, 2008;27(56):7055-69. doi:10.1038/onc.2008.330. Epub Sep. 15, 2008.
Poh et al., Hematopoietic cell kinase (HCK) as a therapeutic target in immune and cancer cells. Oncotarget. Jun. 30, 2015;6(18):15752-71.
Poulain et al., MYD88 L265P mutation in Waldenstrom macroglobulinemia. Blood. May 30, 2013;121(22):4504-11. doi: 10.1182/blood-2012-06-436329. Epub Mar. 26, 2013.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Puente et al., Whole-genome sequencing identifies recurrent mutations in chronic lymphocytic leukaemia. Nature. Jun. 5, 2011;475(7354):101-5. doi:10.1038/naturel0l 13.
Roach et al., Analysis of genetic inheritance in a family quartet by whole-genome sequencing. Science. Apr. 30, 2010;328(5978):636-9.
Roccaro et al., A Novel Activating Mutation Of CXCR4 Plays a Crucial Role In Waldenstrom Macroglobulinemia Biology. Blood. 2013;122: Abstract 272.
Roccaro et al., C1013G/CXCR4 acts as a driver mutation of tumor progression and modulator of drug resistance in lymphoplasmacytic lymphoma. Blood. Jun. 26, 2014;123(26):4120-31. doi:10.1182/blood-2014-03-564583. Epub Apr. 7, 2014.
Sahota et al., CD27 in defining memory B-cell origins in W aldenstrom's macroglobulinemia. Clin Lymphoma Myeloma. Mar. 2009;9(1):33-5. doi: 10.3816/CLM.2009.n.007.
Saijo et al., Essential role of SrC-family protein tyrosine kinases in NF-kappaB activation during B cell development. Nat Immunol. Mar. 2003;4(3):274-9. Epub Feb. 3, 2003.
Saito et al., A pynolo-pyrimidine derivative targets human primary AML stem cells in vivo. Sci Transl Med. Apr. 17, 2013;5(181):181ra52. doi: 10.1126/scitranslmed.3004387.
Sanner et al., Reduced surface: an efficient way to compute molecular surfaces. Biopolymers. Mar. 1996;38(3):305-20.
Schaeffer et al., Signaling through a novel domain of gp130 mediates cell proliferation and activation of Hck and Erk kinases. Mol Cell Biol. Dec. 2001;21(23):8068-81.
Smith et al., In Waldenstrom's macroglobulinemia the quantity of detectable circulating monoclonal B lymphocytes conelates with clinical course. Blood. May 1983;61(5):911-4.
Song et al., The kinase activities of interleukin-1 receptor associated kinase (IRAK)-1 and 4 are redundant in the control of inflammatory cytokine expression in human cells. Mol Immunol. Apr. 2009;46(7): 1458-66.
Suh et al., Inhibition of granulocyte-macrophage colony-stimulating factor signaling and microglial proliferation by anti-CD45RO: role

(56) References Cited

OTHER PUBLICATIONS of Hck tyrosine kinase and ghosghatidxlinositol 3-kinase/Akt. J Immunol. Mar. 1, 2005;174(5):2712-9.
Taguchi et al., Characteristic expression of Hck in human B-cell precursors. Exp Hematol. Jan. 2000;28(1):55-64. Enatum in: Exp Hematol. Mar. 2000;28(3):347.
Tai et al., Bruton tyrosine kinase inhibition is a novel therapeutic strategy targeting tumor in the bone manow microenvironment in multiple myeloma. Blood. Aug. 30, 2012;120(9):1877-87. doi: 10.1182/blood-2011-12-396853. Epub Jun. 11, 2012.
Tai et al., Targeting Brouton's Tyrosine Kinase with PCI-32765 Blocks Growth and Survival of Multiple Myeloma and Waldenstrom Macroglobulinemia Via Potent Inhibition of Osteoclastogenesis, Cytokines/Chemokine Secretion, and Myeloma Stem-Like Cells in the Bone Manow Microenvironment. Blood. Nov. 18, 2011;118(21):404.
Tesar et al., MYD88 L265P Mutations Influence Clinical Outcome and Identify a Pathway for Targeted Inhibition in Chronic Lymphocytic Leukemia. Presentation. American Society of Hematology Conference. Dec. 7, 2015. Abstract only.
[No Author Listed] Trademark Electronic Search System (TESS) Typed Drawing. May 21, 1991. 2nd Renewal Apr. 24, 2013. Last accessed Apr. 4, 2018.
Tiacci et al., Simple genetic diagnosis of hairy cell leukemia by sensitive detection of the BRAF-V600E mutation. Blood. Jan. 5, 2012;119(1):192-5. doi: 10.1182/blood-2011-08-371179. Epub Oct. 25, 2011. Enatum in: Blood. Aug. 29, 2013;122(9):1685.
Treon et al., A new era for Waldenstrom macroglobulinemia: MYD88 L265P. Blood. May 30, 2013;121(22):4434-6. doi: 10.1182/blood-2013-04-494849.
Treon et al., A Prospective Multicenter Study Of The Bruton's Tyrosine Kinase Inhibitor Ibrutinib In Patients With Relapsed Or Refractory Waldenstrom's Macroglobulinemia. Blood. 2013;122:Abstract 251.
Treon et al., A prospective, multicenter, phase II study of the Bruton's Tyrosine Kinase Inhibitor Ibrutihib in patients with relapsed and refractory Waldehstrom's Macroglobulihemia. Hematol Oncol. Jun. 2013;3l(Sl): Abstract 067.
Treon et al., Characterization of familial Waldenstrom's macroglobulinemia. Ann Oncol. Mar. 2006;l 7(3):488-94. Epub Dec. 15, 2005.
Treon et al., Ibrutinib in previously treated Waldenstrom's macroglobulinemia. N Engl J Med. Apr. 9, 2015;372(15):1430-40. doi:10.1056/NEJMoa1501548.
Treon et al., Multicenter clinical trial of bortezomib in relapsed/ refractory Waldenstrom's macroglobulinemia: results of WMCTG Trial 03-248. Clin Cancer Res. Jun. 1, 2007;13(11):3320-5.
Treon et al., MYD88 L265P somatic mutation in Waldenstrom's macroglobulinemia. N Engl J Med. Aug. 30, 2012;367(9):826-33. doi:10.1056/NEJMoa1200710.
Treon et al., MYD88 Mutations and Response to Ibrutinib in Waldenstrom's Macroglobulinemia. N Engl J Med. Aug. 6, 2015;373(6):584-6. doi:10.1056/NEJMC1506192.
Treon et al., Prospective phase II clinical trial of carfilzomib, rituximab, and dexamethasone (CaRD) in Waldenstrom's macroglobulinemia. 12th International Conference on Malignant Lymphoma. Palazzo dei Congressi, Lugano, Switzerland, Jun. 19-22, 2013, abstract 150, 2013.
Treon et al., Prospective, Multicenter Study of the MTOR Inhibitor Everolimus (RADOOI) As Primary Therapy in Waldehstrom's Macroglobulihemia. Blood. 2011;118:Abstract2951.
Treon et al., Somatic mutations in MYD88 and CXCR4 are determinants of clinical presentation and overall survival in Waldenstrom macroglobulinemia. Blood. May 1, 2014;123(18):2791-6. doi:10. 1182/blood-2014-01-550905. Epub Feb. 19, 2014.
Treon et al., Whole Genome sequencing reveals a widely expressed mutation (MYD88 L265P) in Waldenstrom's Macroglobulinemia. Oral and Poster Abstracts. Dec. 2011. 1 Page.
Treon, How I treat Waldenstrom macroglobulinemia. Blood. Sep. 17, 2009;114(12):2375-85.
Trøen et al., CD798 and MYD88 Mutations in Splenic Marginal Zone Lymphoma. ISRN Oncol. 2013;2013:252318. doi: 10.1155/ 2013/252318. Epub Jan. 10, 2013.
Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334.
Varettoni et al., Prevalence and clinical significance of the MYD88 (L265P) somatic mutation in Waldenstrom's macroglobulinemia and related lymphoid neoplasms. Blood. Mar. 28, 2013;121(13):2522-8. doi: 10.1182/blood-2012-09-457101. Epub Jan. 25, 2013.
Wang et al., CD19: a biomarker for B cell development, lymphoma diagnosis and theragx. Experimental Hematol Oncol. 2012;1(36):1-7.
Wang et al., IRAK-4 inhibitors for inflammation. Cun Top Med Chem. 2009;9(8):724-37.
Watters et al., Structure, function and regulation of the Toll/IL-1 receptor adaptor proteins. Immunol Cell Biol. Aug.-Sep. 2007;85(6):41 I-9. Epub Jul. 31, 2007.
Willenbacher et al., Improved accuracy of discrimination between IgM multiple myeloma and Waldenstrom macroglobulinaemia by testing for MYD88 L265P mutations. Br J Haematol. Jun. 2013;161(6):902-4. doi:10.1111/bjh.12313. Epub Apr. 5, 2013.
Wilson et al., Targeting B cell receptor signaling with ibrutinib in diffuse large B cell lymphoma. Nat Med. Aug. 2015;21(8):922-6. doi: 10.1038/nm.3884. Epub Jul. 20, 2015.
Woyach et al., Resistance mechanisms for the Bruton's tyrosine kinase inhibitor ibrutinib. N Engl J Med. Jun. 12, 2014;370(24):2286-94. doi: 10.1056/NEJMoa1400029. Epub May 28, 2014.
Xu et al., Detection Of MYD88 L265P In Peripheral Blood Of Patients With Waldenstrom's Macroglobulinemia and IgM Monoclonal Gammopathy Of Undetermined Significance. Blood. 2013;122(21): Abstract 3024.
Xu et al., Detection of MYD88 L265P in peripheral blood of patients with Waldenstrom's Macroglobulinemia and IgM monoclonal gammopathy of undetermined significance. Leukemia. Aug. 2014;28(8):1698-704. doi: 10.1038/leu.2014.65. Epub Feb. 10, 2014.
Xu et al., MYD88 L265P in Waldenstrom macroglobulinemia, immunoglobulin M monoclonal gammopathy, and other B-cell lymphoproliferative disorders using conventional and quantitative allele-specific polymerase chain reaction. Blood. Mar. 14, 2013; 121 (11 ):2051-8.doi:10.1182/blood-2012-09-454355. Epub Jan. 15, 2013. Erratum in: Blood. Jun. 27, 2013;121(26):5259.
Xu et al., Detection of the MYD88 L265P mutation in Waldenstrom's macroglobulinemia using a highly sensitive allele-specific PCR assay. J Clinical Oncology. May 2012;30(15):8042. Abstract.
Yang et al., HCK Is a Highly Relevant Target of Ibrutinib in MYD88 Mutated Waldenstrom's Macroglobulinemia and Diffuse Large B-Cell Lymphoma. Blood. 2015;126:705.
Yang et al., A mutation in MYD88 (L265P) supports the survival of lymphoplasmacytic cells by activation of Bruton tyrosine kinase in W aldenstrom macroglobulinemia. Blood. Aug. 15, 2013;122(7):1222-32. doi:10.1182/blood-2012-12-475111. Epub Jul. 8, 2013.
Yang et al., HCK is a survival determinant transactivated by mutated MYD88, and a direct target of ibrutinib. Blood. Jun. 23, 2016;127(25):3237-52. doi:10.1182/blood-2016-01-695098. Epub May 3, 2016.
Yang et al., Tyrosine kinase inhibition in diffuse large B-cell lymphoma: molecular basis for antitumor activity and drug resistance of dasatinib. Leukemia. Sep. 2008;22(9): 1755-66. doi:10. 1038/leu.2008.163. Epub Jul. 3, 2008.
Ye et al., t(1; 14) and t(11; 18) in the differential diagnosis of Waldenstrom's macroglobulinemia. Mod Pathol. Sep. 2004;17(9):1150-4.
Young et al., Survival of human lymphoma cells requires B-cell receptor engagement by self-antigens. Proc Natl Acad Sci U S A Nov. 3, 2015;112(44):13447-54. doi:10.1073/pnas.1514944112. Epub Oct. 19, 2015.
MYD88 L265P mutations identify a prognostic gene expression signature and a pathway for targeted inhibition in CLL, British Journal of Haematology, 2018, 184, pp. 925-936.

* cited by examiner

Compound (I)
468 Assays tested
28 interactions mapped
S-Score(1) = 0.07
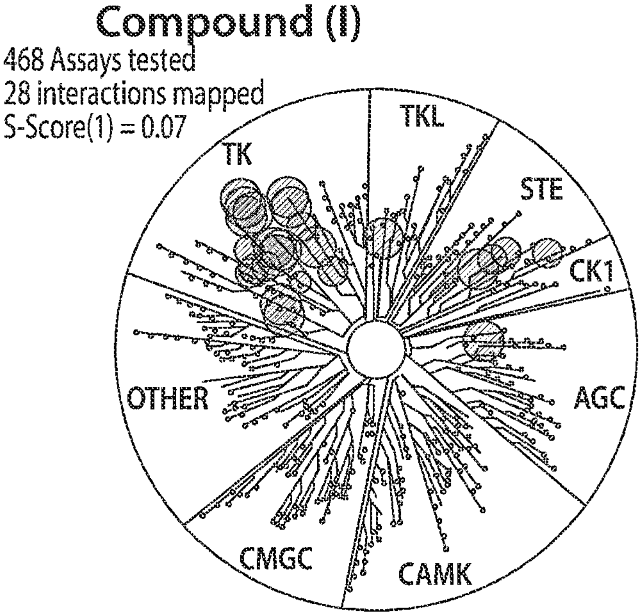
Biochemical assay (Invitrogen)
| Kinases | Enzymatic IC50 (nM) |
|---|---|
| HCK | <0.495 |
| BTK | 0.915 |
| LYN | 1.150 |
Potent HCK, BTK, LYN Suppression
A419259
468 Assays tested
19 interactions mapped
S-Score(1) = 0.05
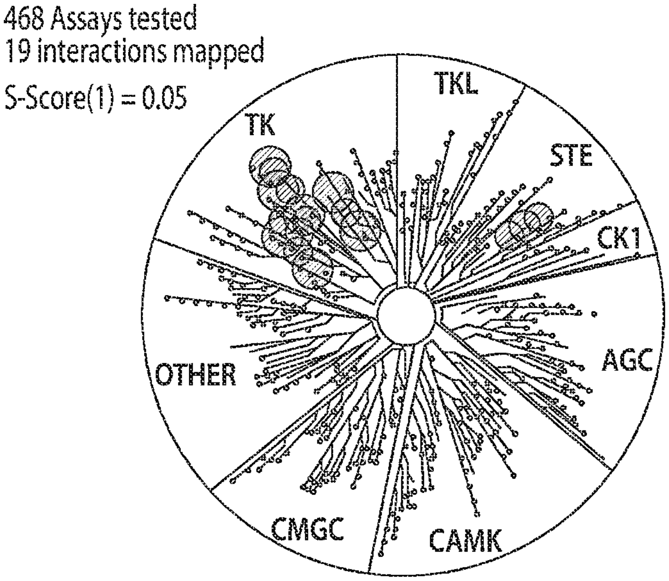
Biochemical assay (Invitrogen)
| Kinases | Enzymatic IC50 (nM) |
|---|---|
| HCK | 0.683 |
| BTK | 7.97 |
| LYN | 1.01 |
Potent HCK, LYN Suppression
Figure 2A Compound (I)

244 Kinases Tested

| Kinases | Enzymatic IC50 (nM) | Kinase group | Kinase family |
|---|---|---|---|
| HCK | <0.495 | TK | SRC |
| BLK | <0.495 | TK | SRC |
| BTK | 0.915 | TK | TEC |
| LYN | 1.150 | TK | SRC |
| FRK | 1.400 | TK | SRC |
| ACK (TNK2) | 7.780 | TK | ACK |
| CSK | 16.100 | TK | CSK |
| ErbB2 | 52.600 | TK | EPH |
| ABL | 98.600 | TK | ABL |

Microsome stability

| Species | $t_{1/2}$ (min) |
|---|---|
| Mouse | 106.4 |
| Rat | >120 |
| Human | 49.5 |

Plasma protein binding

| Species | % |
|---|---|
| Mouse | 97.7 |
| Rat | 95.5 |
| Dog | 95.0 |
| Human | 95.7 |

PK parameters

$t_{1/2}$ = 11.5 h
Cl = 17.4 mL/min/kg
Vss = 14.8 L/kg
$t_{1/2}$ = 15.1 h
AUC = 5.2 μM•h
F= 55%
$t_{1/2}$ = 16.9 h
AUC = 11.4 μM•h
F= 49%

Mouse pharmacokinetics i.v.: 2 mg/kg, 0.2 mg/mL Compound (I) • 3 HCl in Saline
i.v.: 10 mg/kg, 1 mg/mL Compound (I) • 3 HCl in Saline
i.v.: 25 mg/kg, 2.5 mg/mL Compound (I) • 3 HCl in Saline

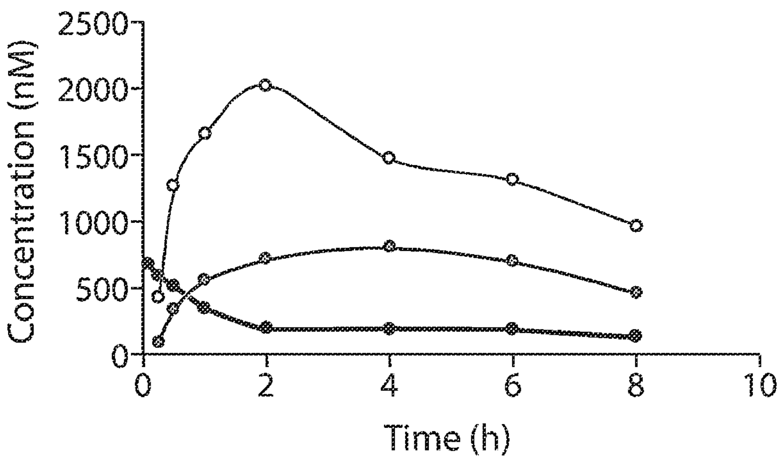

Oral Bioavailability ~ 50%. $T_{1/2}$~ 15 hrs

Figure 8

Microsome stability

| Species | $t_{1/2}$ (min) |
|---|---|
| Mouse | 76.8 |
| Rat | 69.9 |
| Human | 33.6 |

Plasma protein binding

| Species | % |
|---|---|
| Mouse | 99.98 |
| Rat | pending |
| Human | 99.98 |

PK parameters

$t_{1/2}$ = 5.7 h
Cl = 10.78 mL/min/kg
Vss = 4.9 L/kg
$t_{1/2}$ = 176.0 h
AUC = 13.0 μM•h
F= 65.5 %

Mouse pharmacokinetics i.v.: 2 mg/kg, 0.2 mg/mL A419259•3HCl in saline
p.o..: 10mg/kg, 1 mg/mL A419259•3HCl in saline

| | Vehicle | Ibrutinib 50mg/kg | A419259 50mg/kg | Compound (I) 50mg/kg |
|---|---|---|---|---|
| Median Survival (days) | 31 | 90 | 94.5 | Undefined |

Log-rank (Mantel-Cox) test, P<0.0001

| Median Survival | Vehicle | Ibrutinib 50mg/kg | Compound (I) 50mg/kg | Compound (I) 75mg/kg |
|---|---|---|---|---|
| (days) | 29 | 25 | 57.5 | 70.5 |

Log-rank (Mantel-Cox) test, P=0.0007

| | Vehicle | Ibrutinib 50mg/kg | Compound (I) 50mg/kg | A419259 50mg/kg |
|---|---|---|---|---|
| Median Survival (days) | 43 | 33 | 61 | 55 |

| Median Survival | Vehicle | Venetoclax (50mg/kg) | Compound (I) (30mg/kg) | Compound (I) (30mg/kg) + Venetoclax (50mg/kg) |
|---|---|---|---|---|
| (days) | 22 | 27.5 | 36 | 63 |

Log-rank (Mantel-Cox) test, P=0.0020

HCK AS A THERAPEUTIC TARGET IN MYD88 MUTATED DISEASES

RELATED APPLICATIONS

The present application is a national stage filing under 35 U.S.C. § 371 of International PCT Application PCT/US2020/054541, filed Oct. 7, 2020, which claims priority under 35 U.S.C. § 119(e) to U.S. provisional application, U.S. Ser. No. 62/912,474, filed Oct. 8, 2019, each of which is incorporated herein by reference.

BACKGROUND

It has been discovered that Hematopoietic cell kinase (HCK) transcription and activation is triggered by mutated myeloid differentiation primary response 88 (MYD88), and is an important determinant of pro-survival signaling. It has also been discovered that inhibition of the kinase activity of HCK triggers apoptosis in mutated MYD88 cells. For example, the expression of MYD88 mutations in Waldenstram's Macroglobulinemia (WM), wherein 95-97% of patients express $MYD88^{L265P}$, and more rarely non-L265P MYD88 mutations. WM is considered to correspond to lymphoplasmacytic lymphoma (LPL) as defined by the World Health Organization classification system. Up to 30% of patients with Activated B-Cell (ABC) Subtype of Diffuse Large B-cell lymphoma (ABC DLBCL) also express activating MYD88 mutations, including $MYD88^{L265P}$. Mutations in MYD88 promote Myddosome self-assembly and can trigger NF-kB signaling in the absence of Toll (TLR) or IL1 (IL1R) receptor signaling through IL1 Receptor Associated Kinases (IRAK4/IRAK1) or Bruton's Tyrosine Kinase (BTK).

Next generation sequencing has revealed activating myeloid differentiation primary response 88 (MYD88) mutations in several B-cell malignancies including Waldenstrom's macroglobulinemia (immunoglobulin M (IgM) secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia. Particularly striking has been the expression of MYD88 mutations in Waldenstrom's macroglobulinemia (WM), wherein 95-97% of patients express $MYD88^{L265P}$, and more rarely non-L265P MYD88 mutations. Waldenstrom's macroglobulinemia is considered to correspond to lymphoplasmacytic lymphoma (LPL) as defined by the World Health Organization classification system. Up to 30% of patients with Activated B-Cell (ABC) Subtype of Diffuse Large B-cell lymphoma (ABC-DLBCL) also express activating MYD88 mutations, including $MYD88^{L265P}$. Mutations in MYD88 promote Myddosome self-assembly and can trigger NF-kB signaling in the absence of Toll (TLR) or IL1 (IL1R) receptor signaling through IL1 Receptor Associated Kinases (IRAK4/IRAK1) or Bruton's Tyrosine Kinase (BTK).

Ibrutinib (IB) is an inhibitor of BTK that is highly active in WM, resulting in responses in 91% of previously treated patients. In WM patients, both major and overall responses to ibrutinib are higher in patients with MYD88 mutations. ibrutinib also shows activity in previously treated patients with ABC DLBCL, particularly among patients with MYD88 mutations. ibrutinib is also active in other B-cell malignancies including Chronic Lymphocytic Leukemia (CLL) and Mantle Cell Lymphoma (MCL). Suppression of tonic B-cell receptor (BCR) activity mediated by BTK has been implicated as the mechanism underlying ibrutinib activity in non-WM B-cell diseases.

SUMMARY

Provided herein are methods of treating a disease (e.g., a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenstram's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))) in a subject in need thereof, comprising administering to the subject a therapeutically effective amount of Compound (I), of the formula:

(I)

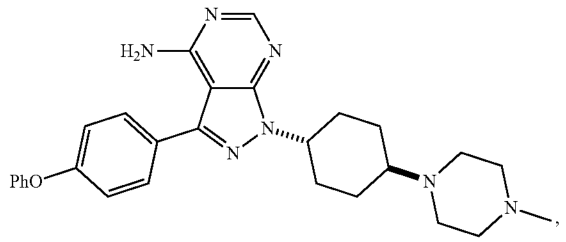

or a pharmaceutically acceptable salt, solvate, hydrate, polymorph, co-crystal, isotopically-labeled derivative, stereoisomer, or prodrug thereof.

Compound (I) may be a kinase inhibitor (e.g., an SRC family kinase (i.e. SFK) (e.g., HCK, LYN, BLK, FRK), a Tec family kinase (e.g., BTK)) and in certain aspects, the compound may be specific or selective for SFKs (e.g., HCK, LYN, BLK, FRK) or Tec family kinases (e.g., BTK) over one or more other kinases. Also provided are pharmaceutical compositions and kits comprising the Compound (I). The present disclosure also provides methods of using the disclosed compound, pharmaceutical compositions, and kits (e.g., for treating a disease (e.g., a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenstram's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))) in a subject in need thereof, or inhibiting the activity of a kinase in a subject in need thereof, a biological sample, or a cell).

In yet another aspect, the present disclosure provides Compound (I), and pharmaceutically acceptable salts, solvates, hydrates, polymorphs, co-crystals, tautomers, stereoisomers, isotopically labeled derivatives, and prodrugs thereof, and pharmaceutical compositions thereof, for use in the treatment and/or prevention of a disease (e.g., a proliferative disease, such as IgM gammopathy, mastocytosis, cancer) in a subject in need thereof.

In another aspect, the present disclosure provides uses of Compound (I), and pharmaceutically acceptable salts, solvates, hydrates, polymorphs, co-crystals, tautomers, stereoisomers, isotopically labeled derivatives, and prodrugs thereof, and pharmaceutical compositions thereof, in the manufacture of a medicament for treating and/or preventing a disease in a subject in need thereof.

In another aspect, the present disclosure provides methods of preparing Compound (I), or a pharmaceutically acceptable salt, solvate, hydrate, polymorph, co-crystal, tautomer, stereoisomer, isotopically labeled derivative, or prodrug thereof.

In one aspect, the present disclosure provides pharmaceutical compositions comprising Compound (I), and optionally a pharmaceutically acceptable excipient. In certain embodiments, the pharmaceutical composition further comprises an additional pharmaceutical agent. In certain embodiments, the additional pharmaceutical agent is selected from the group consisting of chemotherapy drugs, epigenetic modifiers, glucocorticoids, biologics, and immunotherapy agents. In another aspect, the additional pharmaceutical agents is a BCL-2 inhibitor (e.g., venetoclax, navitoclax, obatoclax).

The pharmaceutical compositions may be useful for treating a disease in a subject in need thereof, inhibiting the activity of a kinase in a subject in need thereof, a biological sample, or a cell. In certain aspects, the disease is a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenström's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))).

The present disclosure provides methods of treating a disease in subject by administering to a subject in need thereof an effective amount of Compound (I), or a pharmaceutical composition thereof, as described herein. In certain aspects, the disease is a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenström's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))). Also described are methods for contacting a biological sample or cell with an effective amount of a compound, or pharmaceutical composition thereof, as described herein. In certain embodiments, a method described herein further includes administering to the subject in need thereof an additional pharmaceutical agent. In certain embodiments, a method described herein further includes contacting the biological sample or cell with an additional pharmaceutical agent.

In one aspect, provided are methods for treating a disease in a subject who is resistant to treatment with a BTK inhibitor (e.g., ibrutinib, CC-292, ONO-4059, evobrutinib, spebrutinib, BGB-3111, HM71224, or ACP-196 (i.e., acalabrutinib)). In certain aspects, a subject who is resistant to treatment with a BTK inhibitor has a mutated BTK (e.g., a C481S mutated BTK). In certain aspects, the subject has a C481S mutated BTK. In another aspect, the subject who is resistant to treatment with a BTK inhibitor has a C481S mutated BTK. In another aspect, the subject who is resistant to treatment with a BTK inhibitor is diagnosed with having an MYD88 mutated disease (e.g., a proliferative disease (e.g., an IgM gammopathy, mastocytosis, or cancer)).

In another aspect, provided herein are methods of inhibiting a kinase (e.g., SFK (e.g., HCK, LYN, BLK, FRK), Tec family kinases (e.g., BTK)) in a subject in need thereof, comprising administering to the subject a therapeutically effective amount of Compound (I), or a pharmaceutically acceptable salt, solvate, hydrate, polymorph, co-crystal, isotopically-labeled derivative, stereoisomer, or prodrug thereof. In certain aspects, provided herein are methods for inhibiting a mutated BTK (e.g., a C481S mutant) in a subject in need thereof.

In certain aspects, the method further comprises administering an anti-cancer agent to the subject. In some embodiments, the anti-cancer agent is a chemotherapeutic agent. In another aspect, the method further comprises administering to the subject one or more of a proteasome inhibitor (e.g., bortezomib, carfilzomib, ixazomib or oprozomib), a monoclonal antibody (e.g., rituximab, daratumumab, ofatumumab or obinituzumab), an alkylator drug (e.g., bendamustine, cyclophosphamide), a nucleoside analogue (e.g., fludarabine or cladribine), an mTOR inhibitor (e.g., everolimus), a BTK inhibitor (e.g., ibrutinib, acalabrutinib, or BGB-3111), a BCR inhibitor (e.g., a SYK inhibitor) and/or an immunomodulating agent (e.g., thalidomide or lenalidomide).

In another aspect, the present disclosure provides kits comprising: Compound (I), or a pharmaceutically acceptable salt, solvate, hydrate, polymorph, co-crystal, tautomer, stereoisomer, isotopically labeled derivative, or prodrug thereof, or a pharmaceutical composition thereof; and instructions for using the compound, or a pharmaceutically acceptable salt, solvate, hydrate, polymorph, co-crystal, tautomer, stereoisomer, isotopically labeled derivative, or prodrug thereof, or the pharmaceutical composition.

The details of one or more embodiments of the present disclosure are set forth herein. Other features, objects, and advantages of the present disclosure will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry,* 7th Edition, John Wiley & Sons, Inc., New York, 2013; Richard C. Larock, *Comprehensive Organic Transformations*, John Wiley & Sons, Inc., New York, 2018; and Carruthers, *Some Modern Methods of Organic Synthesis,* 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The present disclosure additionally encompasses compounds described herein as individual isomers substantially free of other isomers, and alternatively, as mixtures of various isomers.

When a range of values ("range") is listed, it encompasses each value and sub-range within the range. A range is inclusive of the values at the two ends of the range unless otherwise provided. For example, "$C_{1-6}$alkyl" encompasses $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

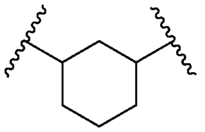 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —C≡C— or —$(CH_2)_4$—). A hydrocarbon chain may also be unsaturated and include one or more C═C and/or C≡C bonds anywhere in the hydrocarbon chain. For instance, —CH═CH—$(CH_2)_2$—, —$CH_2$—C≡C—$CH_2$—, and —C≡C—CH═CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

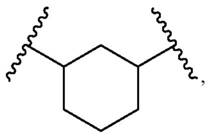, 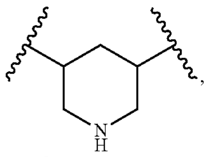, 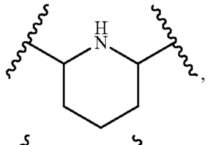, 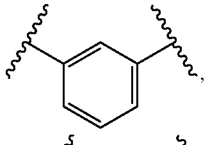, 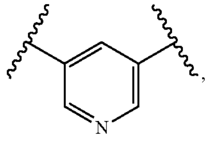, and 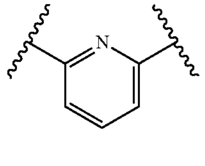

are all examples of a hydrocarbon chain. In contrast, in certain embodiments

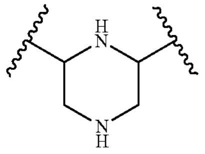 and 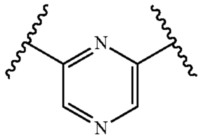

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

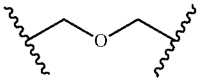 [SMILES: *COC*]

is a $C_3$ hydrocarbon chain wherein one chain atom is replaced with an oxygen atom.

The term "Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $—CH_2F$, $—CHF_2$, $—CF_3$, $—CH_2CH_2F$, $—CH_2CHF_2$, $—CH_2CF_3$, or benzyl (Bn)).

The term "Alkenyl" refers to a radical of a straight-chain or branched hydrocarbon group having from 2 to 20 carbon atoms and one or more carbon-carbon double bonds (e.g., 1, 2, 3, or 4 double bonds. In some embodiments, an alkenyl group has 2 to 20 carbon atoms ("$C_{2-20}$ alkenyl"). In some embodiments, an alkenyl group has 2 to 12 carbon atoms ("$C_{2-12}$ alkenyl"). In some embodiments, an alkenyl group has 2 to 11 carbon atoms ("$C_{2-11}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-3}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 5 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., $—CH=CHCH_3$ or

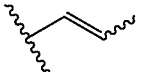

may be in the (E)- or (Z)-configuration.

The term "Alkynyl" refers to a radical of a straight-chain or branched hydrocarbon group having from 2 to 20 carbon atoms, and one or more carbon-carbon triple bonds (e.g., 1, 2, 3, or 4 triple bonds) ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "Carbocyclyl" or "carbocyclic" refers to a radical of a non-aromatic cyclic hydrocarbon group having from 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. In certain embodiments, the carbocyclyl includes 0, 1, or 2 C═C double bonds in the carbocyclic ring system, as valency permits.

The term "Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

The term "Aralkyl" is a subset of "alkyl" and refers to an alkyl group substituted by an aryl group, wherein the point of attachment is on the alkyl moiety. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

The term "Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

The term "Heteroaralkyl" is a subset of "alkyl" and refers to an alkyl group substituted by a heteroaryl group, wherein the attachment is on the alkyl moiety.

The term "unsaturated" or "partially unsaturated" refers to a moiety that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

A group is optionally substituted unless expressly provided otherwise. The term "optionally substituted" refers to being substituted or unsubstituted.

In certain embodiments, alkyl, alkenyl, alkynyl, heteroalkyl, heteroalkenyl, heteroalkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, heteroalkyl, "substituted" or "unsubstituted" heteroalkenyl, "substituted" or "unsubstituted" heteroalkynyl, "substituted" or "unsubstituted", "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3{}^+X^-$, $—N(OR^{cc})R^{bb}$, —SH, $—SR^{aa}$, $—SSR^{cc}$, $—C(═O)R^{aa}$, $—CO_2H$, —CHO, $—C(OR^{cc})_2$, $—CO_2R^{aa}$, $—OC(═O)R^{aa}$, $—OCO_2R^{aa}$, $—C(═O)N(R^{bb})_2$, $—OC(═O)N(R^{bb})_2$, $—NR^{bb}C(═O)R^{aa}$, $—NR^{bb}C_2R^{aa}$, $—NR^{bb}C(═O)N(R^{bb})_2$, $—C(═NR^{bb})R^{aa}$, $—C(═NR^{bb})OR^{aa}$, $—OC(═NR^{bb})R^{aa}$, $—OC(═NR^{bb})OR^{aa}$, $—C(═NR^{bb})N(R^{bb})_2$, $—OC(═NR^{bb})N(R^{bb})_2$, $—NR^{bb}C(═NR^{bb})N(R^{bb})_2$, $—C(═O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(═O)R^{aa}$, $—OS(═O)R^{aa}$, $—Si(R^{aa})_3$, $—OSi(R^{aa})_3$$—C(═S)N(R^{bb})_2$, $—C(═O)SR^{aa}$, $—C(═S)SR^{aa}$, $—SC(═S)SR^{aa}$, $—SC(═O)SR^{aa}$, $—OC(═O)SR^{aa}$, $—SC(═O)OR^{aa}$, $—SC(═O)R^{aa}$, $—P(═O)(R^{aa})_2$, $—P(═O)(OR^{cc})_2$, $—OP(═O)(R^{aa})_2$, $—OP(═O)(OR^{cc})_2$, $—P(═O)(N(R^{bb})_2)_2$, $—OP(═O)(N(R^{bb})_2)_2$, $—NR^{bb}P(═O)(R^{aa})_2$, $—NR^{bb}P(═O)(OR^{cc})_2$, $—NR^{bb}p(═O)(N(R^{bb})_2)_2$, $—P(R^{cc})_2$, $—P(OR^{cc})_2$, $—P(R^{cc})_3{}^+X^-$, $—P(OR^{cc})_3{}^+X^-$, $—P(R^{cc})_4$, $—P(OR^{cc})_4$, $—OP(R^{cc})_2$, $—OP(R^{cc})_3{}^+X^-$, $—OP(OR^{cc})_2$, $—OP(OR^{cc})_3{}^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, $═NN(R^{bb})_2$, $═NNR^{bb}C(═O)R^{aa}$, $═NNR^{bb}C(═O)OR^{aa}$, $═NNR^{bb}S(═O)_2R^{aa}$, $═NR^{bb}$, or $═NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, —C(=O)$R^{aa}$, —C(=O)N($R^{cc}$)$_2$, —$CO_2R^{aa}$, —$SO_2R^{aa}$, —C(=N$R^{cc}$)O$R^{aa}$, —C(=N$R^{cc}$)N($R^{cc}$)$_2$—$SO_2$N($R^{cc}$)$_2$, —$SO_2R^{cc}$, —$SO_2OR^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —O$R^{ee}$, —ON($R^{ff}$)$_2$, —N($R^{ff}$)$_2$, —N($R^{ff}$)$_3^+X^-$, —N(O$R^{ee}$)$R^{ff}$, —SH, —S$R^{ee}$, —SS$R^{ee}$, —C(=O)$R^{ee}$, —$CO_2H$, —$CO_2R^{ee}$, —OC(=O)$R^{ee}$, —O$CO_2R^{ee}$, —C(=O)N($R^{ff}$)$_2$, —OC(=O)N($R^{ff}$)$_2$, —N$R^{ff}$C(=O)$R^{ee}$, —N$R^{ff}CO_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{aa}$)$_2$, —N$R^{ff}$C(=N$R^{ff}$)N($R^{ff}$)$_2$, —N$R^{ff}SO_2R^{ee}$, —$SO_2$N($R^{ff}$)$_2$, —$SO_2R^{ee}$, —$SO_2OR^{ee}$, —O$SO_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)$^+X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —O$CO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NH$CO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_1$. 6 alkyl), —OC(NH)$NH_2$, —NHC(NH)N($C_{1-6}$ alkyl)$_2$, —NHC(=NH)$NH_2$, —NH$SO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —O$SO_2C_{1-6}$ alkyl, —SO$C_{1-5}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $S_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, —C(=S)S($R^{X1}$), —C(=N$R^{X1}$)

$R^{X1}$, —C(═$NR^{X1}$)$OR^{X1}$, —C(═$NR^{X1}$)$SR^{X1}$, or —C(═$NR^{X1}$)N($R^{X1}$)$_2$, wherein each $R^{X1}$ is independently hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$—$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$—P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, each nitrogen atom substituent is independently substituted (e.g., substituted with one or more halogen) or unsubstituted $C_{1-6}$ alkyl, —C(═O)$R^{aa}$, —$CO_2R^{aa}$, —C(═O)N($R^{bb}$)$_2$, or a nitrogen protecting group. In certain embodiments, each nitrogen atom substituent is independently substituted (e.g., substituted with one or more halogen) or unsubstituted $C_{1-10}$alkyl, —C(═O)$R^{aa}$, —$CO_2R^{aa}$, —C(═O)N($R^{bb}$)$_2$, or a nitrogen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each nitrogen atom substituent is independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include, but are not limited to, —OH, —$OR^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $—S(═O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In some embodiments, two instances of a nitrogen protecting group together with the nitrogen atoms to which the nitrogen protecting groups are attached are N,N'-isopropylidenediamine.

In certain embodiments, at least one nitrogen protecting group is Bn, Boc, Cbz, Fmoc, trifluoroacetyl, triphenylmethyl, acetyl, or Ts.

In certain embodiments, each oxygen atom substituent is independently substituted (e.g., substituted with one or more halogen) or unsubstituted $C_{1-10}$alkyl, $—C(═O)R^{aa}$, $—CO_2R^{aa}$, $—C(═O)N(R^{bb})_2$, or an oxygen protecting group. In certain embodiments, each oxygen atom substituents is independently substituted (e.g., substituted with one or more halogen) or unsubstituted $C_{1-6}$ alkyl, $—C(═O)R^{aa}$, $—CO_2R^{aa}$, $—C(═O)N(R^{bb})_2$, or an oxygen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each oxygen atom substituent is independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{aa}$, $—SO_2R^{aa}$, $—Si(R^{aa})_3$, $—P(R^{cc})_2$, $—P(R^{cc})_3^+X^-$, $—P(OR^{cc})_2—P(OR^{cc})_3^+X^-$, $—P(═O)(R^{cc})_2$, $—P(═O)(OR^{cc})_2$, and $—P(═O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, at least one oxygen protecting group is silyl, TBDPS, TBDMS, TIPS, TES, TMS, MOM, THP, t-Bu, Bn, allyl, acetyl, pivaloyl, or benzoyl.

In certain embodiments, each sulfur atom substituent is independently substituted (e.g., substituted with one or more halogen) or unsubstituted $C_{1-10}$ alkyl, —C(═O)$R^{aa}$, —$CO_2R^{aa}$, —C(═O)N($R^{bb}$)$_2$, or a sulfur protecting group. In certain embodiments, each sulfur atom substituent is independently substituted (e.g., substituted with one or more halogen) or unsubstituted $C_{1-10}$alkyl, —C(═O)$R^{aa}$, —$CO_2R^{aa}$, —C(═O)N($R^{bb}$)$_2$, or a sulfur protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each sulfur atom substituent is independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). In some embodiments, each sulfur protecting group is selected from the group consisting of —$R^{aa}$, —N($R^{bb}$)$_2$, —C(═O)S$R^{aa}$, —C(═O)$R^{aa}$, —$CO_2R^{aa}$, —C(═O)N($R^{bb}$)$_2$, —C(═N$R^{bb}$)$R^{aa}$, —C(═N$R^{bb}$)O$R^{aa}$, —C(═N$R^{bb}$)N($R^{bb}$)$_2$, —S(═O)$R^{aa}$, —$SO_2R^{aa}$, —Si($R^{aa}$)$_3$, —P($R^{cc}$)$_2$, —P($R^{cc}$)$_3^+X^-$, —P(O$R^{cc}$)$_2$—P(O$R^{cc}$)$_3^+X^-$, —P(═O)($R^{aa}$)$_2$, —P(═O)(O$R^{cc}$)$_2$, and —P(═O)(N($R^{bb}$)$_2$)$_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(═O)S$R^{aa}$, —OC(═O)$R^{aa}$, —O$CO_2R^{aa}$, —OC(═O)N($R^{bb}$)$_2$, —OC(═N$R^{bb}$)$R^{aa}$, —OC(═N$R^{bb}$)O$R^{aa}$, —OC(═N$R^{bb}$)N($R^{bb}$)$_2$, —OS(═O)$R^{aa}$, —O$SO_2R^{aa}$, —OP($R^{cc}$)$_2$, —OP($R^{cc}$)$_3$, —OP(═O)($R^{aa}$)$_2$, —OP(═O)(O$R^{cc}$)$_2$, and —OP(═O)(N$R^{bb}$)$_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. Compound (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "stoichiometric solvate" refers to a solvate, which comprises a compound (e.g., a compound disclosed herein) and a solvent, wherein the solvent molecules are an integral part of the crystal lattice, in which they interact strongly with the compound and each other. The removal of the solvent molecules will cause instability of the crystal network, which subsequently collapses into an amorphous phase or recrystallizes as a new crystalline form with reduced solvent content.

The term "non-stoichiometric solvate" refers to a solvate, which comprises a compound (e.g., a compound disclosed herein) and a solvent, wherein the solvent content may vary without major changes in the crystal structure. The amount of solvent in the crystal lattice only depends on the partial pressure of solvent in the surrounding atmosphere. In the fully solvated state, non-stoichiometric solvates may, but not necessarily have to, show an integer molar ratio of solvent to the compound. During drying of a non-stoichiometric solvate, a portion of the solvent may be removed without significantly disturbing the crystal network, and the resulting solvate can subsequently be resolvated to give the initial crystalline form. Unlike stoichiometric solvates, the desolvation and resolvation of non-stoichiometric solvates is not accompanied by a phase transition, and all solvation states represent the same crystal form.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" refer to compounds that are interchangeable forms of a particular compound structure, and that vary in the displacement of hydrogen atoms and electrons. Thus, two structures may be in equilibrium through the movement of R electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest. The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at 2θ of, e.g., between 2° and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a 2θ of between 2° and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "co-crystal" refers to a crystalline structure comprising at least two different components (e.g., a compound disclosed herein and an acid), wherein each of the components is independently an atom, ion, or molecule. In certain embodiments, none of the components is a solvent. In certain embodiments, at least one of the components is a solvent. A co-crystal of a compound disclosed herein and an acid is different from a salt formed from a compound disclosed herein and the acid. In the salt, a compound disclosed herein is complexed with the acid in a way that proton transfer (e.g., a complete proton transfer) from the acid to a compound disclosed herein easily occurs at room temperature. In the co-crystal, however, a compound disclosed herein is complexed with the acid in a way that proton transfer from the acid to a compound disclosed herein does not easily occur at room temperature. In certain embodiments, in the co-crystal, there is no proton transfer from the acid to a compound disclosed herein. In certain embodiments, in the co-crystal, there is partial proton transfer from the acid to a compound disclosed herein. Co-crystals may be useful to improve the properties (e.g., solubility, stability, and ease of formulation) of a compound disclosed herein.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of Compound (I), which have cleavable groups and become by solvolysis or under physiological conditions Compound (I) which are pharmaceutically active in vivo. Such examples include, but are not limited to, ester derivatives and the like. Other derivatives of the compounds of this disclosure have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this disclosure are particular prodrugs. In some cases it is desirable to prepare double ester type prodrugs such as (acyloxy)alkyl esters or ((alkoxycarbonyl)oxy)alkylesters.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal. A subject who is resistant to treatment with a BTK inhibitor is one who shows no or minimal response to the treatment. In some embodiments, response to a treatment is measured by reduction in tumor cells or tumor cell killing. In some embodiments, response to a treatment is measured by changes in symptoms of the disease, condition or malignancy (e.g., a proliferative disease). It has been discovered that the compounds that block ATP binding to HCK as described herein are able to cause tumor cell killing even in cells that are derived from subjects who are resistant to a BTK inhibitor treatment.

The terms "administer," "administering," or "administration," refers to implanting, absorbing, ingesting, injecting, inhaling, or otherwise introducing a compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably. The treatment may be therapeutic treatment (not including prevention or prophylactic treatment).

An "effective amount" of Compound (I) refers to an amount sufficient to elicit the desired biological response, i.e., treating the condition. As will be appreciated by those of ordinary skill in this art, the effective amount of Compound (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of a compound may reduce the tumor burden or stop the growth or spread of a tumor.

A "therapeutically effective amount" of Compound (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms or causes of the condition, or enhances the therapeutic efficacy of another therapeutic agent.

A "prophylactically effective amount" of Compound (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (e.g., breast cancer, colon cancer, testicular cancer, CNS cancer, stomach cancer, lymphoma (e.g., B-cell Lymphoma (e.g., lymphoplasmacytic lymphoma (e.g., IgM secreting (i.e., Waldenstram's Macroglobulinemia), non-IgM secreting)), Diffuse Large B-Cell Lymphoma (e.g., activated B-cell-like (ABC)-DLBCL, germinal center B-cell-like (GBC)-DLBCL)), Follicular Lymphoma, Marginal zone B-cell lymphoma, Small lymphocytic lymphoma (e.g. Chronic lymphocytic leukemia (CLL)), Mantle cell lymphoma), Leukemia (e.g., myelogenous leukemia (e.g., chronic myelogenous leukemia, acute myelogenous leukemia)), benign neoplasms, angiogenesis, inflammatory diseases, auto inflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). The cancer may be a solid tumor. The cancer may be a hematological malignancy. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphoblastic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL) (e.g., activated B-cell-like (ABC)-DLBCL, germinal center B-cell-like (GBC)-DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., IgM secreting lymphoplasmacytic lymphoma, i.e., Waldenstrom's macroglobulinemia, and non-IgM secreting lymphoplasmacytic lymphoma), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angio-immunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response.

Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, dermatitis (e.g., stasis dermatitis, allergic contact dermatitis, atopic dermatitis, irritant contact dermatitis, neurodermatitis perioral dermatitis, seborrheic dermatitis), hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, necrotizing enterocolitis, inflammatory rosacea. An ocular inflammatory disease includes post-surgical inflammation.

The term "kinase" refers to any enzyme that catalyzes the addition of phosphate groups to an amino acid residue of a protein. For example, a serine kinase catalyzes the addition of a phosphate group to serine residue in a protein. In certain embodiments, the kinase is a protein kinase. Examples of kinases include, but are not limited to, cytoplasmic tyrosine kinases (e.g., SRC family kinases (e.g., HCK, LYN, BLK, FRK), Tec family kinases (e.g., BTK)), a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20)), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3a, GSK3P), a CDK-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

Hematopoietic cell kinase (HCK) is a member of the src-family of protein tyrosine kinases, and is aberrantly up-regulated in WM cells. In myeloma cells, HCK is activated by interleukin 6 (IL6) through the IL6 co-receptor IL6ST (GP130).

Bruton's tyrosine kinase (BTK) is a member of the src-related BTK/Tec family of cytoplasmic tyrosine kinases, is required for B cell receptor signaling, plays a key role in B-cell maturation, and exhibits increased activation in a number of B-cell malignancies.

LYN proto-oncogene (LYN) is a member of the src-family of protein tyrosine kinases, plays an important role in the regulation of B-cell differentiation, proliferation, survival and apoptosis, is important for immune self-tolerance, and acts downstream of several immune receptors, including the B-cell receptor (BCR). Without wishing to be bound by theory, BCR signaling is thought to be involved in pro-growth and survival signaling in MYD88 mutated disease, as well as being involved in non-MYD88 mutated disease. For example, BCR signaling is thought to be active in Waldenström's Macroglobulinemia, ABC subtype of diffuse large B-cell lymphoma, and chronic lymphocytic leukemia.

Proto-oncogene tyrosine-protein kinase SRC (SRC) is a protein tyrosine kinase, plays a central role in the regulation of a variety of biological processes, such as cell proliferation, migration, adhesion, and survival in solid tumors, and is overexpressed in Waldenström's Macroglobulinemia.

As used herein "inhibition", "inhibiting", "inhibit" and "inhibitor", and the like, refer to the ability of a compound to reduce, slow, halt, block, or prevent activity of a particular biological process (e.g., a kinase (e.g., SFK (e.g., HCK, LYN, BLK, FRK), Tec family kinases (e.g., BTK)) in a cell relative to vehicle.

The terms "block" or "blocking" refer to the ability of a compound to prevent a biological interaction (e.g., binding) in a cell relative to a negative control, e.g., vehicle. For example, a compound can block ATP from binding to the ATP binding pocket of a kinase. Such blocking may occur by direct binding of the compound to the ATP binding pocket itself, or indirect blocking. In some embodiments, the term refers to a reduction in the level of binding of ATP to a kinase, e.g., BTK and/or HCK, and/or LYN, and/or SRC, to a level that is statistically significantly lower than an initial level, which may, for example, be a baseline level of ATP binding. In some embodiments, the term refers to a reduction in the level of ATP binding to a kinase, e.g., BTK and/or HCK, and/or LYN, and/or SRC, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of ATP binding. In some embodiments, blocking ATP binding leads to a reduction in the level of enzyme activity, e.g., BTK and/or HCK, and/or LYN, and/or SRC activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound or pharmaceutical composition is referred to as "selectively," "specifically," or "competitively" binding a first protein, the compound binds the first protein, e.g., BTK or HCK or LYN or SRC, with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein that is different from the first protein, e.g., BTK. In some embodiments, a compound blocks ATP binding to a first protein, e.g., HCK or LYN or SRC, at a lower concentration (e.g., not less than about 2-fold, not less than about 5-fold, not less than about 10-fold, not less than about 30-fold, not less than about 100-fold, not less than about 1,000-fold, or not less than about 10,000-fold) than it blocks ATP binding a second protein that is different from the first protein, e.g., BTK.

Compounds which selectively block ATP binding to a kinase (e.g., BTK, HCK, LYN) provided herein can be identified and/or characterized by methods known in the art. Methods include purified enzyme and cell based biochemical and binding assays such as an HCK gatekeeper mutant rescue assay, an in vitro kinase assay, e.g., using HCK gatekeeper mutated kinase, competitive binding assays using KiNativ™ (a biochemical kinase profiling assay) technology or biotin tagged inhibitors, e.g., HCK inhibitors. Suitable assays for determining selective inhibition of HCK by a compound include, but are not limited to, Life Technology Z-Lyte activity assays (e.g., including HCK gatekeeper mutants and $GK^{+}6$ mutants); DiscoverX KINOMEscan®, a biochemical kinase assay for determination of kinome compound potency and selectivity; MRC radioactivity assays; ACD $Ba/F_3$ viability assays (e.g., including HCK gatekeeper mutants and $GK^{+}6$ mutants); Yeast hybrid proliferation assays; Protein thermostability assays; and cancer cells with HCK gatekeeper mutants or $GK^{+}6$ mutants proliferation-rescue assays. Such assays can also be used to determine selective inhibition of LYN and/or SRC by a compound.

The term "MYD88 mutation" means any change or difference in the nucleic acid or protein sequence of MYD88 as compared to the wild type sequence that results in the activation of MYD88 which leads to the activation of NF-κB. Mutations include, but are not limited to, nonsense mutations, missense mutations, frameshift mutations, rearrangement mutations, insertion mutations and deletion mutations. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P). In some embodiments, the mutation is another activating mutation in MYD88, such as V217F, W218R, I220T, S222R, M232T, S243N, T294P. Signaling studies show that SU-DHL-2 lymphoma cells that express the serine to arginine mutation at amino acid position 222 also have upregulated HCK (Yang et al, Blood 2016). In some embodiments, Sanger sequencing, whole exome or whole genome sequencing can be used to identify somatic mutations in MYD88.

The term "MYD88 mutated disease" or "disease associated with mutated MYD88" means any disease in a subject that is related to a change or difference in the nucleic acid or protein sequence of MYD88 as compared to the wild type sequence that results in the activation of MYD88 which leads to the activation of NF-κB. In some embodiments, mutated MYD88 is associated with Waldenstram's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia. In some embodiments, mutated MYD88 is associated with susceptibility to infectious disease. In some embodiments, mutated MYD88 is associated with susceptibility to autoimmune disease.

BRIEF DESCRIPTION OF THE DRAWINGS

FIG. 2 shows Compound (I) selectively targets HCK, BTK and LYN in MYD88 mutated WM and ABC DLBCL cells. FIG. 2A shows the results of a KINOMEscan®, the biochemical kinase assay for determination of kinome compound potency and selectivity for Compound (I) and A419259 against a panel of 464 kinases.

FIG. 5 shows HCK gatekeeper mutant ($HCK^{T333M}$) rescues Compound (I) induced cell death and blocks HCK activation and its downstream signaling in BCWM.1 WM cells.

FIG. 6 shows HCK gatekeeper mutant ($HCK^{T333M}$) rescues Compound (I) induced cell death and blocks HCK activation and its downstream signaling in MWCL-1 WM cells.

FIG. 7 shows HCK gatekeeper mutant ($HCK^{T333M}$) rescues Compound (I) induced cell death and blocks HCK activation and its downstream signaling in TMD8 ABC DLBCL cells.

FIG. 8 shows the in vitro and in vivo pharmacokinetics properties of Compound (I).

DETAILED DESCRIPTION OF CERTAIN EMBODIMENTS OF THE INVENTION

Figure 1:
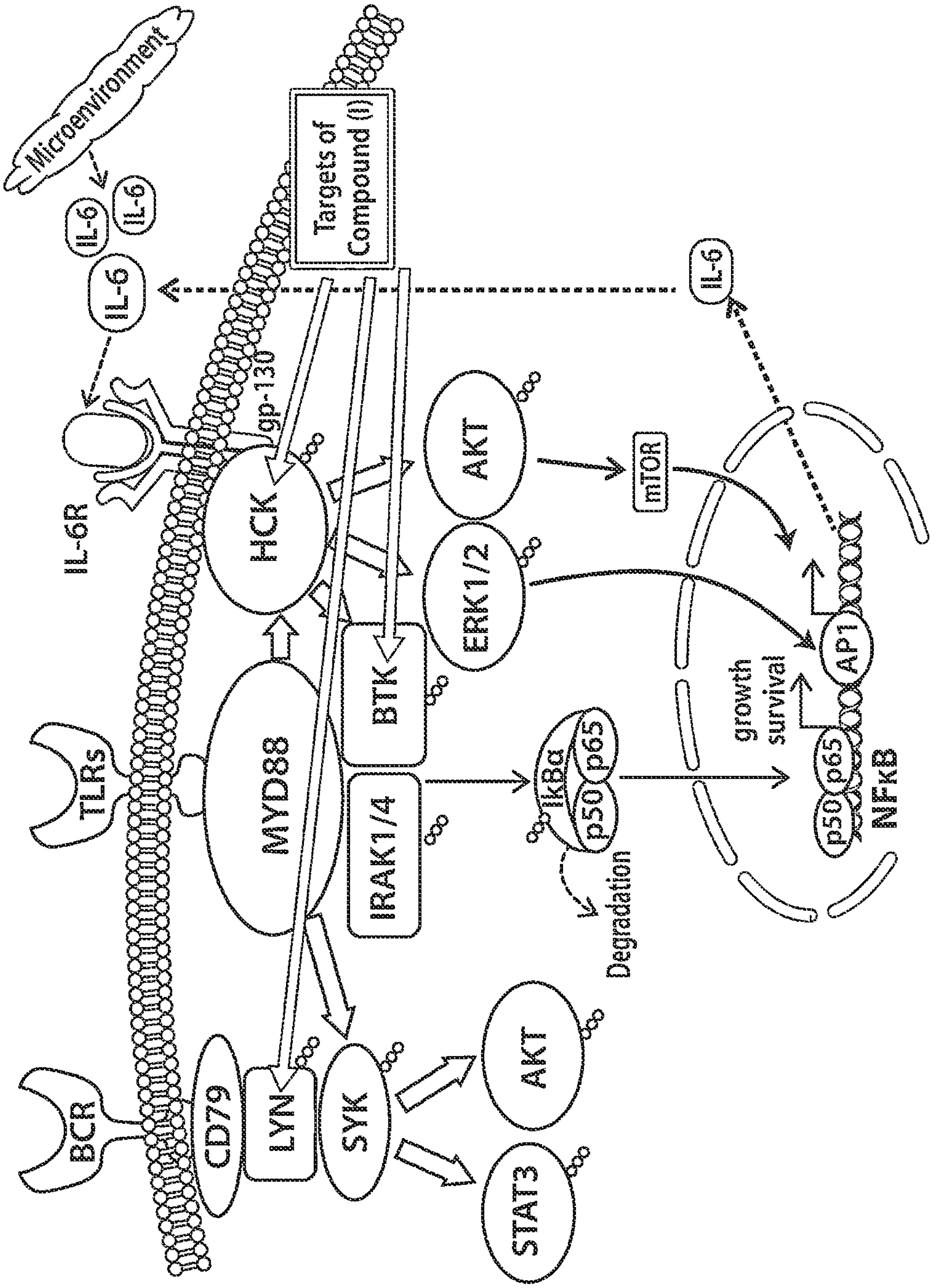
FIG. 1 shows the possible kinases targeted by Compound (I).

This disclosure is based, in part, on the surprising finding that subjects treated with Compound (I) displayed increased survivability as compared to subjects treated with other BTK inhibitors (e.g., ibrutinib, A419259). Without wishing to be bound by any theory, the increased survivability may result from a lower half-life in vivo of Compound (I) compared to other BTK inhibitors (e.g., A419259). A lower half-life of Compound (I) compared to other BTK inhibitors (e.g., A419259) may lead to decreased toxicity of the compound. In certain embodiments, the half-life of Compound (I) is lower than 20% of the half-life of other BTK inhibitors (e.g., A419259) in vivo. In certain embodiments, the half-life of Compound (I) is lower than 10% of the half-life of other BTK inhibitors (e.g., A419259) in-vivo.

Provided herein are methods of treating a disease (e.g., a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenstram's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))) in a subject in need thereof, comprising administering to the subject a therapeutically effective amount of Compound (I), of the formula:

(I)

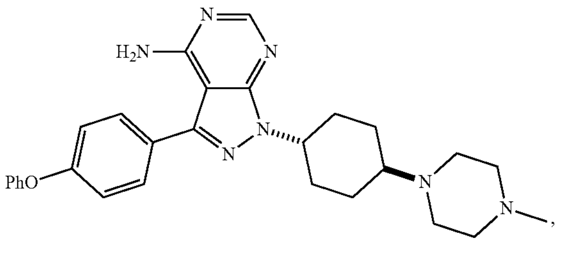

or a pharmaceutically acceptable salt, solvate, hydrate, polymorph, co-crystal, isotopically-labeled derivative, stereoisomer, or prodrug thereof. In certain embodiments, the method comprises administering Compound (I), or a pharmaceutically acceptable salt thereof. In certain embodiments, the diseases is associated with a mutated MYD88 protein. In certain embodiments, the disease is associated with a mutated BTK protein. In certain embodiments, the disease is associated with a C481 mutated BTK protein. In certain embodiments, the disease is associated with a C481S mutated BTK protein. In some embodiments, the diseases are associated with aberrant activity of a kinase (e.g., SRC Family kinases (e.g., HCK, LYN, BLK, FRK), Tec family kinases (e.g., BTK). In certain embodiments, the disease is resistant to inhibition by a BTK inhibitor (e.g., ibrutinib, CC-292, ONO-4059, evobrutinib, spebrutinib, BGB-3111, HM71224, or ACP-196). In certain embodiments, the disease is resistant to treatment with ibrutinib. In certain embodiments, the disease is associated with a mutated BTK protein (e.g., a C481S mutated BTK), and the disease is resistant to treatment with a ibrutinib.

Further provided herein are methods of inhibiting the activity of a kinase in a subject, comprising administering to the subject a therapeutically effective amount of Compound (I) of the formula:

(I)

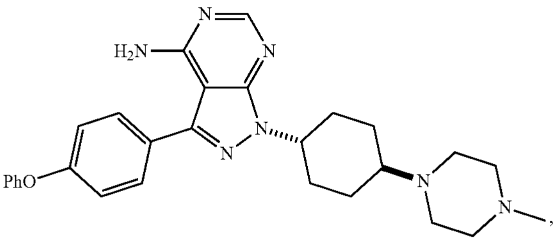

or a pharmaceutically acceptable salt, solvate, hydrate, polymorph, co-crystal, isotopically-labeled derivative, stereoisomer, or prodrug thereof. In certain embodiments, the kinase is an SRC Family kinase (e.g., HCK, LYN, BLK, FRK). In other embodiments, the kinase is a Tec family kinase (e.g., BTK). In certain embodiments, the BTK is resistant to inhibition by a BTK inhibitor (e.g., ibrutinib, CC-292, ONO-4059, evobrutinib, spebrutinib, BGB-3111, HM71224, or ACP-196). In certain embodiments, the BTK is ibrutinib resistant.

Provided herein is a method of treating a subject comprising administering to a subject with an MYD88 mutated disease. An MYD88 mutated disease can include, but is not limited to a proliferative disease (e.g., an IgM gammopathy (e.g., an IgM Monoclonal gammopathy of undetermined significance (MGUS), amyloid light chain (AL) amyloidosis), mastocytosis (e.g., systemic mastocytosis) cancer (e.g., breast cancer, colon cancer, testicular cancer, CNS cancer, stomach cancer, lymphoma (e.g., B-cell lymphoma (e.g., lymphoplasmacytic lymphoma (e.g., IgM secreting lymphoplasmacytic lymphoma (i.e., Waldenstrom's Macroglobulinemia), non-IgM secreting lymphoplasmacytic lymphoma)), diffuse large B-cell lymphoma (e.g., activated B-cell-like (ABC)-DLBCL, germinal center B-cell-like (GBC)-DLBCL), follicular lymphoma, marginal zone B-cell lymphoma, small lymphocytic lymphoma, mantle cell lymphoma), myeloma (e.g., IgM myelomas (e.g., IgM multiple myeloma)), and leukemia (e.g., chronic lymphocytic leukemia (CLL), acute lymphoblastic leukemia, myelogenous leukemia (e.g., chronic myelogenous leukemia, acute myelogenous leukemia (e.g., mast cell leukemia) myeloproliferative diseases (e.g., myelodysplastic syndrome))))) a pharmaceutical composition comprising Compound (I) as described herein. In certain embodiments, the subject being treated has previously undergone treatment with ibrutinib. In certain embodiments, the subject being treated has developed ibrutinib resistance.

In some embodiments, the provided methods include inhibiting LYN and/or SRC comprising the steps of administering to the subject a therapeutically effective amount of Compound (I), or a pharmaceutically acceptable salt, solvate, hydrate, polymorph, co-crystal, isotopically-labeled derivative, stereoisomer, or prodrug thereof.. In some embodiments, the method further comprises administering an agent which inhibits LYN and/or SRC. For example, in some embodiments, Compound (I) as described herein is administered to the subject in combination (e.g., concurrently or sequentially) with an agent which blocks ATP binding to SRC. In some embodiments, Compound (I) as described herein is administered to the subject in combination (e.g., concurrently or sequentially) with an agent which blocks ATP binding to LYN. In some embodiments, Compound (I) as described herein is administered to the subject in combination (e.g., concurrently or sequentially) with an agent which blocks ATP binding to HCK.

In some embodiments, the provided methods include inhibiting Tec family kinases comprising the steps of administering to the subject a therapeutically effective amount of Compound (I), or a pharmaceutically acceptable salt, solvate, hydrate, polymorph, co-crystal, isotopically-labeled derivative, stereoisomer, or prodrug thereof. In some embodiments, the provided methods include inhibiting BTK comprising the steps of administering to the subject a therapeutically effective amount of Compound (I), or a pharmaceutically acceptable salt, solvate, hydrate, polymorph, co-crystal, isotopically-labeled derivative, stereoisomer, or prodrug thereof. In some embodiments, the method further comprises administering an agent which inhibits BTK and/or other Tec family kinases. For example, in some embodiments, Compound (I) as described herein is administered to the subject in combination (e.g., concurrently or sequentially) with an agent which blocks ATP binding to a Tec family kinase. In some embodiments, Compound (I) as described herein is administered to the subject in combination (e.g., concurrently or sequentially) with an agent which blocks ATP binding to BTK.

In some embodiments, selective inhibition of HCK and/or LYN and/or SRC by a compound can be determined by a native protein kinase activity profiling assay such as a KiNativ™ (a biochemical kinase profiling assay) profiling. As described in the Example, in some embodiments, the ability of inhibitors to protect kinases from subsequent labeling with a reactive ATP-biotin probe can be determined. Living cells can be treated with Compound (I), followed by lysis treatment with ATP-biotin and western blotting for BTK and HCK and/or LYN and/or SRC. It can be determined whether the compound tested blocks ATP binding to HCK and/or LYN and/or SRC at one or more particular concentrations, and whether the compound tested blocks ATP binding to BTK at the one or more concentrations. In such an assay, blocking of binding to ATP can be determined by lack of a detectable band on Western blot when performed under the conditions described in Example 1. In some embodiments, the compound blocks ATP binding to HCK and/or LYN and/or SRC at a concentration at least 10-fold, at least 30-fold, at least 50-fold, at least 100-fold, at least 150-fold, at least 200-fold, at least 250-fold, at least 300-fold, at least 350-fold, at least 400-fold, at least 450-fold, at least 500-fold, at least 750-fold, or at least 1000-fold, lower than the concentration at which it blocks ATP binding to BTK under equivalent conditions. In some embodiments, a compound blocks ATP binding to HCK and/or LYN and/or SRC at a concentration at least 10-fold lower than the concentration at which it blocks ATP binding to Bruton's Tyrosine Kinase (BTK) under equivalent conditions.

One skilled in the art will appreciate that many suitable methods, in addition to and including the ones discussed in the examples, can be used to detect mutations in the MYD88 gene. Detection methods that can be used include, but are not limited to, direct sequencing, DNA chip technologies, mass spectroscopy, polymerase chain reaction (PCR), allele specific polymerase chain reaction, real time polymerase chain reaction, reverse transcriptase PCR, electrophoretic mobility, nucleic acid hybridization, fluorescent in situ hybridization, and denaturing high performance liquid chromatography. In some embodiments, mutations in the MYD88 gene may be detected by allele specific polymerase chain reaction (AS-PCR), e.g., as described in WO 2013/006443.

One or more symptoms or clinical features of LPL include anemia, hyper-viscosity, neuropathy, coagulopathies, splenomegaly, hepatomegaly, adenopathy, and an IgM serum paraprotein. In addition, the subject may also present one or more of the following clinical features or symptoms of other B cell neoplasms: asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia. A subject suspected of having one or more of Waldenstram's Macroglobulinemia (i.e., IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia may be assessed for the presence of a mutation in the gene encoding MYD88, e.g., at position 38182641 in chromosome 3p22.2, as well as other activating mutations in MYD88 (including but not limited to V217F, W218R, I220T, S222R, M232T, S243N, and T294P).

In some embodiments, treatment further includes administering to the subject an agent, e.g., an anti-cancer agent, in combination with a compound described herein. In some embodiments, treatment further includes administering to the subject one or more of bendamustine, fludarabine, bortezomib, or idelalisib. In some embodiments, treatment further includes administering to the subject one or more of a BCL-2 inhibitor (e.g., venetoclax, navitoclax, obatoclax), a BCL-2/BCL-xL inhibitor (e.g., APG-1252, BM-1197), a proteasome inhibitor (e.g., bortezomib, carfilzomib, ixazomib or oprozomib), a monoclonal antibody (e.g., rituximab, daratumumab, ofatumumab or obinituzumab), an alkylator drug (e.g., bendamustine, cyclophosphamide), a nucleoside analogue (e.g., fludarabine or cladribine), an MTOR inhibitor (e.g., everolimus), a BTK inhibitor (e.g., ibrutinib, acalabrutinib or BGB-3111), a BCR inhibitor (e.g., a SYK inhibitor) and/or an immunomodulating agent (e.g., thalidomide or lenalidomide). In some embodiments, the anti-cancer agent is a monoclonal antibody, e.g., rituximab. In some embodiments, the anti-cancer agent is a chemotherapeutic drug such as chlorambucil, cyclophosphamide, or vincristine or thalidomide. Corticosteroids, such as Prednisone, may also be used in combination. Plasmapheresis can be used to treat the hyperviscosity syndrome by removing the paraprotein from the blood. Autologous bone marrow transplantation may be used in combination with compounds described herein. In some embodiments, treatment further includes administering to the subject an agent that inhibits LYN and/or SRC.

When administered to a subject, effective amounts of the therapeutic agent will depend on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved In the treatment of an MYD88 mutated disease, such as Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia, an effective amount of a selective HCK inhibitor is that amount which slows the progression of the disease, halts the progression of the disease, or reverses the progression of the disease. An effective amount includes, but is not limited to, that amount necessary to slow, reduce, inhibit, ameliorate or reverse one or more symptoms associated with the MYD88 mutated disease. In some embodiments, such terms refer to a reduction in the levels of IgM serum paraprotein, anemia, hyper-viscosity, neuropathy, coagulopathies, splenomegaly, hepatomegaly, and adenopathy.

Pharmaceutical preparations and compounds are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present disclosure may include or be diluted into a pharmaceutically-acceptable carrier. The term "pharmaceutically-acceptable carrier" as used herein means one or more compatible fillers, diluants or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present disclosure, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa. The present disclosure also provides pharmaceutical compositions comprising a compound described herein and optionally a pharmaceutically acceptable excipient.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a kinase (e.g., SFK (e.g., LYN, HCK), Tec family kinases (e.g., BTK)) in a subject, improve bioavailability, improve safety, reduce drug resistance, reduce and/or modify metabolism, inhibit excretion, and/or modify distribution in a subject. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, cancer, inflammatory disease, autoimmune disease, genetic disease, hematological disease, neurological disease, painful condition, psychiatric disorder, or metabolic disorder) or premalignant condition. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, cytotoxic chemotherapeutic agents, epigenetic modifiers, glucocorticoids, immunotherapeutic agents, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE® (methotrexate), ADE, Adriamycin RDF® (doxorubicin hydrochloride), Ambochlorin® (chlorambucil), ARRANON® (nelarabine), ARZERRA® (ofatumumab), BOSULIF® (bosutinib), BUSULFEX® (busulfan), CAMPATH® (alemtuzumab), CERUBIDINE® (daunorubicin hydrochloride), CLAFEN® (cyclophosphamide), CLOFAREX (clofarabine), CLOLAR® (clofarabine), CVP, CYTOSAR-U® (cytarabine), CYTOXAN® (cyclophosphamide), ERWINAZE™ (Asparaginase Erwinia Chrysanthemi), FLUDARA® (fludarabine phosphate), FOLEX (methotrexate), FOLEX PFS (methotrexate), GAZYVA® (obinutuzumab), GLEEVEC® (imatinib mesylate), Hyper-CVAD, ICLUSIG® (ponatinib hydrochloride), IMBRUVICA® (ibrutinib), LEUKERAN® (chlorambucil), LINFOLIZIN (chlorambucil), MARQIBO® (vincristine sulfate liposome), METHOTREXATE LPF (methorexate), MEXATE® (methotrexate), MEXATE-AQ (methotrexate), mitoxantrone hydrochloride, MUSTARGEN® (mechlorethamine hydrochloride), MYLERAN® (busulfan), NEOSAR® (cyclophosphamide), ONCASPAR® (Pegaspargase), PURINETHOL® (mercaptopurine), PURIXAN® (mercaptopurine), Rubidomycin (daunorubicin hydrochloride), SPRYCEL® (dasatinib), SYNRIBO™ (omacetaxine mepesuccinate), TARABINE PFS (cytarabine), TASIGNA® (nilotinib), TREANDA® (bendamustine hydrochloride), TRISENOX® (arsenic trioxide), VINCASAR PFS® (vincristine sulfate), ZYDELIG® (idelalisib), or a combination thereof. In certain embodiments, the additional pharmaceutical agent is an anti-lymphoma agent. In certain embodiments, the additional pharmaceutical agent is ABITREXATE® (methotrexate), ABVD, ABVE, ABVE-PC, ADCETRIS® (brentuximab vedotin), ADRIAMYCIN PFS® (doxorubicin hydrochloride), ADRIAMYCIN RDF® (doxorubicin hydrochloride), AMBOCHLORIN® (chlorambucil), AMBOCLORIN® (chlorambucil), ARRANON® (nelarabine), BEACOPP, BECENUM (carmustine), BELEODAQ® (belinostat), BEXXAR (tositumomab and iodine 1131 tositumomab), BICNU® (carmustine), BLENOXANE (bleomycin), CARMUBRIS® (carmustine), CHOP, CLAFEN® (cyclophosphamide), COPP, COPP-ABV, CVP, CYTOXAN® (cyclophosphamide), DEPOCYT® (liposomal cytarabine), DTIC-DOME® (dacarbazine), EPOCH, FOLEX® (methotrexate), FOLEX PFS (methotrexate), FOLOTYN (pralatrexate), HYPER-CVAD, ICE, IMBRUVICA® (ibrutinib), INTRON A® (recombinant interferon alfa-2b), ISTODAX® (romidepsin), LEUKERAN® (chlorambucil), LINFOLIZIN (chlorambucil), GLEOSTINE® (Lomustine), MATULANE® (procarbazine hydrochloride), METHOTREXATE LPF (methotrexate), MEXATE (methotrexate), MEXATE-AQ (methotrexate), MOPP, MOZOBIL® (plerixafor), MUSTARGEN® (mechlorethamine hydrochloride), NEOSAR® (cyclophosphamide), OEPA, ONTAK™ (denileukin diftitox), OPPA, R—CHOP, REVLIMID® (lenalidomide), RITUXAN® (rituximab), STANFORD V, TREANDA® (bendamustine hydrochloride), VAMP, VELBAN® (vinblastine sulfate), VELCADE® (bortezomib), VELSAR® (vinblastine sulfate), VINCASAR PFS® (vincristine sulfate), ZEVALIN® (ibritumomab tiuxetan), ZOLINZA® (vorinostat), ZYDELIG® (idelalisib), or a combination thereof. In certain embodiments, the additional pharmaceutical agent is REVLIMID® (lenalidomide), DACOGEN® (decitabine), VIDAZA® (azacitidine), CYTOSAR-U® (cytarabine), IDAMYCIN® (idarubicin), CERUBIDINE® (daunorubicin), LEUKERAN® (chlorambucil), NEOSAR® (cyclophosphamide), FLUDARA® (fludarabine), LEUSTATIN® (cladribine), or a combination thereof. In certain embodiments, the additional pharmaceutical agent is ABITREXATE® (methotrexate), ABRAXANE® (paclitaxel albumin-stabilized nanoparticle formulation), AC, AC-T, ADE, ADRIAMYCIN PFS® (doxorubicin hydrochloride), ADRUCIL® (fluorouracil), AFINITOR® (everolimus), AFINITOR DISPERZ® (everolimus), ALDARA® (imiquimod), ALIMTA® (pemetrexed disodium), AREDIA® (pamidronate disodium), ARIMIDEX® (anastrozole), AROMASIN® (exemestane), AVASTIN® (bevacizumab), BECENUM (carmustine), BEP, BICNU® (carmustine), BLENOXANE® (bleomycin), CAF, CAMPTOSAR® (irinotecan hydrochloride), CAPOX, CAPRELSA® (vandetanib), CARBOPLATIN-TAXOL, CARMUBRIS (carmustine), CASODEX® (bicalutamide), CEENU® (lomustine), CERUBIDINE® (daunorubicin hydrochloride), CERVARIX™ (recombinant HPV bivalent vaccine), CLAFEN® (cyclophosphamide), CMF, COMETRIQ® (cabozantinib-s-malate), COSMEGEN® (dactinomycin), CYFOS (ifosfamide), CYRAMZA® (ramucirumab), CYTOSAR-U® (cytarabine), CYTOXAN® (cyclophosphamide), DACOGEN® (decitabine), DEGARELIX, DOXIL® (doxorubicin hydrochloride liposome), DOXORUBICIN HYDROCHLORIDE, DOX-SL (doxorubicin hydrochloride liposome), DTIC-DOME (dacarbazine), EFUDEX® (fluorouracil), ELLENCE® (epirubicin hydrochloride), ELOXATIN® (oxaliplatin), ERBITUX® (cetuximab), ERIVEDGE® (vismodegib), ETOPOPHOS® (etoposide phosphate), EVACET™ (doxorubicin hydrochloride liposome), FARESTON® (toremifene), FASLODEX® (fulvestrant), FEC, FEMARA® (letrozole), FLUOROPLEX® (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL® (recombinant human papillomavirus (HPV) quadrivalent vaccine), GEMCITABINE-CISPLATIN, GEMCITABINE-OXALIPLATIN, GEMZAR® (gemcitabine hydrochloride), GILOTRIF® (afatinib dimaleate), GLEEVEC® (imatinib mesylate), GLIADEL® (carmustine implant), GLIADEL® WAFER (carmustine implant), HERCEPTIN® (trastuzumab), HYCAMTIN® (topotecan hydrochloride), IFEX® (ifosfamide), IFOSFAMIDUM (ifosfamide), INLYTA® (axitinib), INTRON A® (recombinant interferon alfa-2b), IRESSA® (gefitinib), IXEMPRA® (ixabepilone), JAKAFI® (ruxolitinib phosphate), JEVTANA® (cabazitaxel), KADCYLA® (ado-trastuzumab emtansine), KEYTRUDA® (pembrolizumab), KYPROLIS® (carfilzomib), LIPODOX® (doxorubicin hydrochloride liposome), LUPRON (leuprolide acetate), LUPRON DEPOT®

(leuprolide acetate), LUPRON DEPOT-3 MONTH (leuprolide acetate), LUPRON DEPOT-4 MONTH (leuprolide acetate), LUPRON DEPOT-PED® (leuprolide acetate), MEGACE® (megestrol acetate), MEKINIST® (trametinib), METHAZOLASTONE (temozolomide), METHOTREXATE LPF (methotrexate), MEXATE® (methotrexate), MEXATE-AQ (methotrexate), MITOXANTRONE HYDROCHLORIDE, MITOZYTREX (mitomycin c), MOZOBIL® (plerixafor), MUSTARGEN® (mechlorethamine hydrochloride), MUTAMYCIN® (mitomycin c), MYLOSAR® (azacitidine), NAVELBINE® (vinorelbine tartrate), NEOSAR® (cyclophosphamide), NEXAVAR® (sorafenib tosylate), NOLVADEX® (tamoxifen citrate), OFF, PAD, PARAPLAT (carboplatin), PARAPLATIN® (carboplatin), PEG-INTRON® (peginterferon alfa-2b), PEMETREXED DISODIUM, PERJETA® (pertuzumab), PLATINOL® (cisplatin), PLATINOL®-AQ (cisplatin), POMALYST® (pomalidomide), prednisone, PROLEUKIN® (aldesleukin), PROLIA® (denosumab), PROVENGE® (sipuleucel-t), REVLIMID® (lenalidomide), RUBIDOMYCIN® (daunorubicin hydrochloride), SPRYCEL® (dasatinib), STIVARGA® (regorafenib), SUTENT® (sunitinib malate), SYLATRON™ (peginterferon alfa-2b), SYLVANT® (siltuximab), SYNOVIR® (thalidomide), TAC, TAFINLAR® (dabrafenib), TARABINE PFS (cytarabine), TARCEVA® (erlotinib hydrochloride), TASIGNA® (nilotinib), TAXOL (paclitaxel), TAXOTERE® (docetaxel), TEMODAR® (temozolomide), THALOMID® (thalidomide), TOPOSAR® (etoposide), TORISEL® (temsirolimus), TPF, TRISENOX® (arsenic trioxide), TYKERB® (lapatinib ditosylate), VECTIBIX® (panitumumab), VEIP, VELBAN® (vinblastine sulfate), VELCADE® (bortezomib), VELSAR® (vinblastine sulfate), VEPESID® (etoposide), VIADUR® (leuprolide acetate), VIDAZA® (azacitidine), VINCASAR PFS® (vincristine sulfate), VOTRIENT® (pazopanib hydrochloride), WELLCOVORIN® (leucovorin calcium), XALKORI® (crizotinib), XELODA® (capecitabine), XELOX, XGEVA® (denosumab), XOFIGO® (radium 223 dichloride), XTANDI® (enzalutamide), YERVOY® (ipilimumab), ZALTRAP® (ziv-aflibercept), ZELBORAF® (vemurafenib), ZOLADEX® (goserelin acetate), ZOMETA® (zoledronic acid), ZYKADIA® (ceritinib), ZYTIGA® (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade®)), mTOR inhibitors (e.g., rapamycin, temsirolimus (CCI-779), everolimus (RAD-001), ridaforolimus, AP23573 (Ariad), AZD8055, BEZ235, BGT226, XL765, PF-4691502, GDC0980, SF1126, and OSI-027), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin,, aminopterin, and hexamethyl melamine, or a combination thereof. In certain embodiments, the additional pharmaceutical agent is a cytotoxic chemotherapeutic agent (e.g., gemcitabine, cytarabine, daunorubicin, doxorubicin, vincristine, 1-asparaginase, cyclophosphamide, or etoposide). In certain embodiments, the additional pharmaceutical agent is an epigenetic modifier such as azacitidine or romidepsin. In certain embodiments, the additional pharmaceutical agent is ruxolitinib, BBT594, CHZ868, CYT387, or BMS911543. In certain embodiments, the additional pharmaceutical agent is an inhibitor of a tyrosine kinase. In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In certain embodiments, the additional pharmaceutical agent is a binder or inhibitor of a kinase (e.g., an SRC family kinase (e.g., HCK, LYN, BLK, FRK), A Tec family kinase (e.g., BTK)). In certain embodiments, the additional pharmaceutical agent is an antibody or a fragment thereof (e.g., monoclonal antibody). In certain embodiments, the additional pharmaceutical agent is a tyrosine kinase inhibitor. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is a glucocorticoid (e.g., cortisol, cortisone, prednisone, methylprednisolone, dexamethasone, betamethasone, triamcinolone, fludrocortisone acetate, or deoxycorticosterone acetate). In certain embodiments, the additional therapy is an immunotherapy (e.g., an immunotherapeutic monoclonal antibody). In certain embodiments, the additional pharmaceutical agent is an immunomodulator. In certain embodiments, the additional pharmaceutical agent is an immune checkpoint inhibitor. In certain embodiments, the additional pharmaceutical agent is a programmed cell death 1 protein (PD-1) inhibitor. In certain embodiments, the additional pharmaceutical agent is a programmed cell death 1 protein ligand 1 (PD-L1) inhibitor. In certain embodiments, the additional pharmaceutical agent is a cytotoxic T-lymphocyte-associated protein 4 (CTLA-4) inhibitor. In certain embodiments, the additional pharmaceutical agent is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GAL9) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor. In certain embodiments, the PD-1 inhibitor is nivolumab, pidilizumab, pembrolizumab, MEDI-0680, REGN2810, or AMP-224. In certain embodiments, the PD-L1 inhibitor is atezolizumab, durvalumab, BMS-936559, avelumab, or CA-170. In certain embodiments, the CTLA-4 inhibitor is ipilimumab or tremelimumab. In certain embodiments, the compounds described herein or pharmaceutical compositions can be administered in combination with an anti-cancer therapy including, but not limited to, surgery, radiation therapy, and transplantation (e.g., stem cell transplantation, bone marrow transplantation).

In certain embodiments, the additional pharmaceutical agent is a BCL-2 inhibitor (e.g., venetoclax, navitoclax, obatoclax), a BCL-2/BCL-xL inhibitor (e.g., APG-1252, BM-1197).

In certain embodiments, the additional pharmaceutical agent is venetoclax.

In certain embodiments, the compound described herein is provided in an effective amount (e.g., effective for inhibiting a kinase, such as a SRC family kinases (e.g., HCK, LYN, BLK, FRK), or Tec family kinases (e.g., BTK)) in the pharmaceutical composition. In certain embodiments, the effective amount is a therapeutically effective amount. In certain embodiments, a therapeutically effective amount is an amount effective for inhibiting a kinase. In certain embodiments, a therapeutically effective amount is an amount effective for treating a disease (e.g., a disease associated with aberrant activity of a kinase (e.g., proliferative disease)). In certain embodiments, a therapeutically effective amount is an amount effective for inhibiting the activity of a kinase and treating a disease (e.g., a disease associated with aberrant activity of a kinase (e.g., proliferative disease)). In certain embodiments, a therapeutically effective amount is an amount effective for inducing apoptosis in a cell (e.g., malignant cell, premalignant cell).

In certain embodiments, the effective amount is an amount effective for inhibiting the activity of a kinase by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a kinase by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human (e.g., an adult, juvenile, or child). In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the subject is a genetically engineered animal. In certain embodiments, the subject is a transgenic animal (e.g., transgenic mice, transgenic pigs). In certain embodiments, the subject is a fish or reptile.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum®), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum® (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20, a non-ionic detergent), polyoxyethylene sorbitan (Tween® 60, a non-ionic detergent), polyoxyethylene sorbitan monooleate (Tween® 80, a non-ionic detergent), sorbitan monopalmitate (Span® 40, a non-ionic surfactant), sorbitan monostearate (Span® 60, a non-ionic surfactant), sorbitan tristearate (Span® 65, a non-ionic surfactant), glyceryl monooleate, sorbitan monooleate (Span® 80, a non-ionic surfactant), polyoxyethylene esters (e.g., polyoxyethylene monostearate (Myrj® 45 a synthetic emulsifier), polyoxyethylene hydrogenated castor oil, polyethoxylated castor oil, polyoxymethylene stearate, and Solutol®, a non-ionic surfactant), sucrose fatty acid esters, polyethylene glycol fatty acid esters (e.g., Cremophor®, a non-ionic solubilizer and emulsifier), polyoxyethylene ethers, (e.g., polyoxyethylene lauryl ether (Brij® 30, a nonionic surfactant)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68 (a nonionic surfactant), poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®, a purified magnesium aluminum silicate clay), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus (an antimicrobial formaldehyde releaser preservative), Phenonip® (a mix of preservatives phenoxyethanol, methylparaben, ethylparaben, butylparaben, propylparaben, and isobutylparaben), methylparaben, Germall® 115 (an antimicrobial preservative), Germaben® II (an antimicrobial preservative), Neolone® (a broad spectrum antimicrobial preservative), Kathon® (a broad-spectrum microbicide), and Euxyl® (an antimicrobial preservative).

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *Eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor® (a non-ionic solubilizer and emulsifier), alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject, any two doses of the multiple doses include different or substantially the same amounts of a compound described herein. In certain embodiments, when multiple doses are administered to a subject, the frequency of administering the multiple doses to the subject is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject is one dose per day. In certain embodiments, the frequency of administering the multiple doses to the subject is two doses per day. In certain embodiments, the frequency of administering the multiple doses to the subject is three doses per day. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject or cell. In certain embodiments, the duration between the first dose and last dose of the multiple doses is three months, six months, or one year. In certain embodiments, the duration between the first dose and last dose of the multiple doses is the lifetime of the subject. In certain embodiments, a dose (e.g., a single dose, or any dose of multiple doses) described herein includes independently between 0.1 pg and 1 pg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Also encompassed by the present disclosure are kits (e.g., pharmaceutical packs). In certain embodiments, the kit comprises Compound (I) or a pharmaceutical composition described herein, and instructions for using the compound or pharmaceutical composition. In certain embodiments, the kit comprises a first container, wherein the first container includes the compound or pharmaceutical composition. In some embodiments, the kit further comprises a second container. In certain embodiments, the second container includes an excipient (e.g., an excipient for dilution or suspension of the compound or pharmaceutical composition). In certain embodiments, the second container includes an additional pharmaceutical agent. In some embodiments, the kit further comprises a third container. In certain embodiments, the third container includes an additional pharmaceutical agent. In some embodiments, the compound or pharmaceutical composition included in the first container and the excipient or additional pharmaceutical agent included in the second container are combined to form one unit dosage form. In some embodiments, the compound or pharmaceutical composition included in the first container, the excipient included in the second container, and the additional pharmaceutical agent included in the third container are combined to form one unit dosage form. In certain embodiments, each of the first, second, and third containers is independently a vial, ampule, bottle, syringe, dispenser package, tube, or inhaler.

In certain embodiments, the instructions are for administering the compound or pharmaceutical composition to a subject (e.g., a subject in need of treatment or prevention of a disease described herein). In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information.

In another aspect, the present disclosure provides methods of treating a disease in a subject in need thereof, the method comprising administering to the subject in need thereof an effective amount (e.g., therapeutically effective amount) of Compound (I) described herein or a pharmaceutical composition described herein.

In another aspect, the present disclosure provides methods of preventing a disease in a subject in need thereof, the method comprising administering to the subject in need thereof an effective amount (e.g., prophylactically effective amount) of a compound described herein or a pharmaceutical composition described herein.

In another aspect, the present disclosure provides methods of inhibiting the activity of a kinase in a subject in need thereof, the method comprising administering to the subject in need thereof an effective amount of a compound described herein or a pharmaceutical composition described herein.

Without wishing to be bound by any particular theory, in certain embodiments the compounds described herein are able to bind the kinase being inhibited. In certain embodiments, a compound described herein is able to bind to the kinase. In certain embodiments, the kinase is an SFK (e.g., HCK, LYN, BLK, FRK). In certain embodiments, the kinase is HCK. In certain embodiments, the kinase is LYN. In certain embodiments, the kinase is a Tec family kinase (e.g., BTK). In certain embodiments, the kinase is BTK.

In certain embodiments, provided are methods of decreasing the activity of a kinase (e.g., SFK (e.g., HCK, LYN, BLK, FRK), Tec family kinase (e.g., BTK)) in a subject by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a kinase in a subject is decreased by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a kinase in a subject is selectively inhibited by the method. In some embodiments, the activity of a kinase (e.g., HCK, LYN, BTK) in a subject is selectively decreased by a compound or pharmaceutical composition described herein.

A disease, including proliferative disease, may be associated with aberrant or undesired activity of a kinase, and/or overexpression of the kinase. Aberrant or undesired activity of a kinase may be an increased or a decreased level of activity of the kinase. Proliferative diseases are sometimes associate with abnormal levels of JAK activity, frequently through increased or decreased JAK activation. Inhibition of the activity of JAK2 would be expected to inhibit phosphorylation. In certain embodiments, JAK2 is not overexpressed, but the activity of JAK2 is increased. In certain embodiments, JAK2 is overexpressed, and the activity of JAK2 is increased. The compounds and pharmaceutical compositions described herein may inhibit the activity of JAK2 and be useful in treating and/or preventing diseases, such as diseases associated with the aberrant, increased, or undesired activity of a kinase, overactivation of the kinase, and/or overexpression of the kinase.

In certain embodiments, the disease (e.g., the disease to be treated or prevented by a method described herein) is associated with the increased activity of a kinase (e.g., SFK (e.g., HCK, LYN, BLK, FRK), Tec Family kinases (e.g., BTK)). In certain embodiments, the disease is associated with overexpression of a kinase (e.g., SFK (e.g., HCK, LYN, BLK, FRK), Tec Family kinases (e.g., BTK)). In certain embodiments, the disease is a proliferative disease. In certain embodiments, the proliferative disease is cancer. In certain embodiments, the cancer is associated with a mutation in MYD88. In another embodiment, the cancer is associated with mutated BTK. In certain embodiments, the proliferative disease is mastocytosis. In certain embodiments, the mastocytosis is systemic mastocytosis. In certain embodiments, the proliferative disease is an IgM gammopathy. In certain embodiments, the IgM gammopathy is IgM monoclonal gammopathy with undetermined significance.

In certain embodiments, the disease is breast cancer. In certain embodiments, the disease is colon cancer. In certain embodiments, the disease is testicular cancer. In certain embodiments, the disease is cancer of the CNS. In certain embodiments, the disease is stomach cancer. In certain embodiments, the disease is lymphoma. In certain embodiments, the lymphoma is B-cell Lymphoma. In certain embodiments, B-cell lymphoma is lymphoplasmacytic lymphoma. In certain embodiments, the lymphoplasmacytic lymphoma is IgM secreting lymphoplasmacytic lymphoma (i.e., Waldenstrom's Macroglobulinemia). In certain embodiments, the disease is Waldenstram's Macroglobulinemia. In certain embodiments, the lymphoplasmacytic lymphoma is non-IgM secreting lymphoplasmacytic lymphoma. In certain embodiments, the lymphoma is Diffuse Large B-Cell Lymphoma (DLBCL). In certain embodiments, the DLBCL is activated B-cell-like (ABC)-DLBCL. In certain embodiments, the DLBCL is germinal center B-cell-like (GBC)-DLBCL. In certain embodiments, the lymphoma is Follicular Lymphoma. In certain embodiments, the lymphoma is marginal zone B-cell lymphoma. In certain embodiments, the lymphoma is Small lymphocytic lymphoma. In certain embodiments, the small lymphocytic lymphoma is Mantle cell lymphoma. In certain embodiments, the cancer is leukemia. In certain embodiments, the leukemia is chronic lymphocytic leukemia (CLL). In certain embodiments, the leukemia is myelogenous leukemia. In certain embodiments, the myelogenous leukemia is chronic myelogenous leukemia. In certain embodiments, the myelogenous leukemia is acute myelogenous leukemia. In certain embodiments, the acute myelogenous leukemia is mast cell leukemia. In certain embodiments, the cancer is myeloma. In certain embodiments, the myeloma is IgM myeloma. In certain embodiments, the IgM myeloma is IgM multiple myeloma. In certain embodiments, the cancer is a myeloproliferative disease. In certain embodiments, the myeloproliferative disease is myelodysplastic syndrome.

In certain embodiments, the method described herein is superior (e.g., showing improved safety and/or therapeutic effects) or comparable to existing therapy (e.g., chemotherapy, treatment with a BTK inhibitor). In certain embodiments, the method described herein is associated with decreased toxicity when compared to existing therapy (e.g., chemotherapy, treatment with a BTK inhibitor).

In certain embodiments, the cell is a malignant cell (e.g., cancer cell). In certain embodiments, the cell is a malignant blood cell. In certain embodiments, the cell is a malignant bone marrow cell. In certain embodiments, the cell is an adenocarcinoma cell, blastoma cell, carcinoma cell, or sarcoma cell. In certain embodiments, the cell is a pre-malignant cell (e.g., pre-cancerous cell).

In certain embodiments, the method described herein further comprises administering to the subject in need thereof an additional therapy. In certain embodiments, the additional therapy is a cytotoxic chemotherapy (e.g., gemcitabine, cytarabine, daunorubicin, doxorubicin, vincristine, 1-asparaginase, cyclophosphamide, or etoposide). In certain embodiments, the additional therapy is an epigenetic modifier (e.g., azacitidine or romidepsin). In certain embodiments, the additional therapy is a glucocorticoid. In certain embodiments, the additional therapy is an immunotherapy (e.g., an immunotherapeutic monoclonal antibody). In some embodiments, the additional pharmaceutical agent is etoposide, obatoclax, or navitoclax, and optionally the disease is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and optionally the disease is Ewing's sarcoma. In some embodiments, the additional pharmaceutical agent is JQ1 or NVP2, and optionally the disease is leukemia, e.g., acute myelogenous leukemia, myeloblastic leukemia, promyelocytic leukemia, myelomonocytic leukemia, monocytic leukemia, monoblastic leukemia, or megakaryoblastic leukemia.

In yet another aspect, the present disclosure provides compounds and pharmaceutical compositions described herein for use in the treatment of a disease (e.g., a proliferative disease, such as an IgM gammopathy, mastocytosis, or cancer) in a subject in need thereof.

In yet another aspect, the present disclosure provides compounds and pharmaceutical compositions described herein for use in the prevention of a disease (e.g., a proliferative disease, such as an IgM gammopathy, mastocytosis, or cancer) in a subject in need thereof.

In another aspect, the present disclosure provides compounds and pharmaceutical compositions described herein for use in inhibiting the activity of a kinase in a subject in need thereof.

In another aspect, the present disclosure provides uses of compounds and pharmaceutical compositions described herein in the manufacture of a medicament for treating a disease in a subject in need thereof.

In another aspect, the present disclosure provides uses of compounds and pharmaceutical compositions described herein in the manufacture of a medicament for preventing a disease in a subject in need thereof.

The compounds, pharmaceutical compositions, and kits described herein may synergistically augment inhibition of a kinase (e.g., SFK (e.g., HCK, LYN, BLK, FRK), a TEC family kinase (e.g., BTK)) induced by the additional pharmaceutical agent(s) in the subject. Thus, the combination of the compounds, pharmaceutical compositions, or kits with additional pharmaceutical agent(s) may be useful in treating diseases resistant to a treatment using the additional pharmaceutical agent(s) without the compounds, pharmaceutical compositions, or kits described herein.

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1. Compound (I) Selectively Targets HCK and BTK in MYD88 Mutated WM and ABC DLBCL Cells FIG. 2 shows the KINOMEscan®, the biochemical kinase assay for determination of kinome compound potency and selectivity, profiles of Compound (I) and A419259. The compounds were profiled at a concentration of 1.0 μM against a panel of over 460 kinases by DiscoverX. Compound (I) and A419259 have almost identical selectivity with S(10) score of 0.13 and S(1) score of 0.07. Enzymatic assays were also performed for potential targets HCK, BTK, LYN (SelectScreen, Life Technologies), which demonstrated that Compound (I) exhibited potent inhibition of HCK, BTK and LYN with single-digit nanomolar IC50s, while A419259 was 10 times less potent on BTK.

Figure 2B:
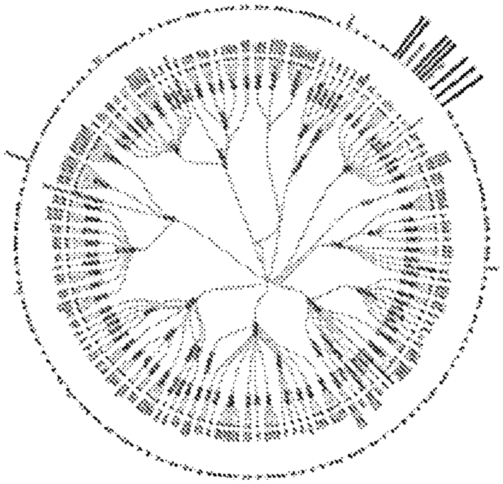
FIG. 2B shows a KiNativ™ (a biochemical kinase profiling assay) cellular target engagement profile for Compound (I). Kinases engaged over 50% with 1.0 μM Compound (I) treatment in TMD8 cells are listed.
Figure 2C:
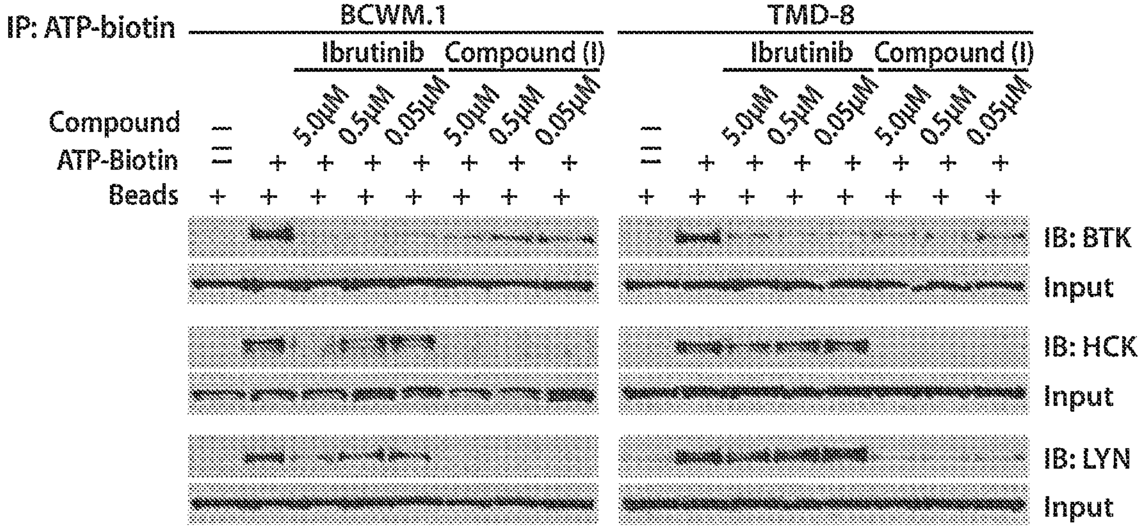
FIG. 2C shows activated kinases enriched by pulldown assay using Desthiobiotin-ATP Probe following BCWM.1 and TMD8 live cells pre-treated with Compound (I) or ibrutinib at indicated concentrations for 90 minutes and the ATP-binding HCK, BTK and LYN were resolved by western blotting.

Biochemical kinase assays demonstrated that Compound (I) strongly inhibited HCK ($IC_{50}$<0.495 nM) and BTK ($IC_{50}$=0.915 nM). By comparison, ibrutinib exhibited similar BTK inhibition ($IC_{50}$=0.614 nM), and 100-fold less potent HCK inhibition ($IC_{50}$=49 nM). To assess the kinase target selectivity of Compound (I), a KINOMEscan®, the biochemical kinase assay for determination of kinome compound potency and selectivity, against a panel of 464 kinases was performed. Compound (I) showed highly selective activity (S10=0.07; S35=0.13) that were comparable to the selectivity of ibrutinib (S10=0.04; S35=0.12). Compound (I) targeted kinases were mainly limited to the Src-family kinases HCK, BLK, LYN, and FRK, and the Tec-family kinase BTK (FIG. 2A). To further evaluate the kinome selectivity of Compound (I) and verify its target engagement in live-cells, KiNativ™ (a biochemical kinase profiling assay) profiling was performed that measured the ability of Compound (I) to block binding of kinases to a desthiobiotin-ATP Probe. KiNativ™ (a biochemical kinase profiling assay) screening confirmed that Compound (I) strongly targeted both HCK and BTK in TMD8 ABC DLBCL cells treated at 1. μM. These experiments show that Compound (I) also has nanomolar activity against SRC-family kinases (e.g., HCK, BLK, LYN, FRK), Tec-family kinases (e.g., BTK), ACK family kinases (e.g., ACK (i.e., TNK2)), CSK, ErbB2, and ABL (FIG. 2B). To further confirm HCK and BTK targeting by Compound (I), an ATP-Competitive Assay was also performed using Pierce™ Kinase Enrichment Kit with ActivX desthiobiotin-ATP Probe following live cell pre-treatment with Compound (I) in MYD88 mutated BCWM.1 WM cells and TMD8 ABC DLBCL cells. The enriched kinases were resolved by western blots and showed robust engagement of Compound (I) to HCK, as well as a similar level of BTK inhibition as ibrutinib (FIG. 2C). Compound (I) effectively binds to BTK and very strongly binds to HCK and LYN in live BCWM.1 and TMD8 cells.

Example 2. Inhibition of HCK and BTK by Compound (I)

Figure 3A:
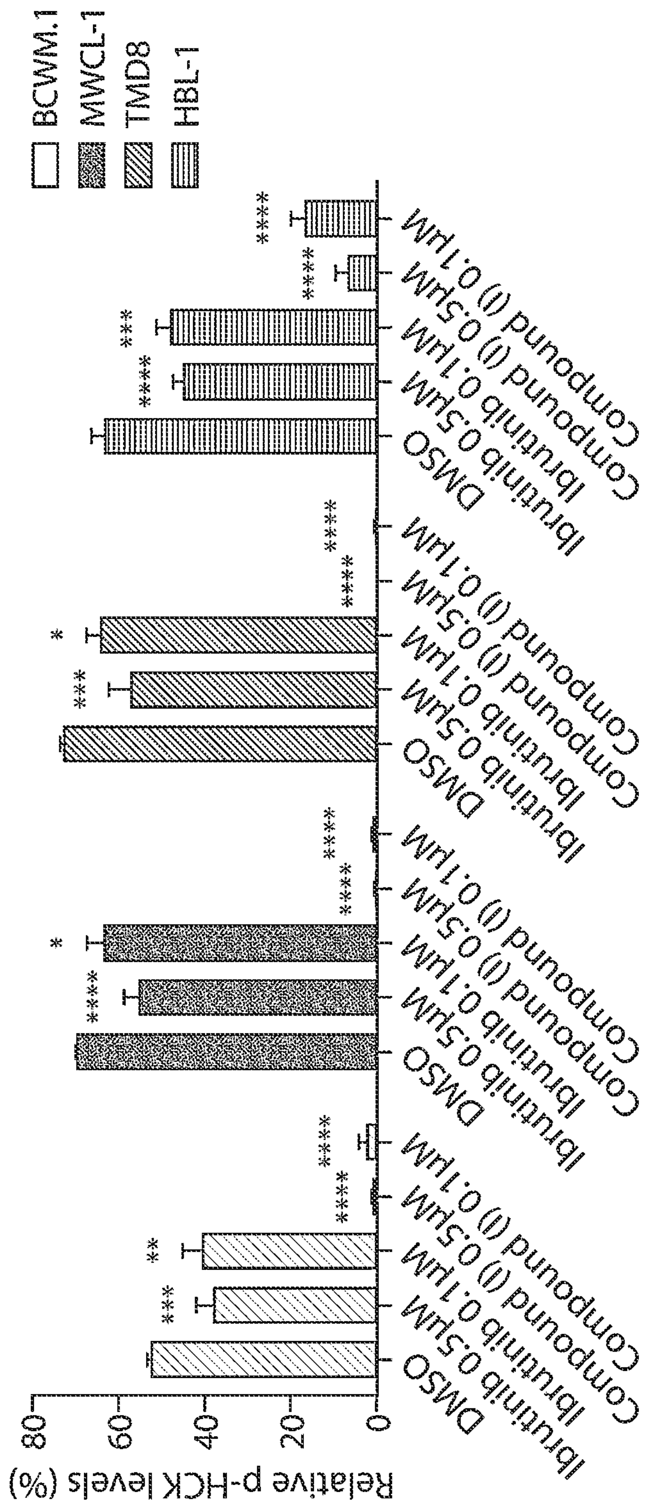
FIG. 3 shows the impact of Compound (I) and ibrutinib on HCK phosphorylation by PhosFlow™, an intracellular stain for post-translationally modified signaling proteins, analysis (N=3) (FIG. 3A) and BTK phosphorylation by western blotting (FIG. 3B) in MYD88 mutated WM (BCWM.1, MWCL-1) and ABC DLBCL (TMD8, HBL-1) cell lines; as well as HCK and BTK phosphorylation by PhosFlow™, an intracellular stain for post-translationally modified signaling proteins, analysis in MYD88 mutated WM patient bone marrow tumor cells (N=4) (FIG. 3C).
Figure 3B:
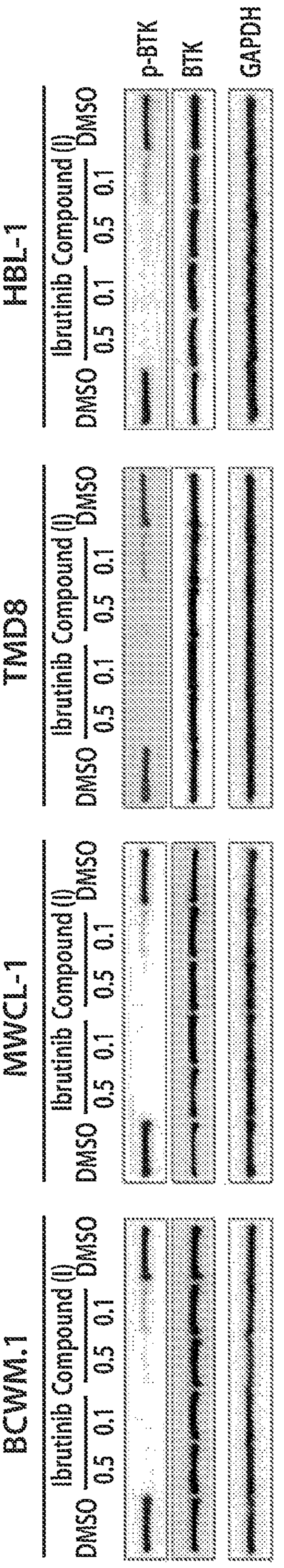
Figure 3C:
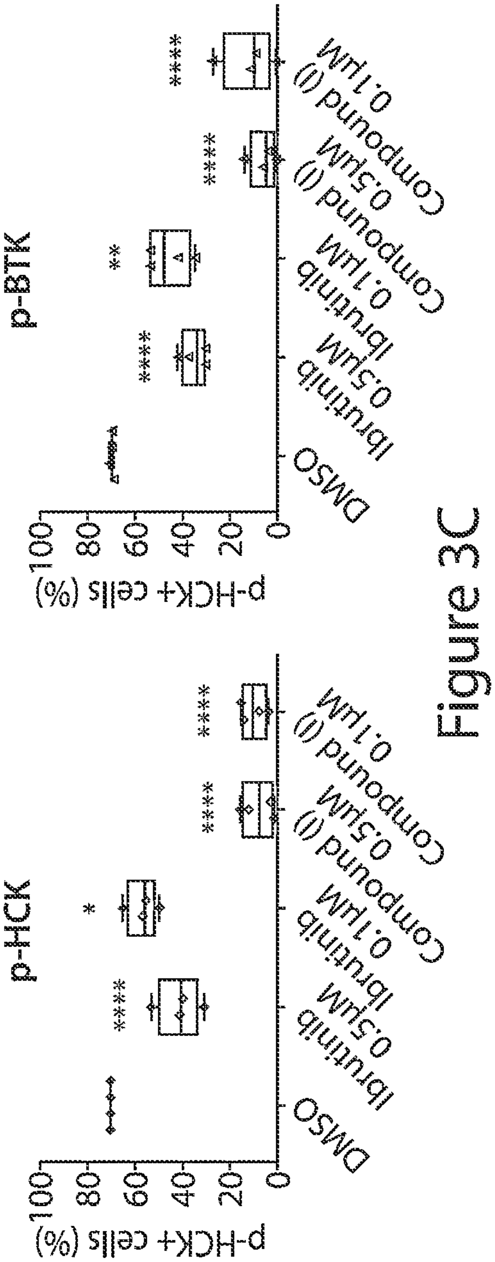

The inhibition of HCK and BTK by Compound (I) was assessed by changes in phosphorylation levels of HCK at known sites of functionality, i.e., $Thr^{209}$ on HCK by PhosFlow™ (an intracellular stain for post-translationally modified signaling proteins); and $BTK^{Tyr223}$ by western blotting in MYD88 mutated WM and ABC DLBCL cells. Comparisons were made to ibrutinib for both HCK and BTK and the findings showed that ibrutinib modestly inhibited HCK phosphorylation, while Compound (I) showed robust inhibition of HCK phosphorylation at $Thr^{209}$ (FIG. 3A). A similar level for inhibition of BTK at $Tyr^{223}$ was observed for ibrutinib and Compound (I) (FIG. 3B). The impact of Compound (I) and ibrutinib was also determined on HCK and BTK phosphorylation by PhosFlow™ (an intracellular stain for post-translationally modified signaling proteins) analysis in MYD88 mutated WM patient bone marrow tumor cells in the presence of bone marrow microenvironment mononuclear cells (N=4) (FIG. 3C). Whole bone marrow mononuclear cells were treated with ibrutinib, A419259, or Compound (I) at indicated concentrations for 2.0 hours and fixed with BD PhosFlow™ (an intracellular stain for post-translationally modified signaling proteins) Fix Buffer I (BD biosciences) for 10 minutes at 37° C., permeabilized with BD Perm/Wash™ Buffer I (BD biosciences), then stained with mouse anti-human CD20 (APC-cy7) specific antibody (BD biosciences) together with rabbit anti-human p-HCK specific antibody followed by Donkey anti-Rabbit IgG (Alexa Fluor® 647, a bright, far-red-fluorescent dye) secondary antibody, or PE labeled p-BTK antibody. p-HCK or p-BTK levels were analyzed on $CD20^+$ LPCs population.

Example 3. Cellular Efficacies of Compound (I) in MYD88 Wild Type (MYD88WT) and MYD88 Mutated (MYD88L265P) B-Cell Lymphoma Cells The anti-tumor effects of Compound (I) were also evaluated in MYD88 mutated WM and ABC DLBCL cell lines, as well as MYD88 wild-type GCB DLBCL, Burkitt's Lymphoma, and multiple myeloma cell lines. Compound (I) showed targeted anti-tumor activity against MYD88 mutated versus wild-type cell lines (FIG. 28A). The anti-tumor activity of Compound (I) was also assessed using primary MYD88 mutated bone marrow derived CD19-positive lymphoplasmacytic cells (LPCs) from WM patients, and compared effects against healthy donor CD19+

Figure 4A:
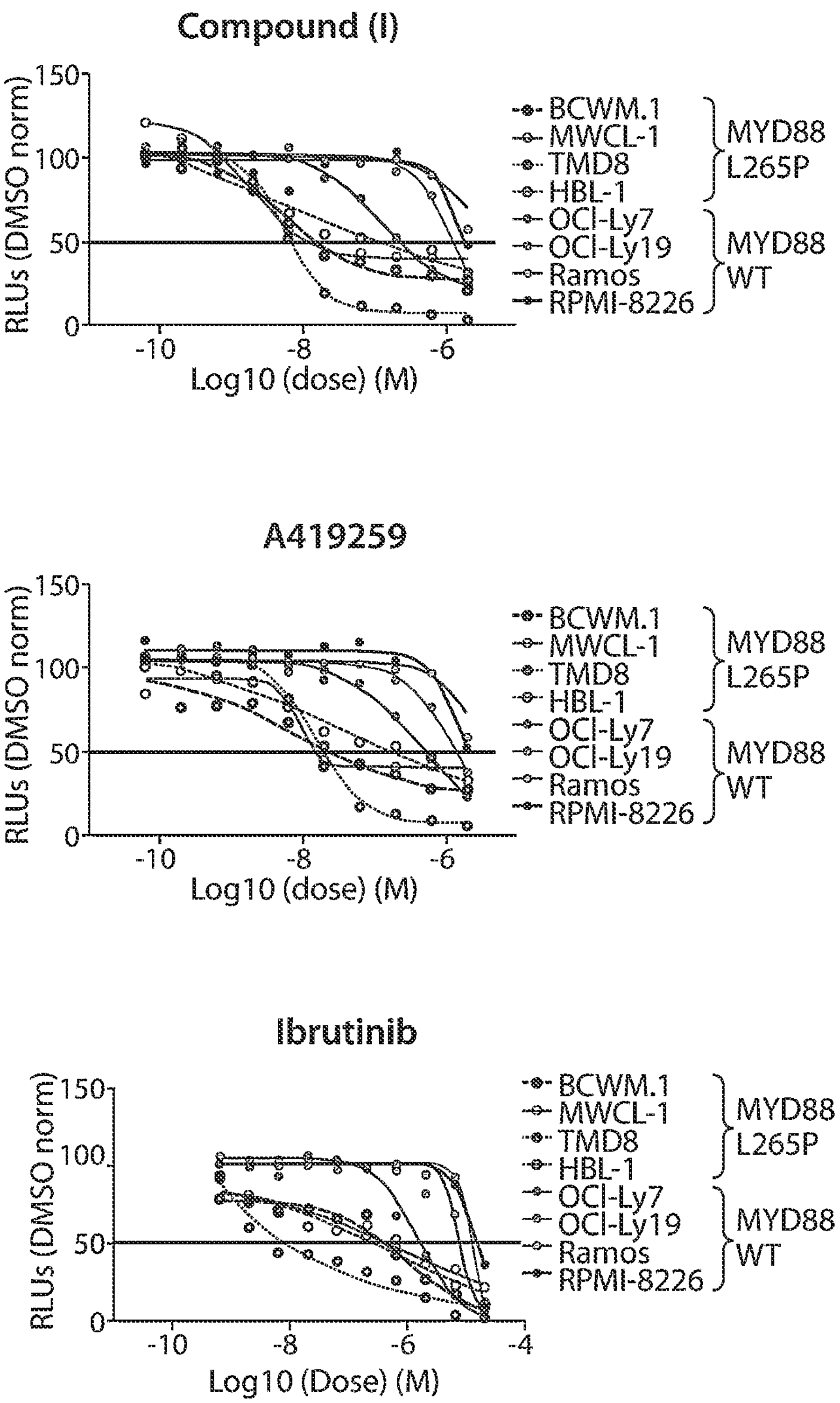
(FIG. 4A). Apoptotic activity for primary BM lymphoplasmacytic cells from 6 MYD88 mutated patients and 6 healthy donor CD19+ B-cells following ibrutinib or Compound (I) treatment at indicated concentrations for 16 hours. *$p<0.05$;  $p<0.01$; **$p<0.0001$.
Figure 4B:
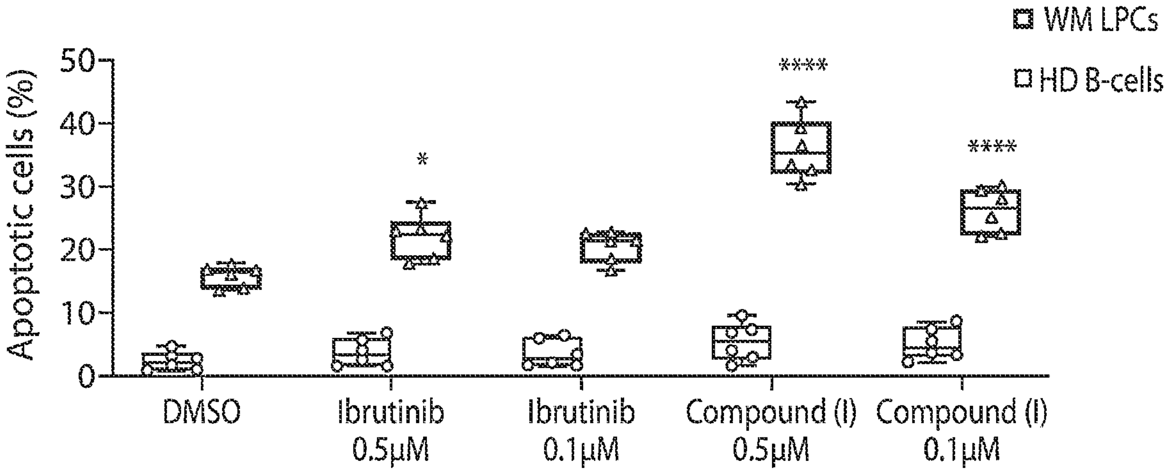
FIG. 4 shows cellular efficacies of Compound (I) in MYD88 wild type ($MYD88^{WT}$) and MYD88 mutated ($MYD88^{L265P}$) B-cell lymphoma cells. Dose-responses of $MYD88^{WT}$ and $MYD88^{L265P}$ cell lines following treatment with serially diluted Compound (I), A419259 and Ibrutinib for 72 hours.

B-cells. The activity of Compound (I) was compared to ibrutinib in these experiments. While ibrutinib showed modest apoptotic effect against primary LPCs, Compound (I) produced robust apoptosis of MYD88 mutated WM patient LPCs (FIG. 4B). Compound (I) showed no apoptotic effect against healthy donor CD19+ B-cells (FIG. 4B). The anti-apoptotic effect by Compound (I) corresponded to a reduction of p-HCK(T209) and p-$BTK^{Y223}$ in WM patients LPCs by PhosFlow™ (an intracellular stain for post-translationally modified signaling proteins) analysis (FIG. 3C).

In vitro cellular efficacies (drug dose-response) were measured by CellTiter-Glo™ a luminescent cell viability assay based on ATP detection, to indicate cell viability in MYD88 mutated or wild type B-cell lymphoma or multiple myeloma cell lines under the treatment of series diluted Compound (I) or A419259 for 72 hours. Blue line across Y axes at 50 indicates EC50 levels for each cell line at corresponding drug concentration of X axes (FIG. 4A).

Figure 5A:
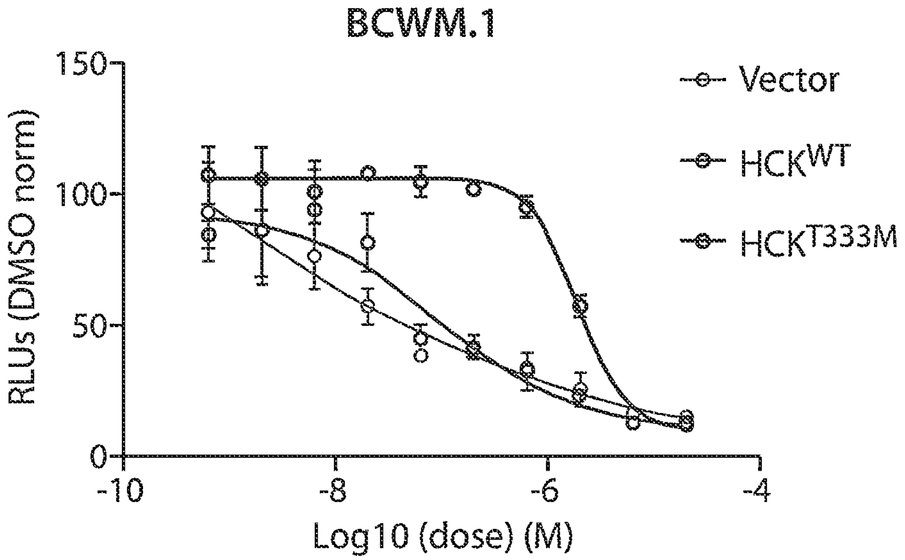
FIG. 5A shows dose-responses of vector only or $HCK^{WT}$ or $HCK^{T333M}$ transduced BCWM.1 cells following the treatment Compound (I) for 72 hours.
Figure 5B:
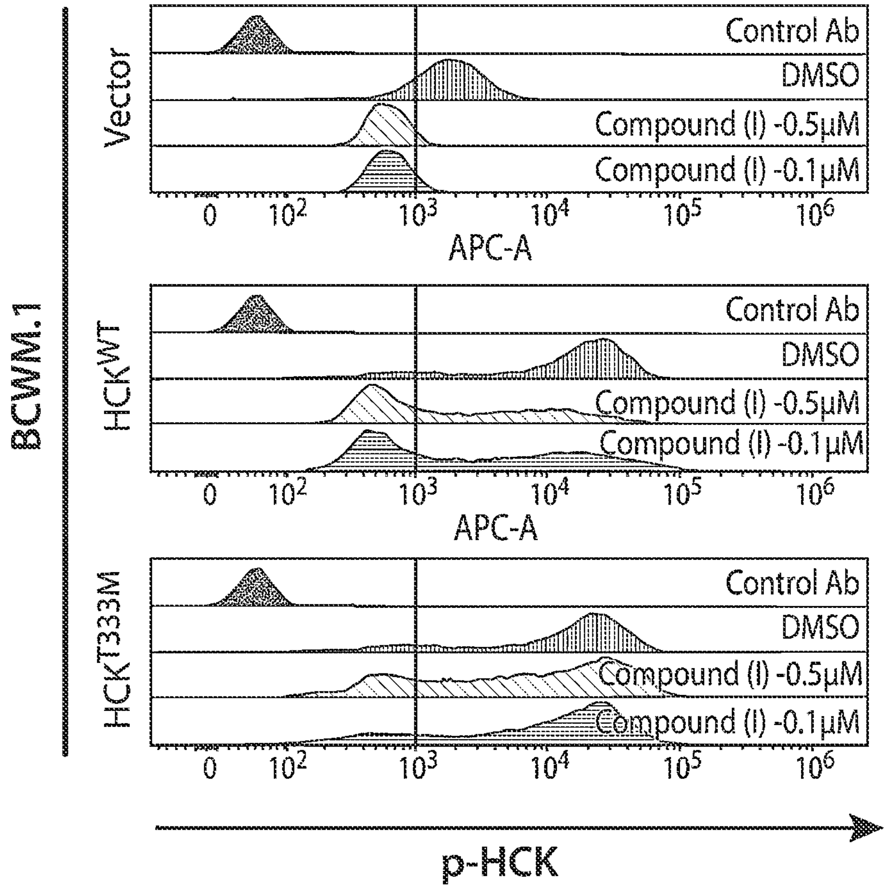
FIG. 5B shows relative $pHCK^{Y411}$ levels resolved by PhosFlow™ (an intracellular stain for post-translationally modified signaling proteins) analysis following the treatment of Compound (I) at indicated concentrations for 1.0 hour in vector only, $HCK^{WT}$ or $HCK^{T333M}$ transduced MYD88 mutated BCWM.1 cells.
Figure 5C:
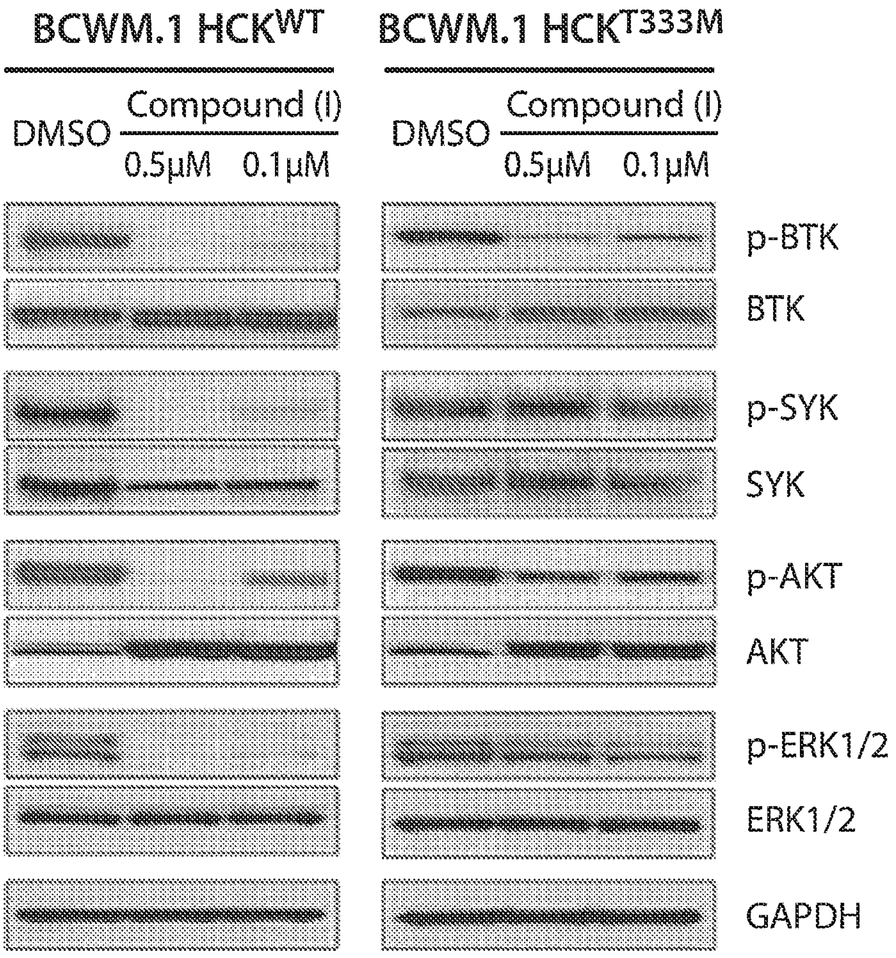
FIG. 5C shows $pBTK^{Y223}$, $pSYK^{Y525/526}$, $p\text{-}AKT^{S473}$, $p\text{-}ERK1/2^{T202/Y204}$ expression by western blot analysis in $HCK^{WT}$ or $HCK^{T333M}$ transduced BCWM.1 cells following treatment with Compound (I) at indicated concentrations for 1.0 hour. The expression levels of total BTK, SYK, AKT and ERK1/2 in these cells as well as protein loading control GAPDH are also shown.

Example 4. Compound (I) Resistance to the $HCKT^{333}M$ Gatekeeper Mutant Demonstrates that HCK is a Key Target of Compound (I) in MYD88 Mutated WM Cells An HCK gatekeeper mutant $HCK^{T333M}$ was generated and rescue experiments performed in MYD88 mutated BCWM.1 cells. Expression of $HCK^{T333M}$ produced a more than 20-fold increase in resistance to Compound (I) versus vector or wild-type HCK transduced BCWM.1 cells (FIG. 5A). In addition, the expression of $HCK^{T333M}$ but not $HCK^{WT}$ led to persistent activation of HCK in the presence of Compound (I) (FIG. 5B). BCWM.1 cells expressing $HCK^{WT}$ or $HCK^{T333M}$ were also evaluated with Compound (I), and it was found that the activation state included BTK, AKT, ERK1/2, and SYK. Compound (I) blocked the expression of pBTK, pAKT, pERK1/2, and p-SYK in a dose dependent manner in $HCK^{WT}$ expressing cells (FIG. 5C). Conversely, attenuation of pBTK, pAKT, pERK1/2, and pSYK was abrogated in $HCK^{T333M}$ expressing BCWM.1 cells. pBTK continued to show reduced activity by Compound (I) in $HCK^{T333M}$ expressing BCWM.1 cells consistent with its role as a direct inhibitor of BTK activity (FIG. 5C). Taken together, the above data show that HCK and BTK are on target and have biologically important sequelae in response to Compound (I) activity, including inhibition of multiple downstream pro-survival signaling pathways related to HCK and BTK.

Figure 6A:
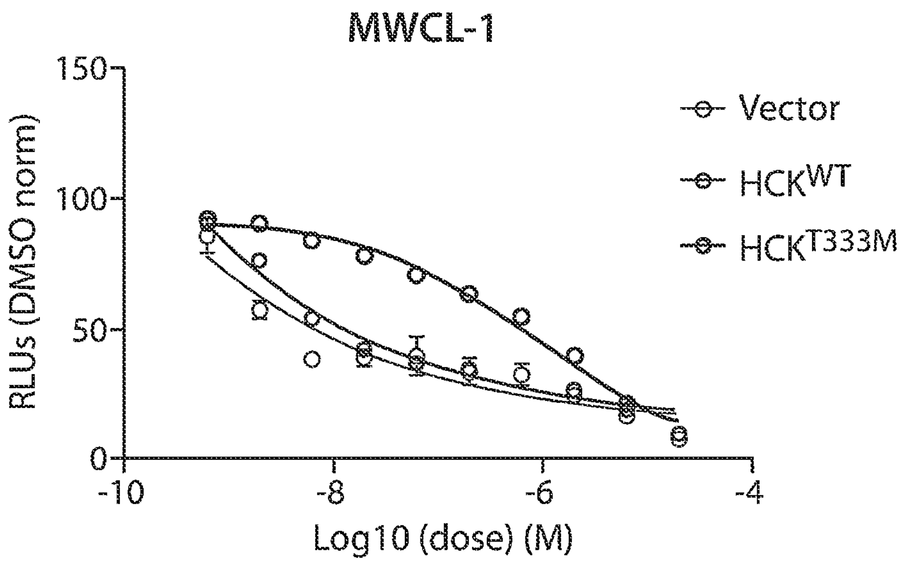
FIG. 6A shows dose-responses of vector only or $HCK^{WT}$ or $HCK^{T333M}$transduced BCWM.1 cells following the treatment Compound (I) for 72 hours.
Figure 6B:
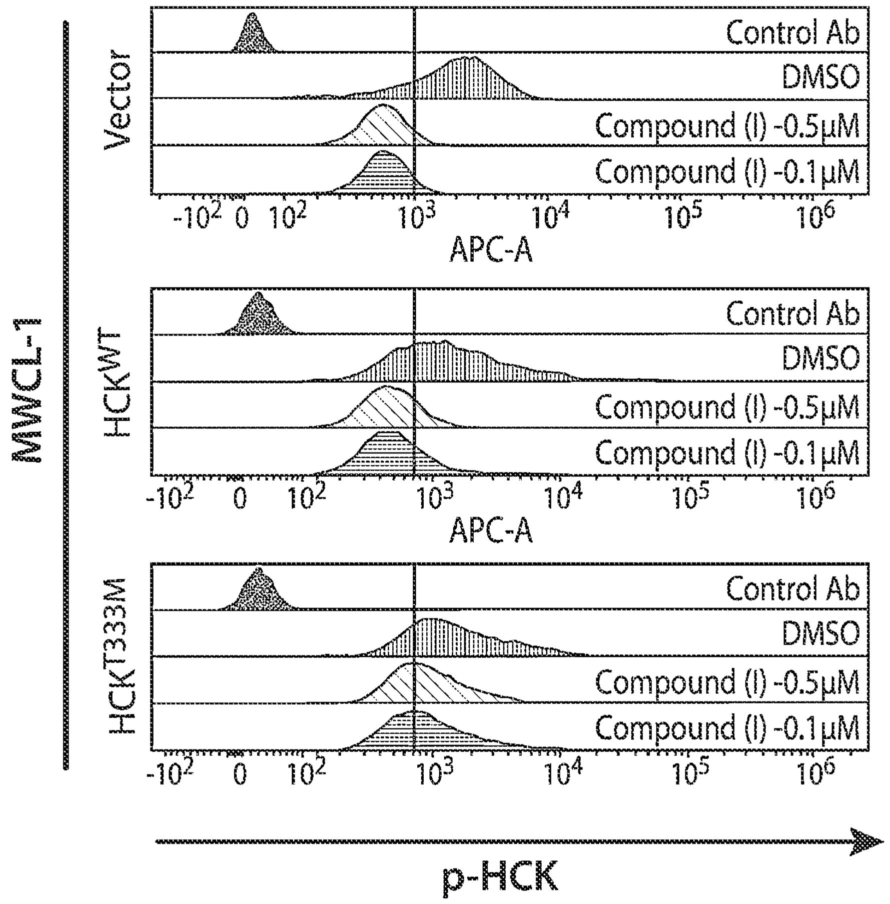
FIG. 6B shows relative $pHCK^{1411}$ levels resolved by PhosFlow™ (an intracellular stain for post-translationally modified signaling proteins) analysis following the treatment of Compound (I) at indicated concentrations for 1.0 hour in vector only, $HCK^{WT}$ or $HCK^{T333M}$ transduced MYD88 mutated BCWM.1 cells.
Figure 6C:
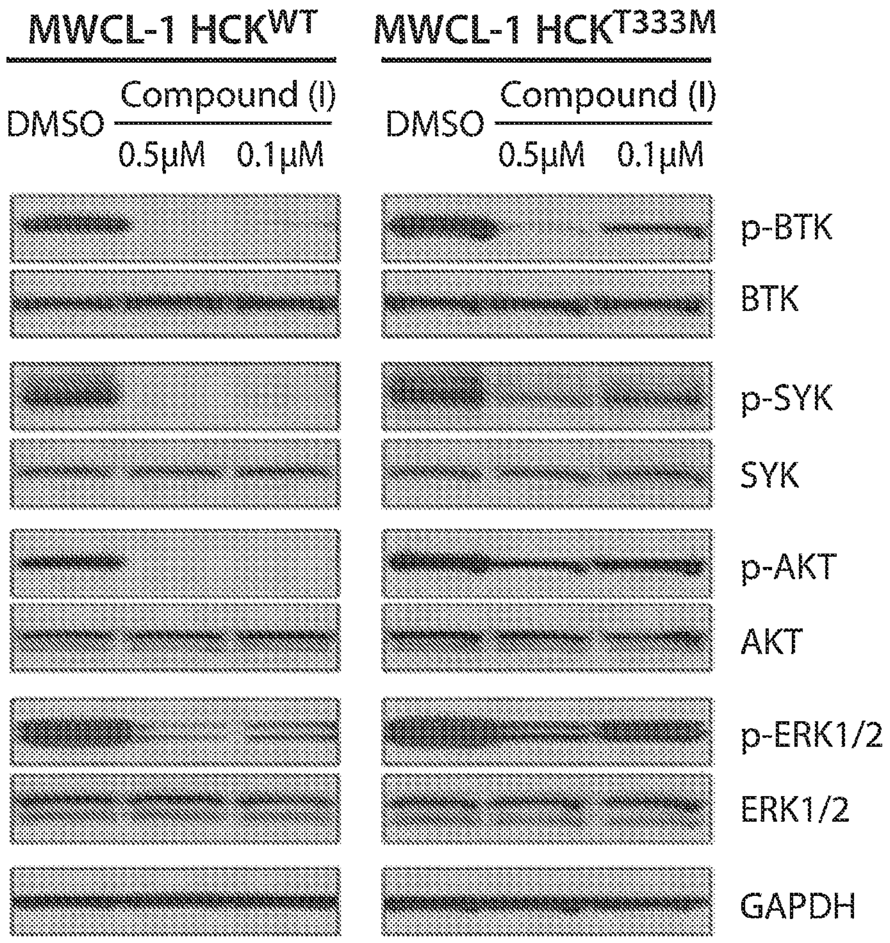
FIG. 6C shows $pBTK^{Y223}$, $pSYK^{Y525/526}$, $p\text{-}AKT^{S473}$, $p\text{-}ERK1/2^{T202/Y204}$ expression by western blot analysis in $HCK^{WT}$ or $HCK^{T333M}$ transduced BCWM.1 cells following treatment with Compound (I) at indicated concentrations for 1.0 hour. The expression levels of total BTK, SYK, AKT and ERK1/2 in these cells as well as protein loading control GAPDH are also shown.

FIG. 6 shows HCK gatekeeper mutant ($HCK^{T333M}$) rescues Compound (I) induced cell death and blocks HCK activation and its downstream signaling in MWCL-1 WM cells. Dose-responses of vector only or $HCK^{WT}$ or $HCK^{T333M}$ transduced MWCL-1 cells following the treatment Compound (I) for 72 hours (FIG. 6A). Relative $pHCK^{Y411}$ levels resolved by PhosFlow™ (an intracellular stain for post-translationally modified signaling proteins) analysis following the treatment of Compound (I) at indicated concentrations for 1.0 hour in vector only, $HCK^{WT}$ or $HCK^{T333M}$ transduced MYD88 mutated BCWM.1 cells (FIG. 6B). $pBTK^{Y223}$, $pSYK^{Y525/526}$, p-$AKT^{S473}$, p-ERK1/$2^{T202/Y204}$ expression by western blot analysis in $HCK^{WT}$ or $HCK^{T333M}$ transduced BCWM.1 cells following treatment with Compound (I) at indicated concentrations for 1.0 hour (FIG. 6C). The expression levels of total BTK, SYK, AKT and ERK1/2 in these cells as well as protein loading control GAPDH are also shown.

Figure 7A:
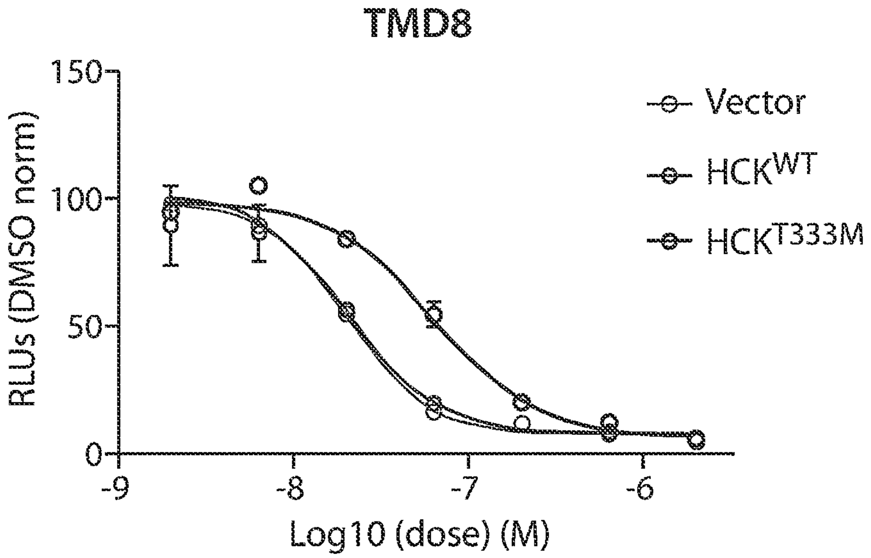
FIG. 7A shows dose-responses of vector only or $HCK^{WT}$ or $HCK^{T333M}$ transduced BCWM.1 cells following the treatment Compound (I) for 72 hours.
Figure 7B:
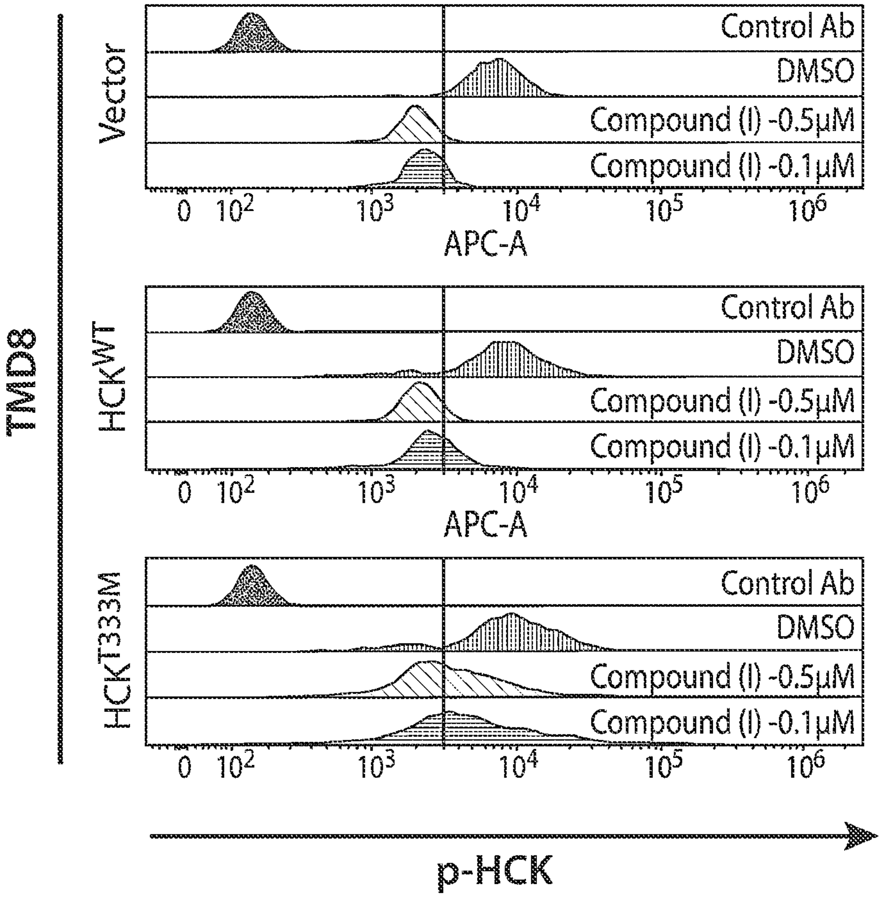
FIG. 7B shows relative $pHCK^{Y411}$ levels resolved by PhosFlow™ (an intracellular stain for post-translationally modified signaling proteins) analysis following the treatment of Compound (I) at indicated concentrations for 1.0 hour in vector only, $HCK^{WT}$ or $HCK^{T333M}$ transduced MYD88 mutated BCWM.1 cells.
Figure 7C:
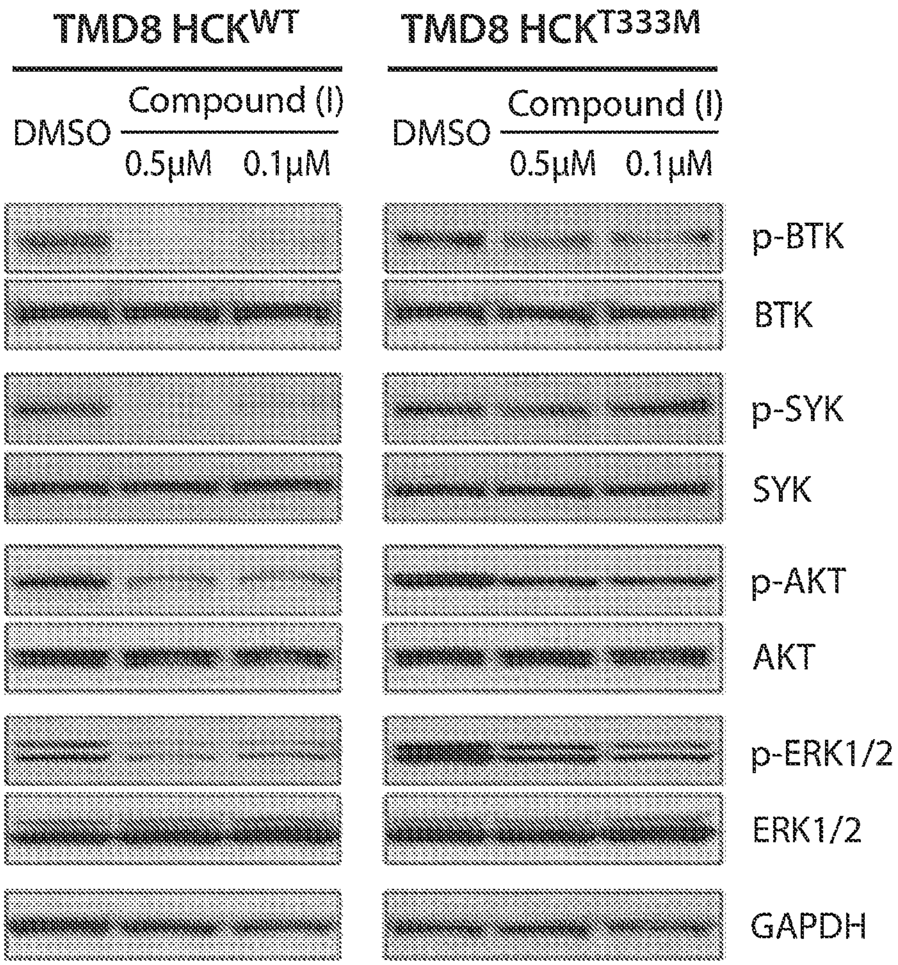
FIG. 7C shows $pBTK^{Y223}$, $pSYK^{Y525/526}$, $p\text{-}AKT^{S473}$, $p\text{-}ERK1/2^{T202/Y204}$ expression by western blot analysis in $HCK^{WT}$ or $HCK^{T333M}$ transduced BCWM.1 cells following treatment with Compound (I) at indicated concentrations for 1.0 hour. The expression levels of total BTK, SYK, AKT and ERK1/2 in these cells as well as protein loading control GAPDH are also shown.

FIG. 7 shows HCK gatekeeper mutant ($HCK^{T333M}$) rescues Compound (I) induced cell death and blocks HCK activation and its downstream signaling in TMD8 ABC DLBCL cells. Dose-responses of vector only or $HCK^{WT}$ or $HCK^{T333M}$ transduced TMD7 cells following the treatment Compound (I) for 72 hours (FIG. 7A). Relative $pHCK^{Y411}$ levels resolved by PhosFlow™ (an intracellular stain for post-translationally modified signaling proteins) analysis following the treatment of Compound (I) at indicated concentrations for 1.0 hour in vector only, $HCK^{WT}$ or $HCK^{T333M}$ transduced MYD88 mutated BCWM.1 cells (FIG. 7B). $pBTK^{Y223}$, $pSYK^{Y525/526}$, p-$AKT^{S473}$, p-ERK1/$2^{T202/Y204}$ expression by western blot analysis in $HCK^{WT}$ or $HCK^{T333M}$ transduced BCWM.1 cells following treatment with Compound (I) at indicated concentrations for 1.0 hour (FIG. 7C). The expression levels of total BTK, SYK, AKT and ERK1/2 in these cells as well as protein loading control GAPDH are also shown.

Example 5. In Vitro and In Vivo Profile of Pharmacokinetics Properties of Compound (I)

FIG. 8 shows Compound (I) was further profiled for in vitro and in vivo pharmacokinetics properties. Incubation in liver microsomes showed excellent stability ($T_{1/2}$ around or longer than 60 minutes) across multiple species including human, mouse, and rat. Incubation in liver microsomes showed excellent stability ($T_{1/2}$ around or longer than 60 minutes) across multiple species including human, mouse and rat. Murine pharmacokinetic parameters are shown for Compound (I) following 2 mg/kg intravenous, and 10 mg/kg and 25 mg/kg administration. Consistent with the long microsomal stability for Compound (I), mouse pharmacokinetic studies showed bioavailability of 49% to 55% following 10 mg/kg and 25 mg/kg oral administration, respectively. The serum half-life was 11.5 hours following intravenous administration, and 15.1 and 16.9 hours following 10 mg/kg and 25 mg/kg oral administration, respectively. In vitro metabolism studies for CYP inhibition (% at 10 PM) were as follows: −27.9 (1A), 64.5 (2B6), −3.8 ($2C_8$), −10.9 ($2C_9$), 0.8 ($2C_{19}$), 24.9 (2D6), −22.7/−4.9 (3A). Ames genotoxicity testing was negative for four *Salmonella typhimurium* tester strains (TA98, TA100, TA1535 and TA1537) up to 50 μM with and without metabolic activation by rat liver S9 fraction. hERG testing (patch clamp) for cardiotoxicity was negative at 16 μM. Tolerability studies showed that Compound (I) was well-tolerated up to 75 mg/kg daily oral dosing with no adverse events observed in NOD-SCID mice dosed for >6 weeks. Plasma protein binding showed comparable levels across species as follows: mice (97.7%); rats (95.5%); dogs (95.0%); and humans (95.7%).

Consistent with the observed low rate of metabolism in the microsomal assays, Compound (I) affords low in vivo clearance rate in mouse of 17.4 mL $min^{-1}$ $kg^{-1}$. When administered orally at 10 mg/kg and 25 mg/kg, Compound (I) is well absorbed with excellent exposures (AUC=5.2, 11.4 μM h, respectively), high bioavailability (% F=55% and 49%, respectively), and ideal drug clearance ($T_{1/2}$=15.1-16.9 hrs).

Figure 9:
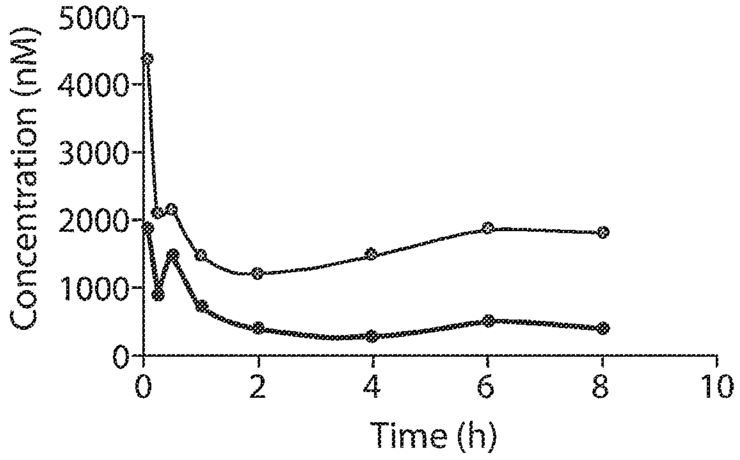
FIG. 9 shows the in vitro and in vivo pharmacokinetics properties of A419259.
Figure 10A:
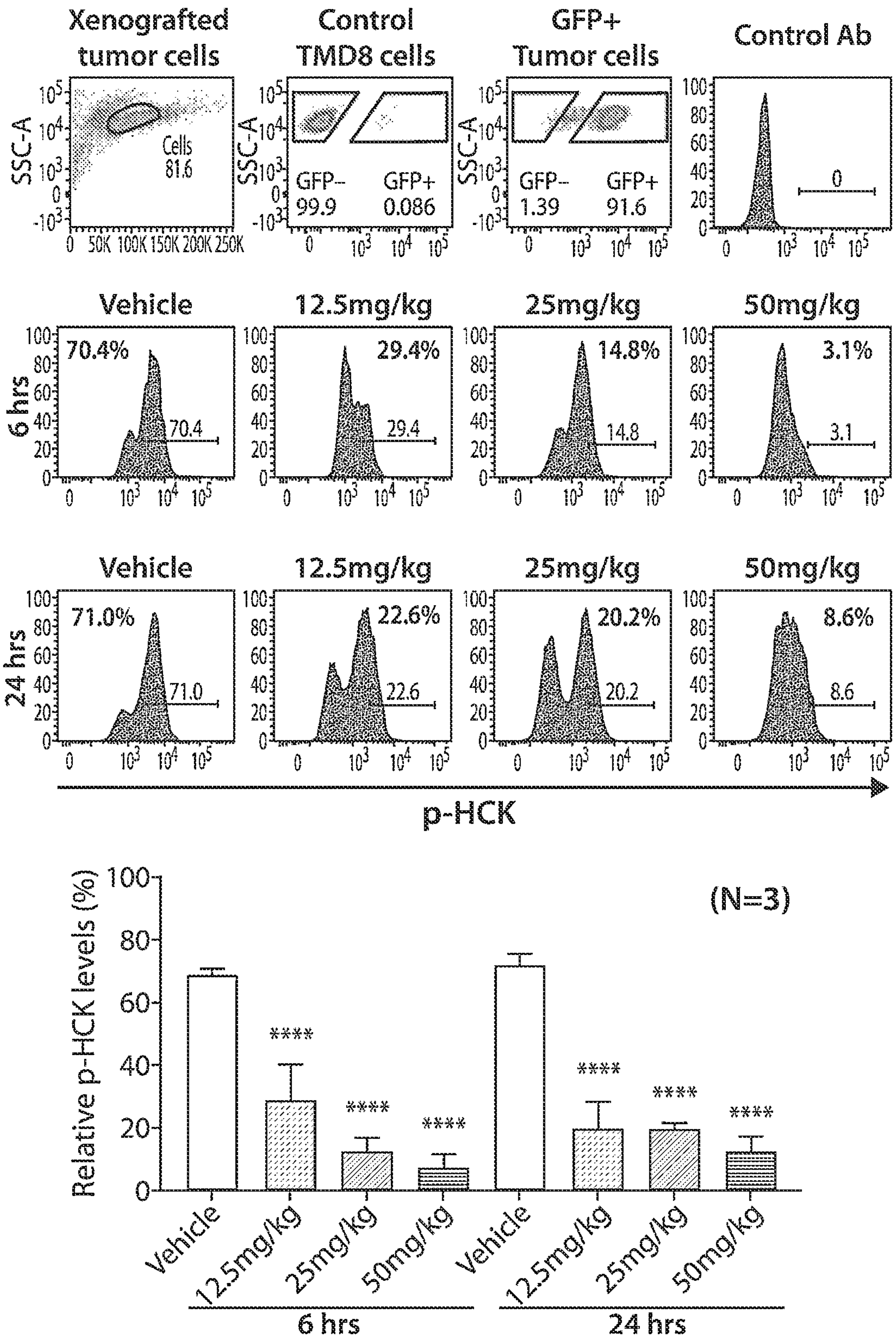
FIG. 10 shows pharmacodynamic studies showing the activity of HCK and BTK following oral administration of Compound (I) in NOD-SCID mice subcutaneously xenografted with ibrutinib sensitive $BTK^{WT}$ TMD8 ABC-DLBCL cells. PhosFlow™ (an intracellular stain for post-translationally modified signaling proteins) plots for $pHCK^{Y411}$ (FIG. 10A) and $pBTK^{Y223}$ (FIG. 10B) in GFP+ TMD8 tumor cells excised at 6 and 24 hours following oral administration of Compound (I) at the indicated doses (n=3 per group). ****p<0.0001.
Figure 10B:
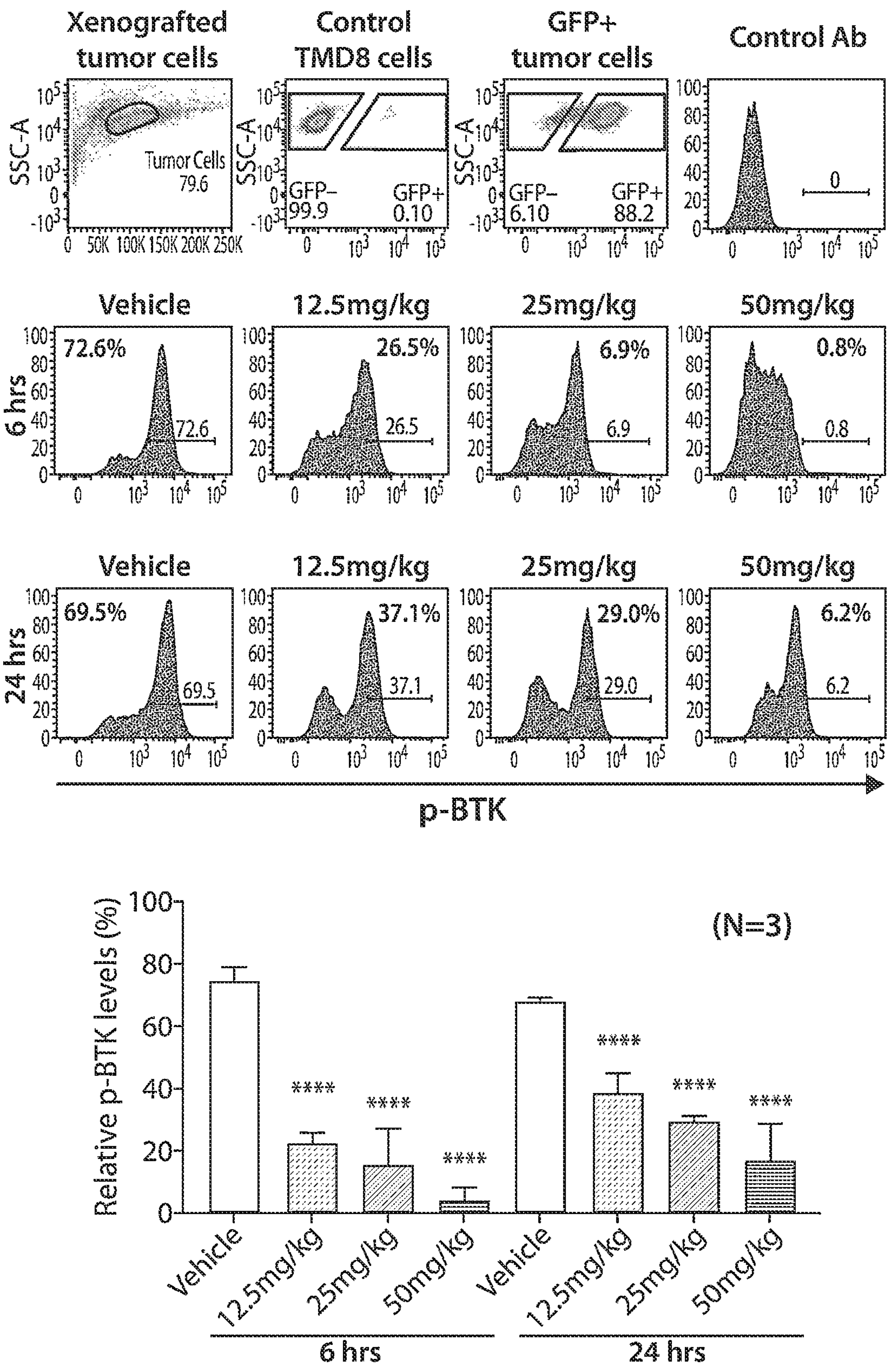

When incubated with purified microsomes, Compound (I) exhibited a half-life of $t_{1/2}$=106.4 mins (mice), $t_{1/2}$=>120 mins (rats), $t_{1/2}$=60 mins (dogs), and $t_{1/2}$=49.5 mins (humans). In contrast, A419259 has an extremely long $Tui_2$ (176.0 hours) under oral administration (FIG. 9), which may be pose a problem for clinical development.

Example 6. Mean Tumor Volume Curves and Survival Curves for NOD-SCID Mice Implanted with Wild Type BTK Expressing TMD8 ABC DLBCL Tumor Cells Treated with Ibrutinib, A419259, or Compound (I)

Figure 11A:
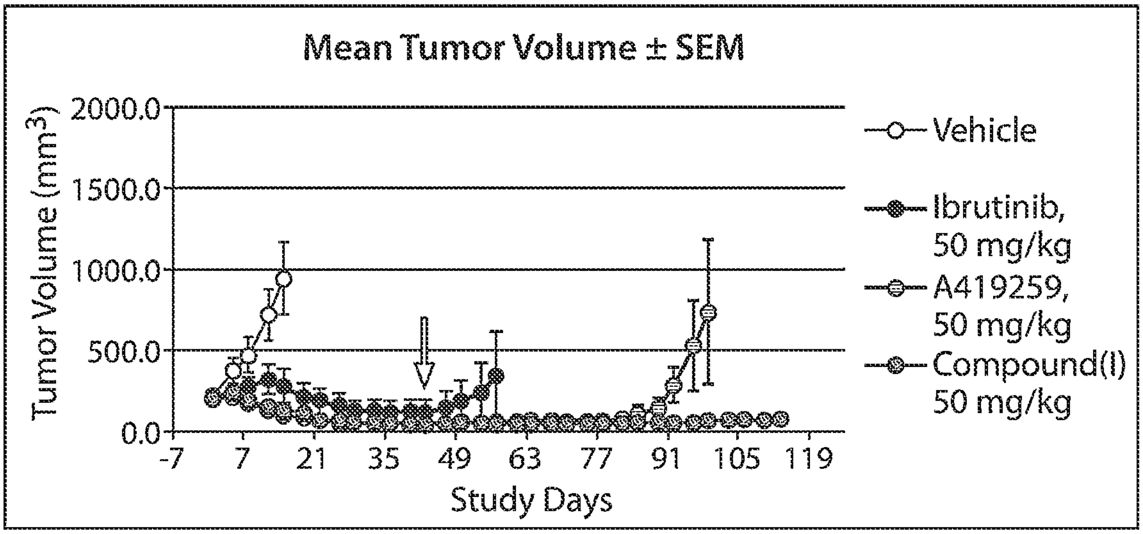
FIG. 11 shows the impact of Compound (I) on tumor volume and survival in $BTK^{WT}$ TMD8 ABC DLBCL xenograft mouse model. Efficacy studies in NOD-SCID mice (n=8 per cohort) bearing ibrutinib sensitive $BTK^{WT}$ TMD8 cells following daily oral administration of vehicle control, ibrutinib or Compound (I) at 50 mg/kg. Tumor volume (mm3) was measured twice weekly and reported as the mean volume ±SEM. Treatment was stopped (indicated by green arrow) at day 42 and tumor volumes were monitored until day 113 (FIG. 11A). Tumor volume comparisons at day 33. p-values for cohort comparisons are shown (FIG. 11B). Survival curve estimations using the Kaplan-Meier method. The median survival (days) for cohorts are shown using Prism software. P<0.0001 for Log-rank comparisons between cohorts (FIG. 11C).
Figure 11B:
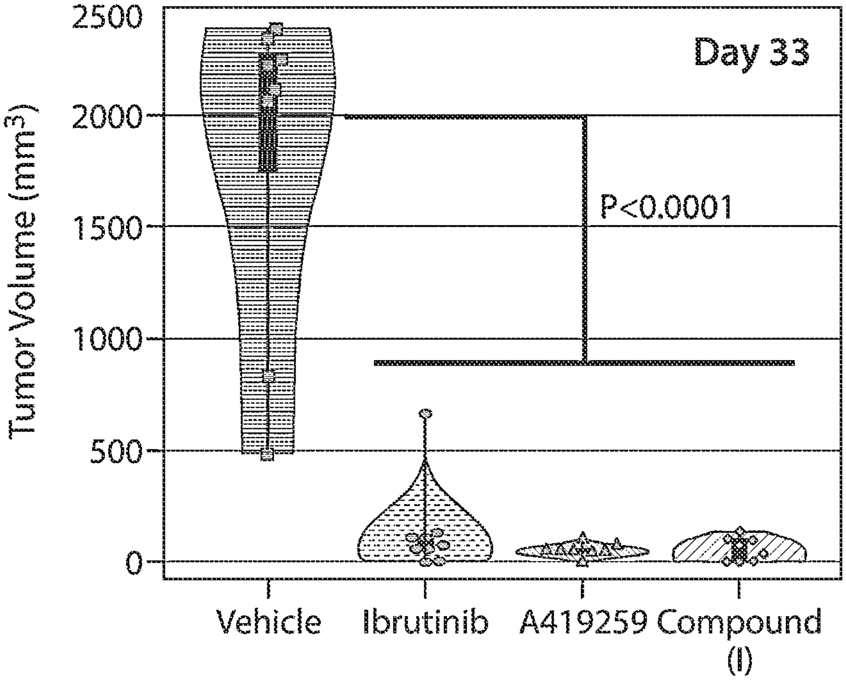
Figure 11C:
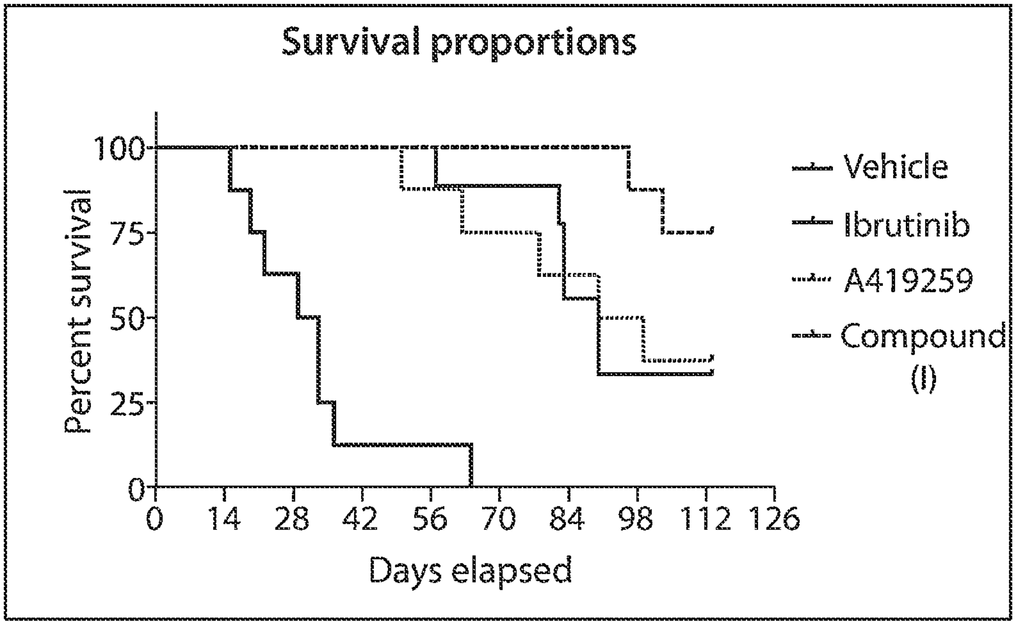

FIG. 11 shows mean tumor volume curves (FIG. 11A), tumor volume statistics at day 33 (FIG. 11B) and survival curves (FIG. 11C). TMD8 tumor cells were implanted into NOD-SCID mice subcutaneously with 8 mice per cohort. After tumors established and reached to ~200 cubic millimeters, mice were treated p.o. on a once daily schedule with either vehicle control or ibrutinib or A419259 or Compound (I) at the concentration indicated. Tumors were measured twice a week with electronic calipers (FIG. 11A). Tumor volumes in all treated groups were significantly smaller than tumor volumes in mice that received a vehicle control at day 33 (P<0.005, by "Wilcoxon Rank Sum Test" and P<0.0001, by "Tukey Multiple Comparison test") (FIG. 11B). Treatment stopped after finished week 6 treatment, and tumor volume assessments were continued for all survival mice until week 16. Mice survival were also tracked by Kaplan-Meier survival curves until the study ended at week 16.

Figure 12A:
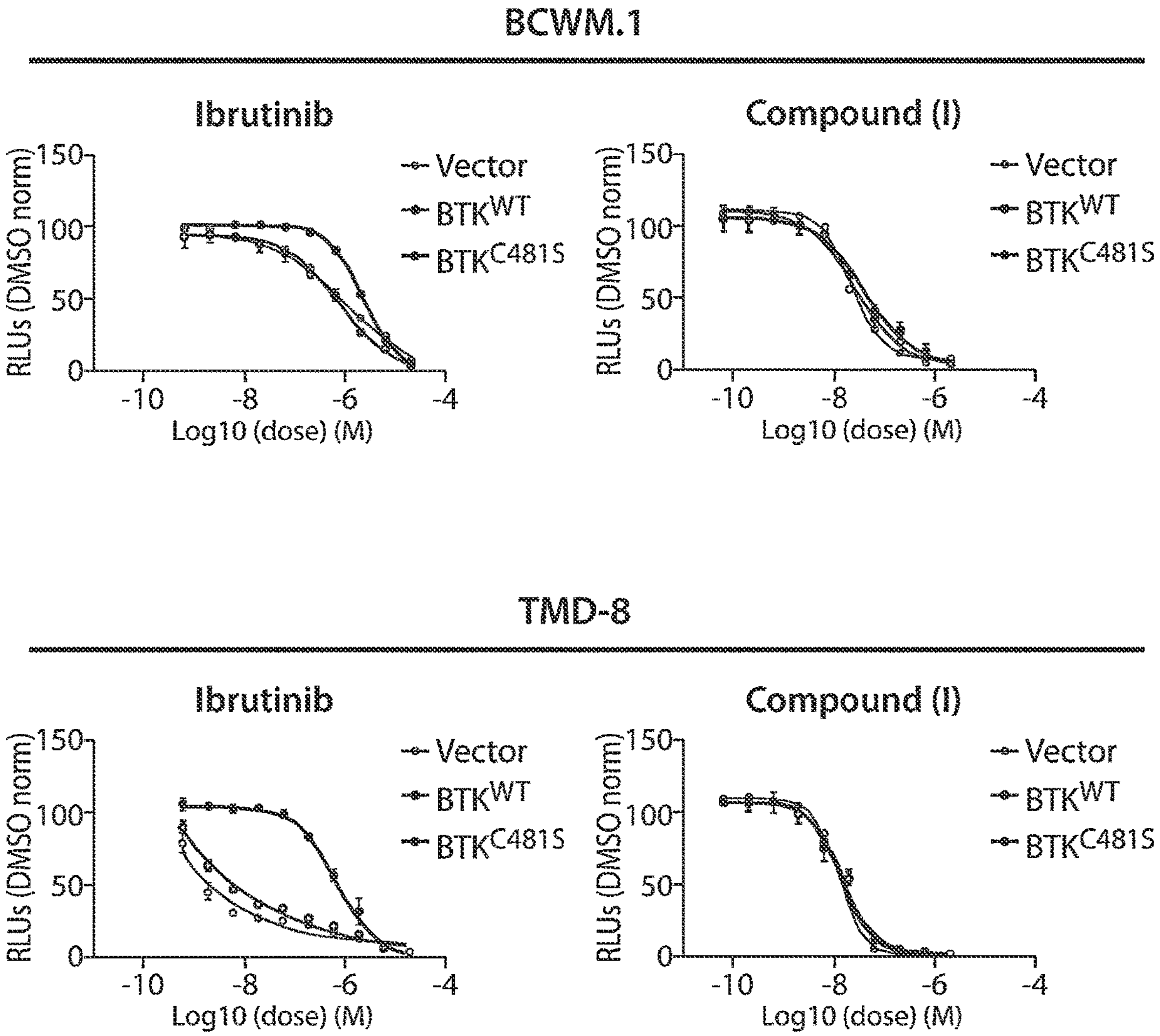
FIG. 12 shows in vitro cellular efficacies (drug dose-response) of ibrutinib or Compound (I). Drug dose-responses were measured by CellTiter-Glo™, a luminescent cell viability assay based on ATP detection, to indicate cell viability in vector only, $BTK^{WT}$ or $BTK^{C481S}$ expressing lentiviral vector transduced TMD8 ABC-DLBCL or BCWM.1 WM cells (FIG. 12A). Apoptosis analysis we measured by flow cytometry with Annexin-V/PI staining, the percentage of apoptotic cells are labeled (FIG. 12B).
Figure 12B:
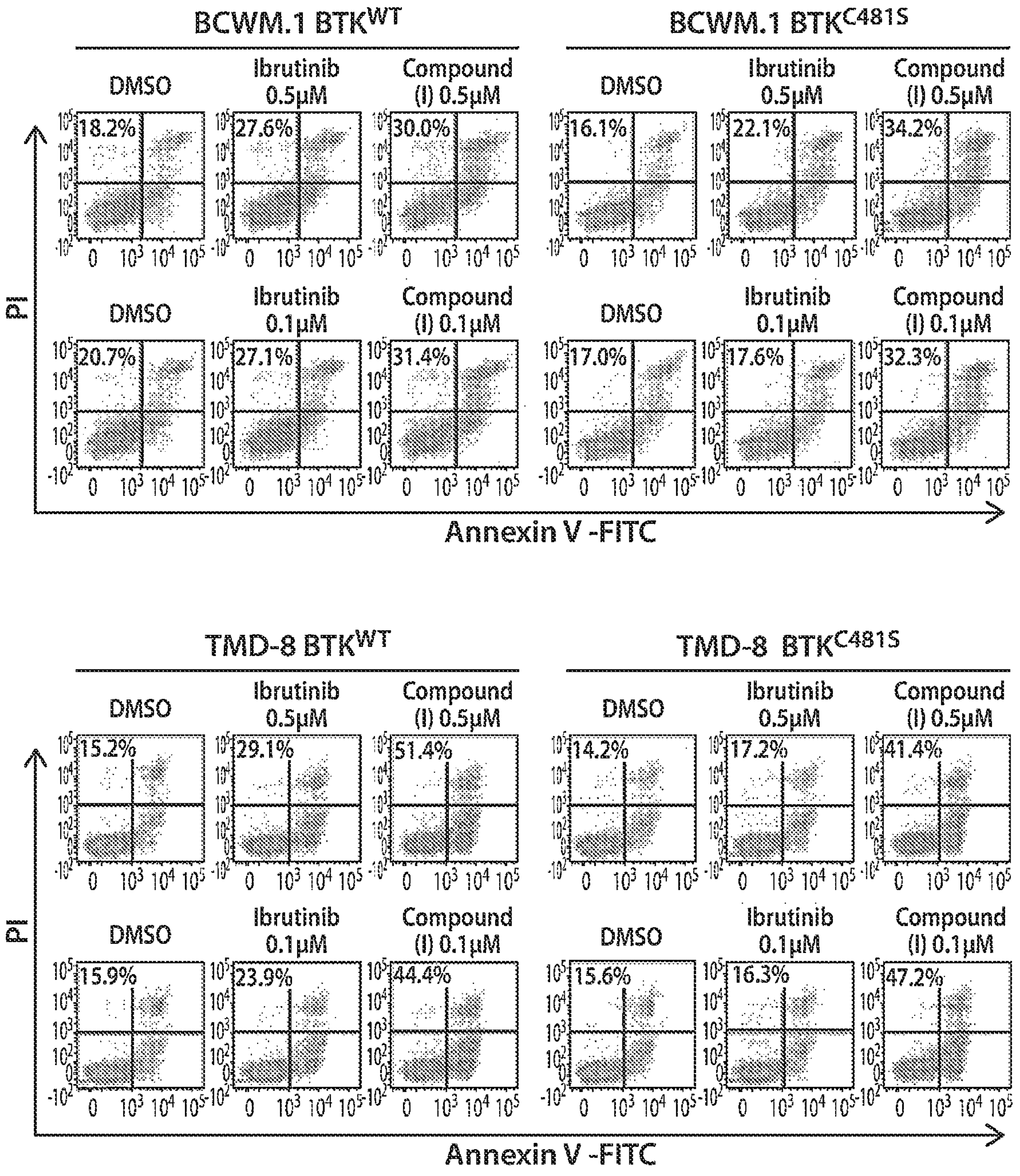

Example 7. Compound (I) Overcomes Ibrutinib Resistance Caused by the $BTK^{C481S}$ Mutation In Vitro in BCWM.1WM and TMD8 ABC DLBCL Cell Models FIG. 12 shows drug dose-responses were measured by CellTiter-Glo™, a luminescent cell viability assay based on ATP detection, to indicate cell viability in vector only, $BTK^{WT}$ or $BTK^{C481S}$ expressing lentiviral vector transduced TMD8 ABC-DLBCL or BCWM.1 WM cells. Unlike ibrutinib that shows resistance by the $BTK^{C481S}$ mutant, Compound (I) produces similar cellular efficacies in vector only, BTKWT or $BTK^{C481S}$ expressing BCWM.1 and TMD8 cells. (FIG. 12A). Apoptosis analysis we measured by flow cytometry with Annexin-V/PI staining, the percentage of apoptotic cells are labeled. Compound (I) produces similar cellular efficacies in vector only, $BTK^{WT}$ or $BTK^{C481S}$ expressing BCWM.1 and TMD8 cells (FIG. 12B).

Figure 13A:
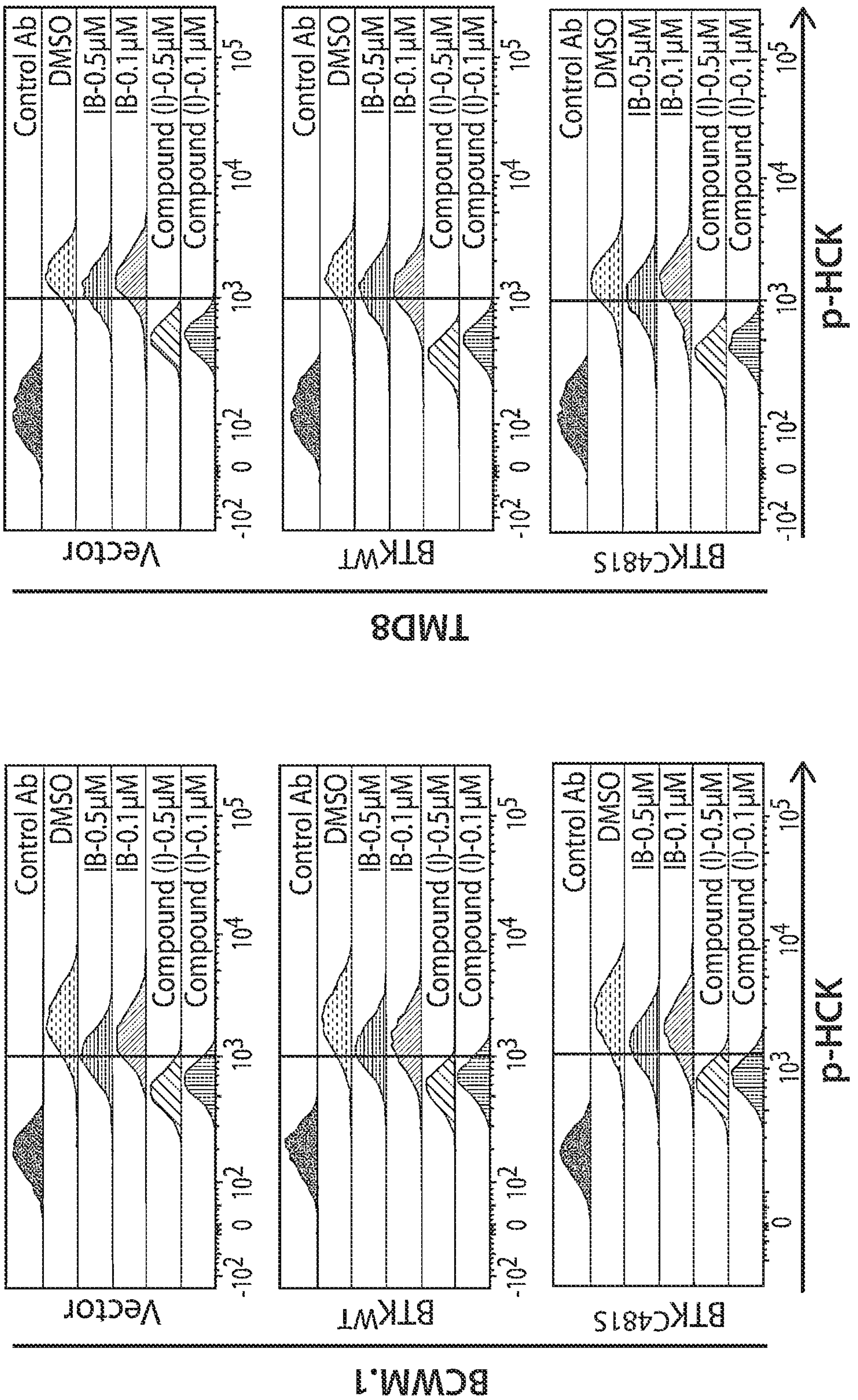
FIG. 13 shows compound (I) blocks HCK, BTK and downstream ERK1/2 activation in BTK Cys481 mutated BCWM.1 WM and TMD8 ABC DLBCL cell lines. Relative $pHCK^{Y411}$ levels resolved by PhosFlow™ (an intracellular stain for post-translationally modified signaling proteins) analysis following treatment with ibrutinib or Compound (I) at indicated concentrations for 1.0 hour in vector only, $BTK^{WT}$ or $BTK^{C481S}$ transduced BCWM.1 and TMD8 cells (FIG. 13A). $pBTK^{Y223}$ and $p\text{-}ERK1/2^{T202/Y204}$ expression by western blot analysis following treatment with ibrutinib or Compound (I) at indicated concentrations for 1.0 hour in vector only, $BTK^{WT}$ or $BTK^{C481S}$ transduced BCWM.1 and TMD8 cells. The expression levels of total BTK and ERK1/2 in these cells as well as protein loading control GAPDH are also shown (FIG. 13B).

Example 8. Compound (I) Blocks HCK, BTK and Downstream ERK1/2 Activation in Ibrutinib Resistant $BTK^{C481S}$ Mutated BCWM.1WM and TMD8 ABC DLBCL Cell Lines FIG. 13A shows PhosFlow™ (an intracellular stain for post-translationally modified signaling proteins) analysis of the impact of Compound (I) on HCK phosphorylation levels in BCWM.1 or TMD8 cells, TMD8 cells transduced with lentiviral vectors only, or ones that express $BTK^{WT}$ or $BTK^{C481S}$ mutant. Cells were treated with ibrutinib, A419259, or Compound (I) at the indicated concentrations for 1.0 hour and fixed with BD PhosFlow™ (an intracellular stain for post-translationally modified signaling proteins) Fix Buffer I (BD biosciences) for 10 minutes at 37° C., permeabilized with BD Perm/Wash™ Buffer I (a buffer intended to permeabilize cells and to serve as an antibody diluent and cell wash buffer, BD biosciences), then stained with rabbit anti-human p-HCK specific antibody (Abcam) followed by Donkey anti-Rabbit IgG (Alexa Fluor® 647, a bright, far-red-fluorescent dye) secondary antibody (Abcam). Compound (I) and A419259 effectively blocked HCK phosphorylation while ibrutinib modestly reduced the HCK phosphorylation in vector only, $BTK^{WT}$, or $BTK^{C481S}$ transduced BCWM.1 or TMD8 cells.

Figure 13B:
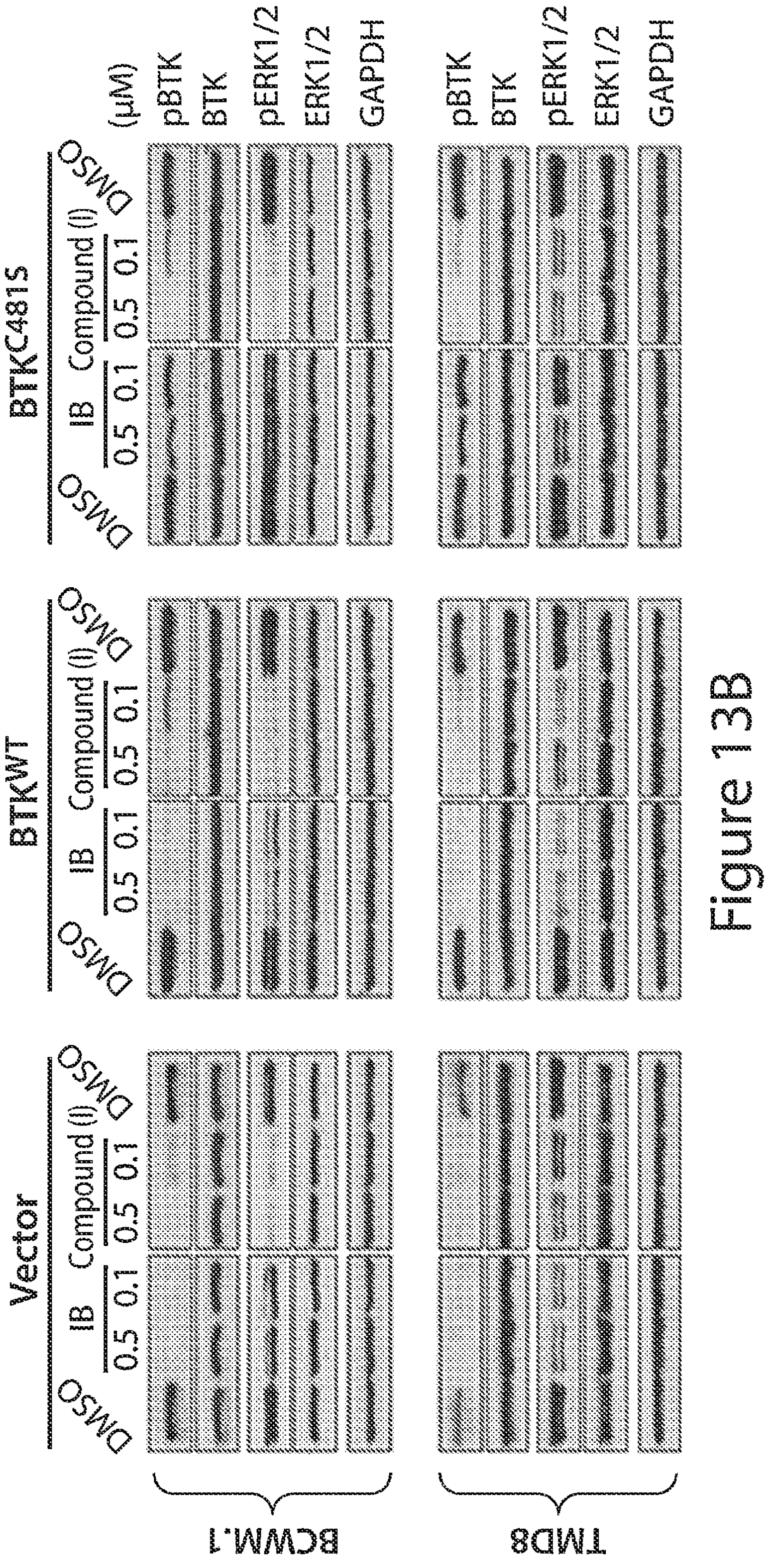

FIG. 13B shows western blotting of the impact of Compound (I) on BTK phosphorylation levels in BCWM.1 or TMD8 cells transduced with lentiviral vectors only, lentiviral vectors that express $BTK^{WT}$ or $BTK^{C481S}$ mutant. Cells were treated with ibrutinib, or Compound (I) at indicated concentrations for 1.0 hour and lysed with protein lysis buffer. Both Compound (I) and ibrutinib effectively blocked BTK and ERK 1/2 phosphorylation in vector only, and $BTK^{WT}$ transduced BCWM.1 or TMD8 cells. However, only Compound (I) potently blocked BTK and ERK 1/2 phosphorylation in $BTK^{C481S}$ transduced BCWM.1 or TMD8 cells, while ibrutinib did not.

Figure 14A:
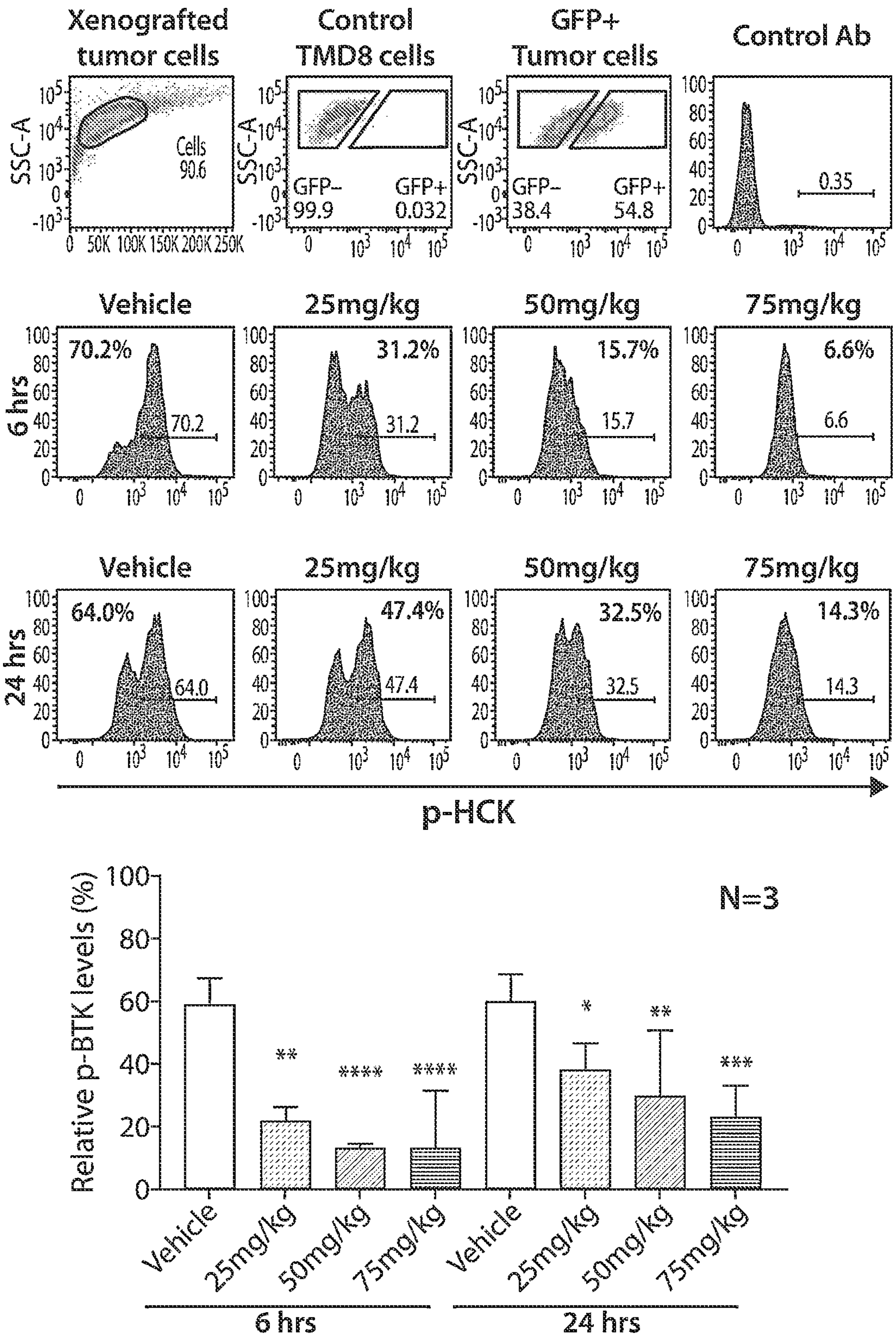
FIG. 14 shows pharmacodynamic studies showing the activity of HCK and BTK following oral administration of Compound (I) in NOD-SCID mice subcutaneously xenografted with ibrutinib resistant $BTK^{C481S}$ TMD8 ABC-DLBCL cells. PhosFlow™ (an intracellular stain for post-translationally modified signaling proteins) plots for $pHCK^{1411}$ (FIG. 14A) and $pBTK^{Y223}$ (FIG. 14B) in GFP+ TMD8 tumor cells excised at 6 and 24 hours following oral administration of Compound (I) at the indicated doses (n=3 per group). *p<0.05; p<0.01; *p<0.005; ****p<0.0001.
Figure 14B:
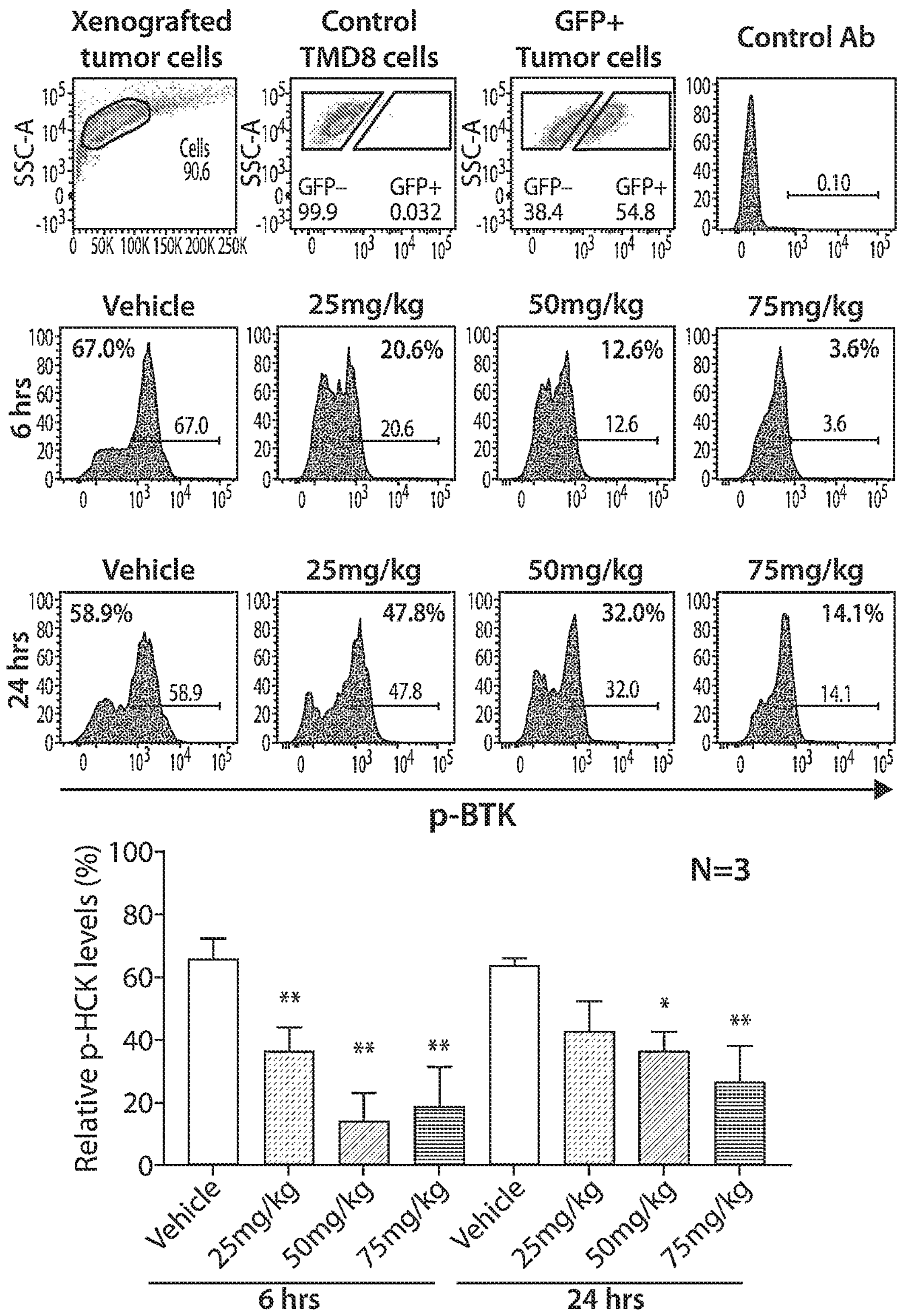

Example 9. Pharmacodynamic Studies Showing the Activity of HCK and BTK in NOD-SCID Mice Subcutaneously Xenografted with Ibrutinib Resistant $BTK^{C481S}$ TMD8 ABC-DLBCL Cells Ibrutinib resistant TMD8-$BTK^{C481S}$ tumor cells were implanted into NOD-SCID mice subcutaneously with 8 mice per cohort. After the tumors were established and reached to ~300 cubic millimeters, mice were treated p.o. on a once daily schedule with either vehicle control, ibrutinib, A419259, or Compound (I) at the concentration indicated. Tumors were measured twice a week with electronic calipers (FIG. 14). PhosFlow™ (an intracellular stain for post-translationally modified signaling proteins) plots for pHCKY411 (FIG. 14A) and pBTKY223 (FIG. 14B) in GFP+ TMD8 tumor cells excised at 6 and 24 hours following oral administration of Compound (I) at the indicated doses (n=3 per group). *p<0.05; p<0.01; *p<0.005; ****p<0.0001.

Figure 15A:
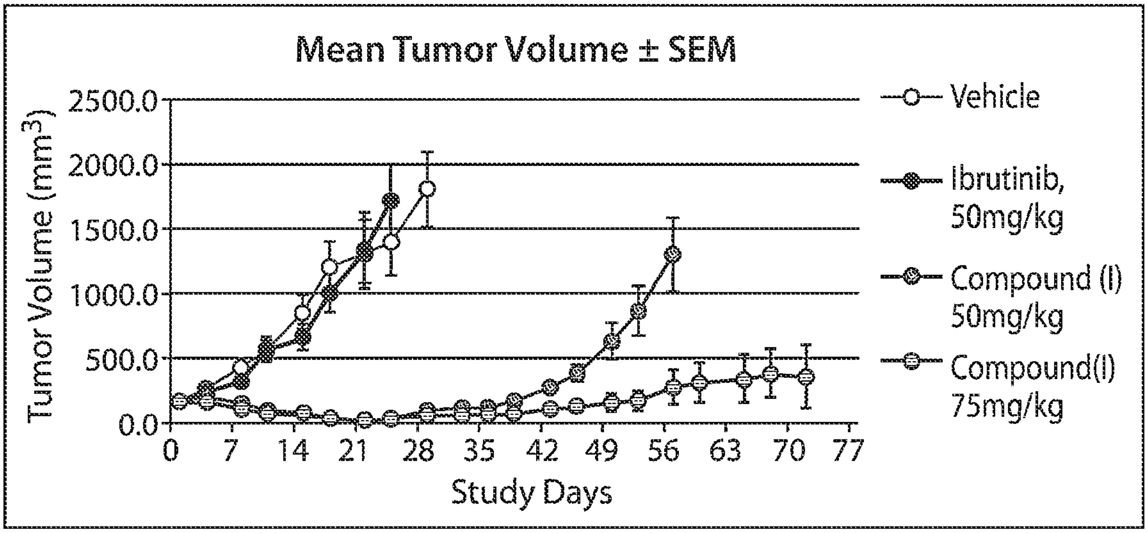
FIG. 15 sows the impact of Compound (I) on tumor volume and survival in ibrutinib resistant $BTK^{C481S}$ TMD8 ABC DLBCL xenograft mouse model. Efficacy studies in NOD-SCID mice (n=8 per cohort) bearing ibrutinib resistant $BTK^{C481S}$ expressing TMD8 cells following daily oral administration of vehicle control, ibrutinib (50 mg/kg) or Compound (I) (50 or 75 mg/kg). Tumor volume ($mm^3$) was measured twice weekly and reported as the mean volume ±SEM (FIG. 15A). Tumor volume comparisons at day 29. p-values for cohort comparisons are shown (FIG. 15B). Survival curve estimations using the Kaplan-Meier method. The median survival (days) for cohorts are shown using Prism software. P<0.0007 for Log-rank comparisons between cohorts (FIG. 15C).
Figure 15B:
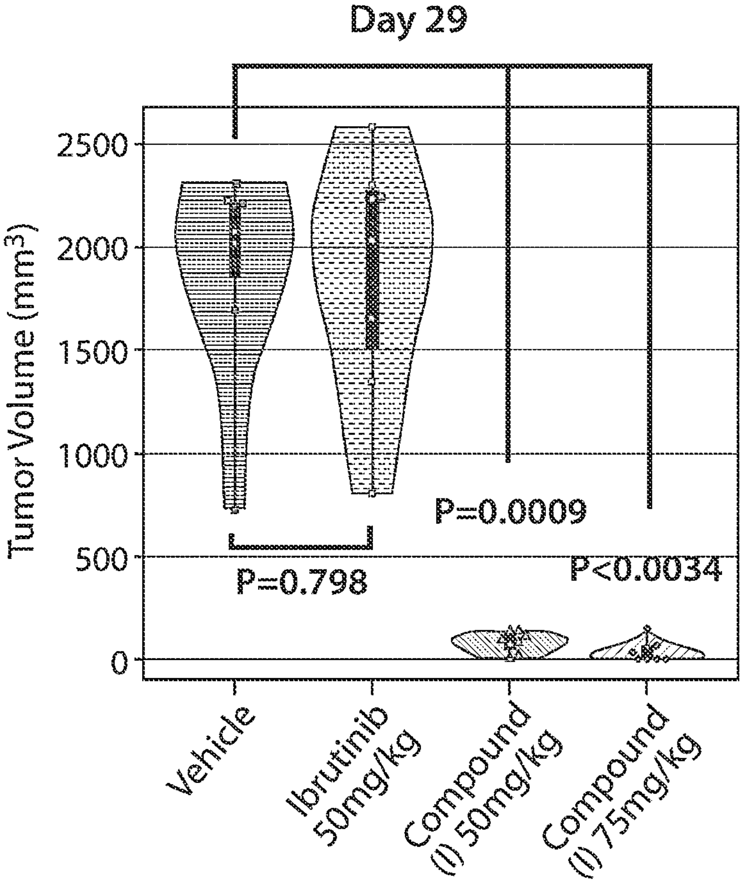
Figure 15C:
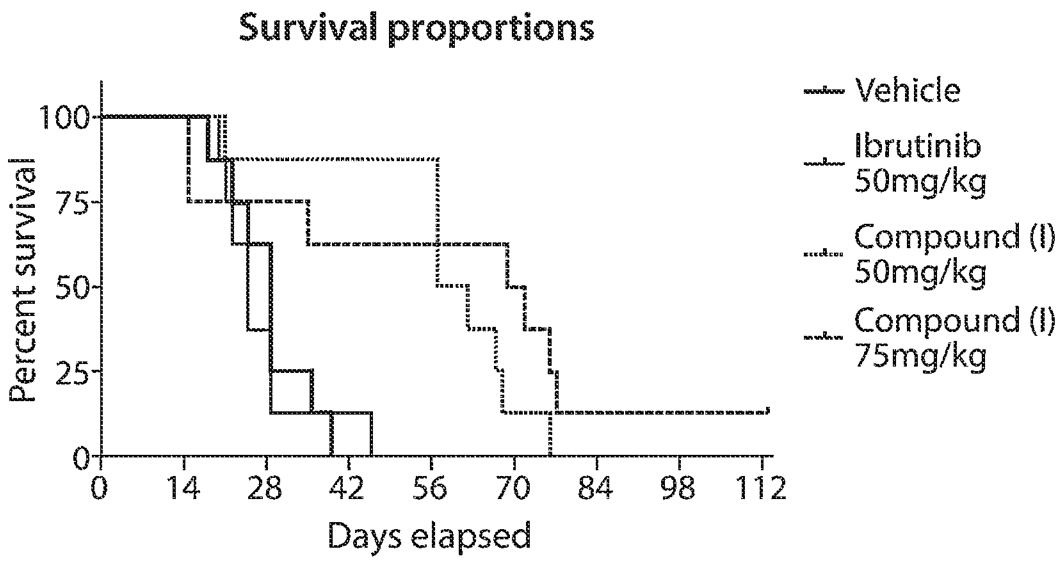

Example 10. Mean Tumor Volume Curves for Compound (I) in Ibrutinib Resistant TMD8-$BTK^{C481S}$ Xenograft Model Ibrutinib resistant TMD8-$BTK^{C481S}$ tumor cells were implanted into NOD-SCID mice subcutaneously with 8 mice per cohort. After tumors established and reached to ~200 cubic millimeter, mice were treated p.o. on a once daily schedule with either vehicle control or ibrutinib (50 mg/kg) or Compound (I) (50 mg/kg or 75 mg/kg). Efficacy studies in NOD-SCID mice (n=8 per cohort) bearing ibrutinib resistant $BTK^{C481S}$ expressing TMD8 cells following daily oral administration of vehicle control, ibrutinib (50 mg/kg) or Compound (I) (50 or 75 mg/kg). Tumor volume ($mm^3$) was measured twice weekly and reported as the mean volume ±SEM (FIG. 15A). Tumor volume comparisons at day 29. p-values for cohort comparisons are shown (FIG. 15B). Survival curve estimations using the Kaplan-Meier method. The median survival (days) for cohorts are shown using Prism software. P=0.0007 for Log-rank comparisons between cohorts (FIG. 15C).

Figure 16A:
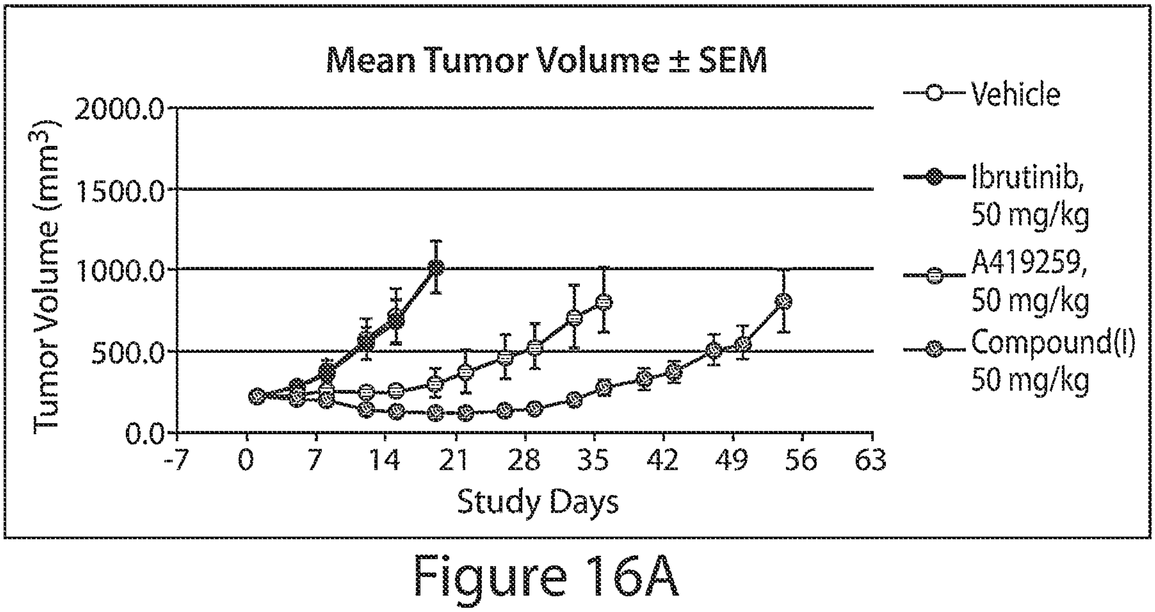
FIG. 16 shows the impact of Compound (I) on tumor volume and survival in ibrutinib resistant $BTK^{C481S}$ TMD8 ABC DLBCL xenograft mouse model. Efficacy studies in NOD-SCID mice (n=8 per cohort) bearing ibrutinib resistant $BTK^{C481S}$ expressing TMD8 cells following daily oral administration of vehicle control, ibrutinib (50 mg/kg), A419259 (50 mg/kg) or Compound (I) (50 mg/kg). Tumor volume ($mm^3$) was measured twice weekly and reported as the mean volume ±SEM (FIG. 16A). Tumor volume comparisons at day 33. p-values for cohort comparisons are shown (FIG. 16B). Survival curve estimations using the Kaplan-Meier method. The median survival (days) for cohorts are shown using Prism software. P<0.0001 for Log-rank comparisons between cohorts (FIG. 16C).
Figure 16B:
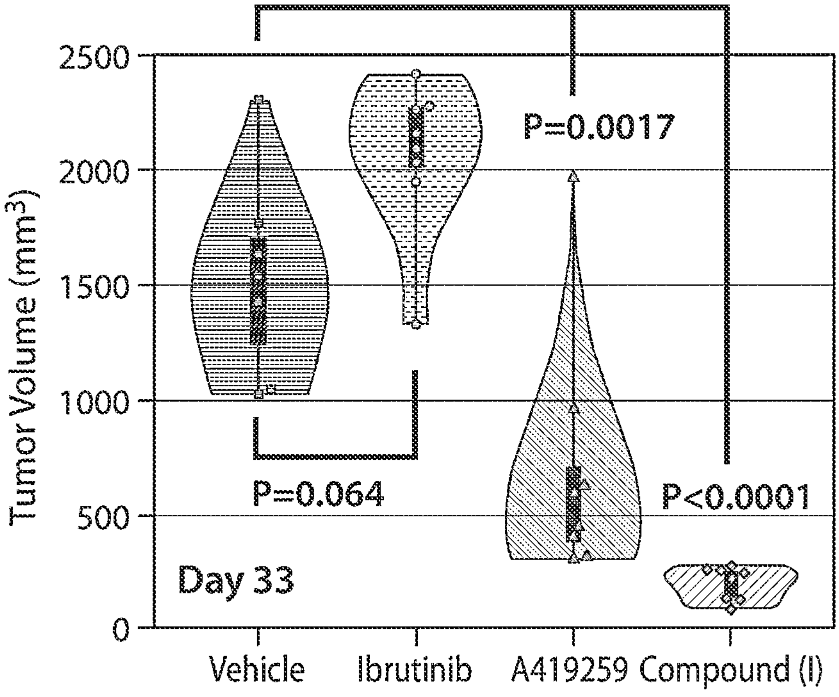
Figure 16C:
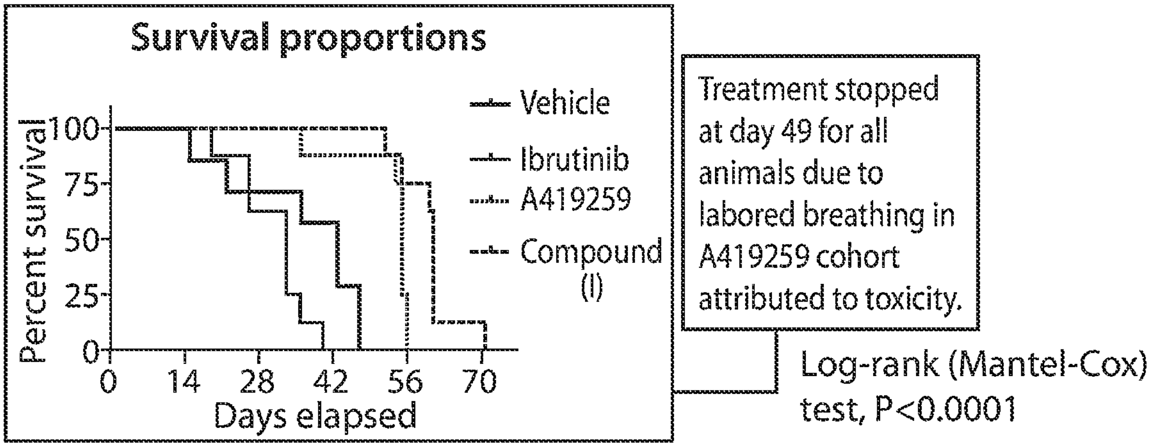

Efficacy studies in NOD-SCID mice (n=8 per cohort) bearing ibrutinib resistant $BTK^{C481S}$ expressing TMD8 cells following daily oral administration of vehicle control, ibrutinib (50 mg/kg), A419259 (50 mg/kg) or Compound (I) (50 mg/kg). Tumor volume ($mm^3$) was measured twice weekly and reported as the mean volume ±SEM (FIG. 16A). Tumor volume comparisons at day 33. p-values for cohort comparisons are shown (FIG. 16B). Survival curve estimations using the Kaplan-Meier method. The median survival (days)

for cohorts are shown using Prism software. P<0.0001 for Log-rank comparisons between cohorts (FIG. 16C).

Figure 17:
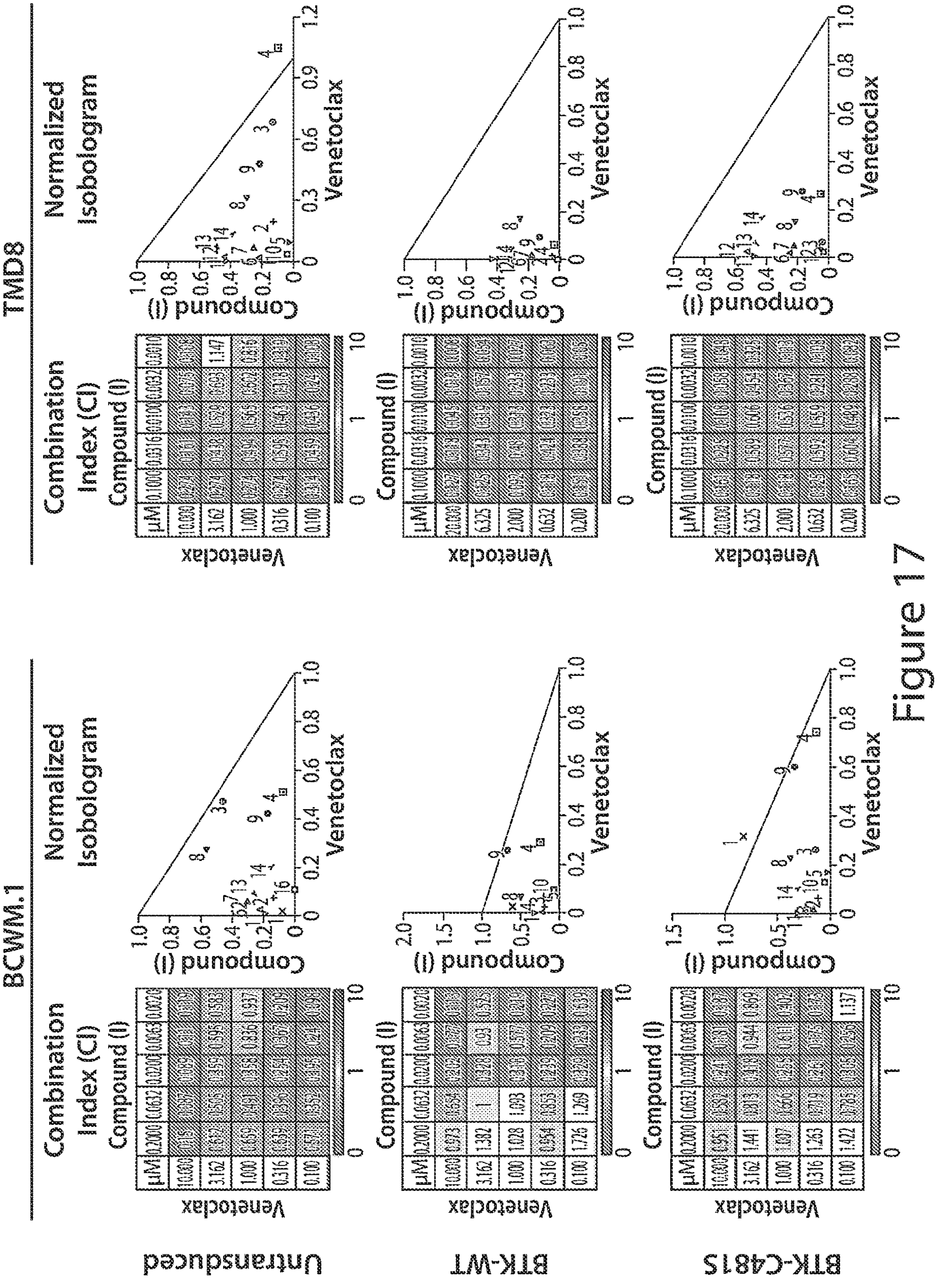
FIG. 17 shows in vitro studies assessed for synergistic interactions of Compound (I) and venetoclax in native (un-transduced), $BTK^{WT}$ and $BTK^{C481S}$ expressing MYD88 mutated BCWM.1 WM and TMD8 ABC DLBCL cells. The combination index (CI) and normalized isobologram analyses are depicted. CI<1 (indicated in shades of red) or the dots under the oblique line in the isobologram plots indicate a synergistic effect for the combination.

Example 11. Combination Index (CI) of Compound (I) and Venetoclax (a BCL-2 Inhibitor) in MYD88 Mutated Waldenstrom's Macroglobulinemia (BCWM.1) Cells In vitro studies assessed for synergistic interactions of Compound (I) and venetoclax in native (un-transduced), BTKWT and $BTK^{C481S}$ expressing MYD88 mutated BCWM.1 WM and TMD8 ABC DLBCL cells. The combination index (CI) and normalized isobologram analyses are depicted. CI<1 (indicated in shades of red) or the dots under the oblique line in the isobologram plots indicate a synergistic effect for the combination (FIG. 17).

Figure 18A:
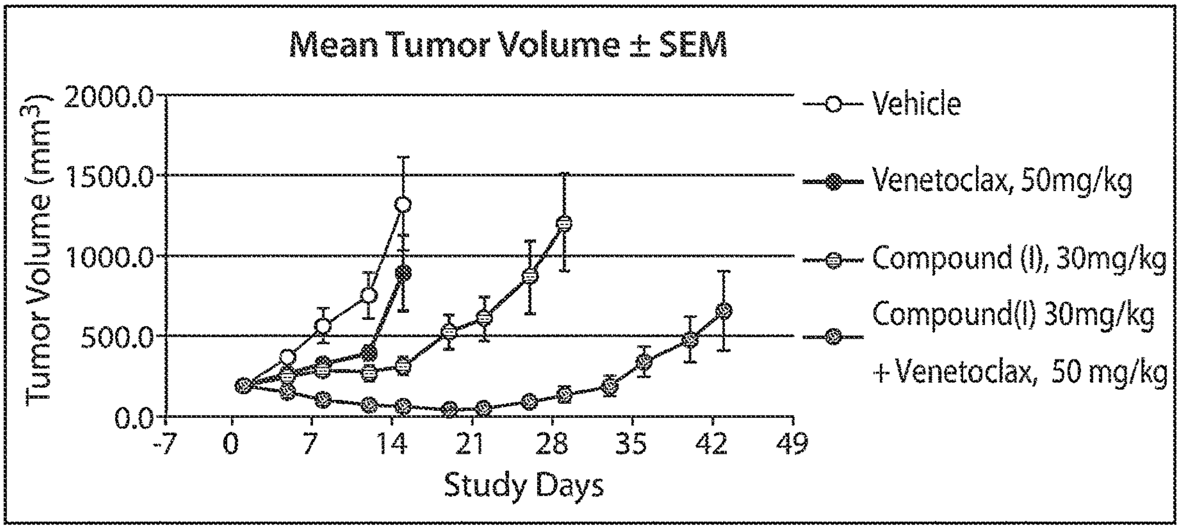
FIG. 18 shows the combination of Compound (I) and Venetoclax on tumor volume and survival in ibrutinib resistant $BTK^{C481S}$ TMD8 ABC DLBCL xenograft mouse model. Efficacy studies in NOD-SCID mice (n=8 per cohort) bearing ibrutinib resistant $BTK^{C481S}$ expressing TMD8 cells following daily oral administration of vehicle control, venetoclax (50 mg/kg), Compound (I) (30 mg/kg), or the combination of venetoclax (50 mg/kg) and Compound (I) (30 mg/kg). Tumor volume ($mm^3$) was measured twice weekly and reported as the mean volume ±SEM (FIG. 18A). Tumor volume comparisons at day 22. p-values for cohort comparisons are shown (FIG. 18B). Survival curve estimations using the Kaplan-Meier method. The median survival (days) for cohorts are shown using Prism software. P=0.0020 for Log-rank comparisons between cohorts (FIG. 18C).
Figure 18B:
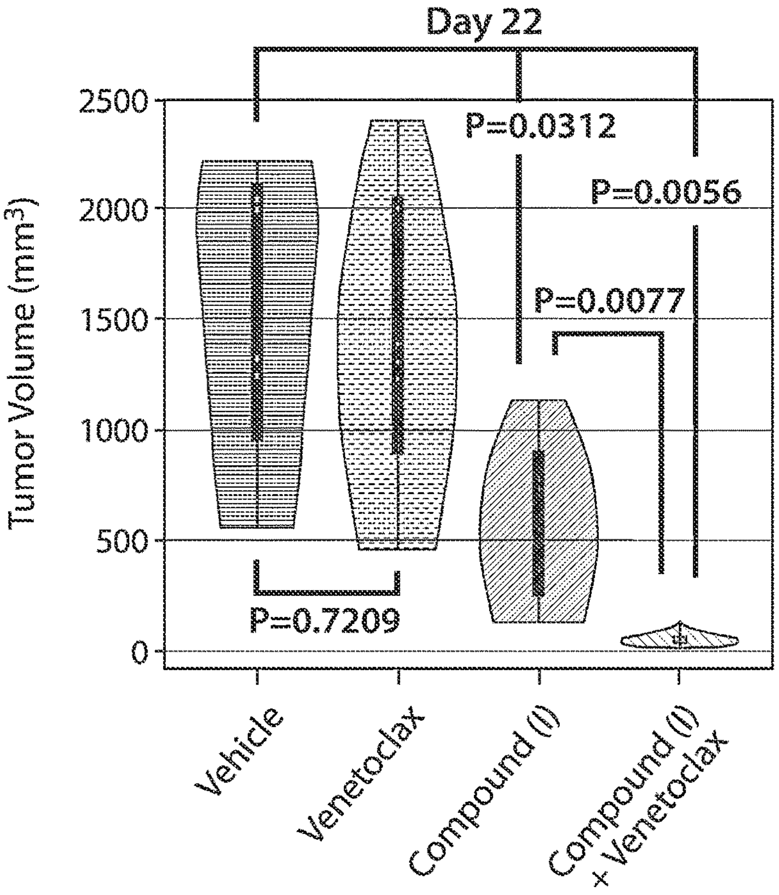
Figure 18C:
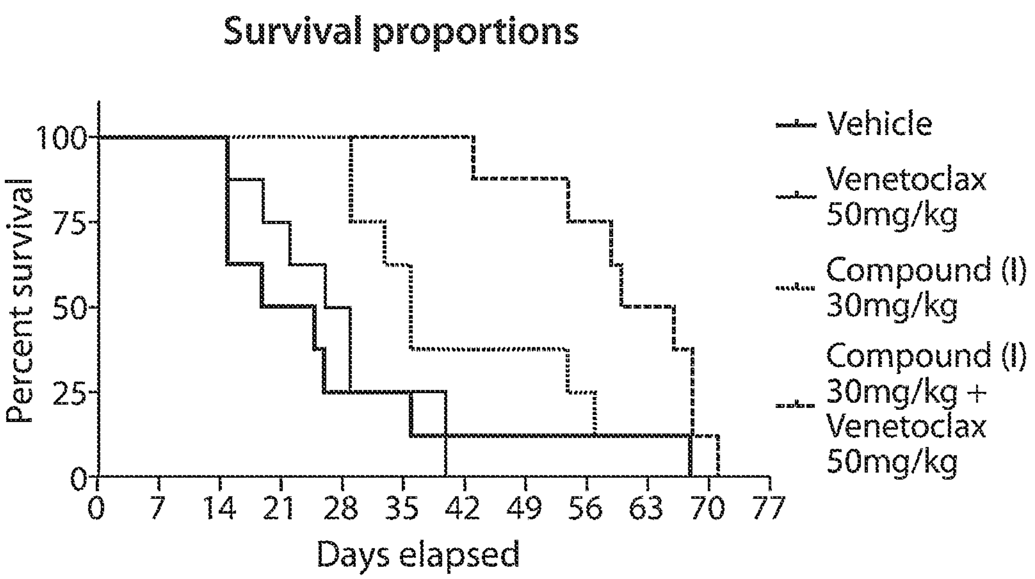

Example 12. Combination Index (CI) of Compound (I) and Venetoclax (a BCL-2 Inhibitor) in Untransduced Native MYD88 Mutated Waldenstrom's Macroglobulinemia (BCWM.1) and ABC DLBCL (TMD8) cells, and in $BTK^{WT}$ or $BTK^{C481S}$ transduced BCWM.1 or TMD8 cells FIG. 18 shows the combination of Compound (I) and Venetoclax on tumor volume and survival in ibrutinib resistant $BTK^{C481S}$ TMD8 ABC DLBCL xenograft mouse model. Efficacy studies in NOD-SCID mice (n=8 per cohort) bearing ibrutinib resistant $BTK^{C481S}$ expressing TMD8 cells following daily oral administration of vehicle control, venetoclax (50 mg/kg), Compound (I) (30 mg/kg), or the combination of venetoclax (50 mg/kg) and Compound (I) (30 mg/kg). Tumor volume ($mm^3$) was measured twice weekly and reported as the mean volume ±SEM (FIG. 18A). Tumor volume comparisons at day 22. p-values for cohort comparisons are shown (FIG. 18B). Survival curve estimations using the Kaplan-Meier method. The median survival (days) for cohorts are shown using Prism software. P=0.0020 for Log-rank comparisons between cohorts (FIG. 18C).

As demonstrated above, the combination of Compound (I) and venetoclax produces synthetic lethality in MYD88 mutated lymphoma cells.

Example 13. HCK Activation Status in Chronic Lymphocytic Leukemia Patients

Figure 19:
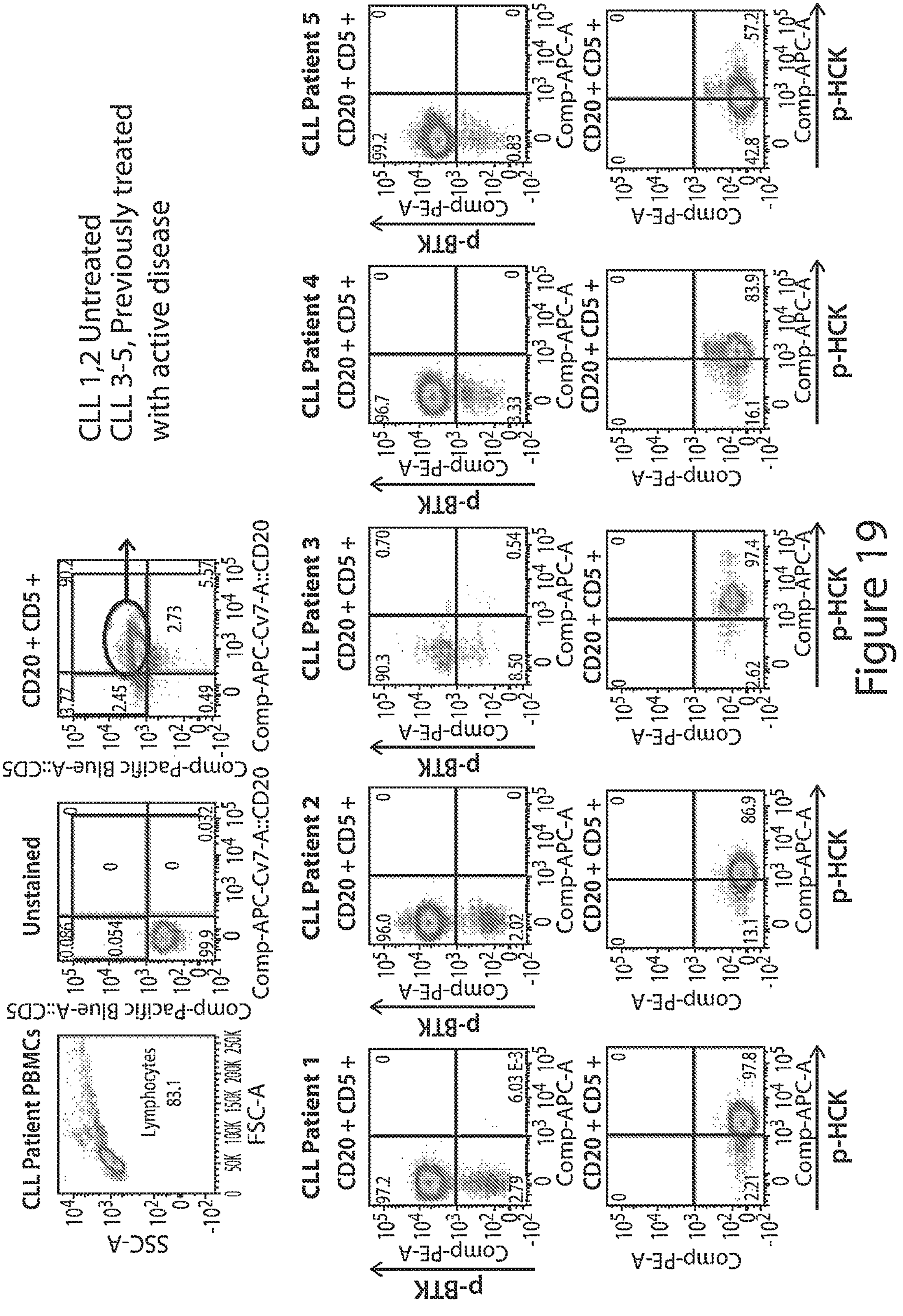
FIG. 19 shows HCK activation status in CLL patients was evaluated in primary tumor cells from peripheral blood mononuclear cells (PBMCs) of previously treated or untreated patients.

FIG. 19 shows HCK activation status in CLL patients was evaluated in primary tumor cells from peripheral blood mononuclear cells (PBMCs) of previously treated or untreated patients. PBMCs were isolated by Ficoll-Paque and fixed with BD PhosFlow™ Fix Buffer I (a buffer for simultaneous fixation and permeabilization of cells prior to intracellular staining, BD biosciences) for 10 minutes at 37° C., permeabilized with BD Perm/Wash™ Buffer I (a buffer for the intracellular staining of post-translationally modified signaling proteins, BD biosciences), then stained with mouse anti-human CD20 (APC-cy7) and CD5 (BV421) specific antibodies (BD biosciences) together with rabbit anti-human p-HCK specific antibody followed by Donkey anti-Rabbit IgG (Alexa Fluor® 647, a bright, far-red-fluorescent dye) secondary antibody, or PE labeled p-BTK antibody. p-HCK or p-BTK levels were analyzed on $CD20^+$ $CD5^+$ population.

Example 14. In Vitro Studies of Peripheral Blood Mononuclear Cells Isolated from Ibrutinib Relapsed CLL Patients Using Ibrutinib or Compound (I)

Figure 20:
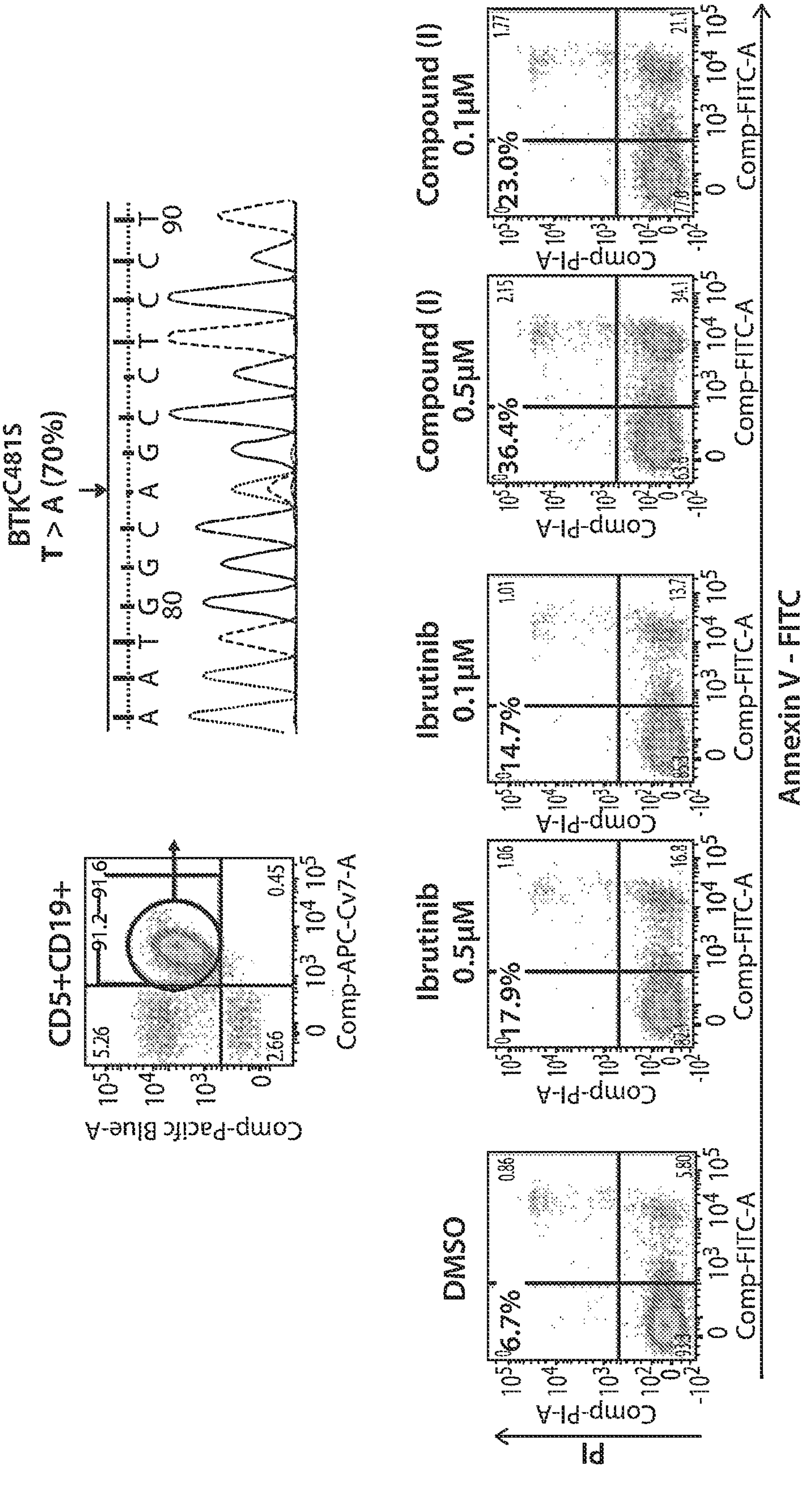
FIG. 20 shows an Annexin V—PI (Propidium iodide) assay of freshly isolated tumor cells that carry $BTK^{C481S}$ mutations in peripheral blood mononuclear cells (PBMCs) from an ibrutinib relapsed CLL patient that were treated with either ibrutinib or Compound (I).

FIG. 20 shows PBMCs from an ibrutinib relapsed CLL patients were isolated by Ficoll-Paque, and $CD19^+$ cells were isolated by magnetic beads, and genotyped by Sanger sequencing for $BTK^{C481S}$ mutations. Later genotype results indicated this patient carry $BTK^{C481S}$ mutation (T>A) in about 70% $CD19^+$ cells.

Fresh isolated PBMCs were treated with either ibrutinib or Compound (I) in cell culture media supplemented with 10% FBS for overnight. Following drug treatment, PBMCs were stained by Annexin V-FITC and PI together with mouse anti-human CD19 (APC-cy7) and CD5 (BV421) specific antibodies (BD biosciences). Apoptotic cells were measured by flow cytometry on $CD19^+CD5^+$ population.

Figure 21:
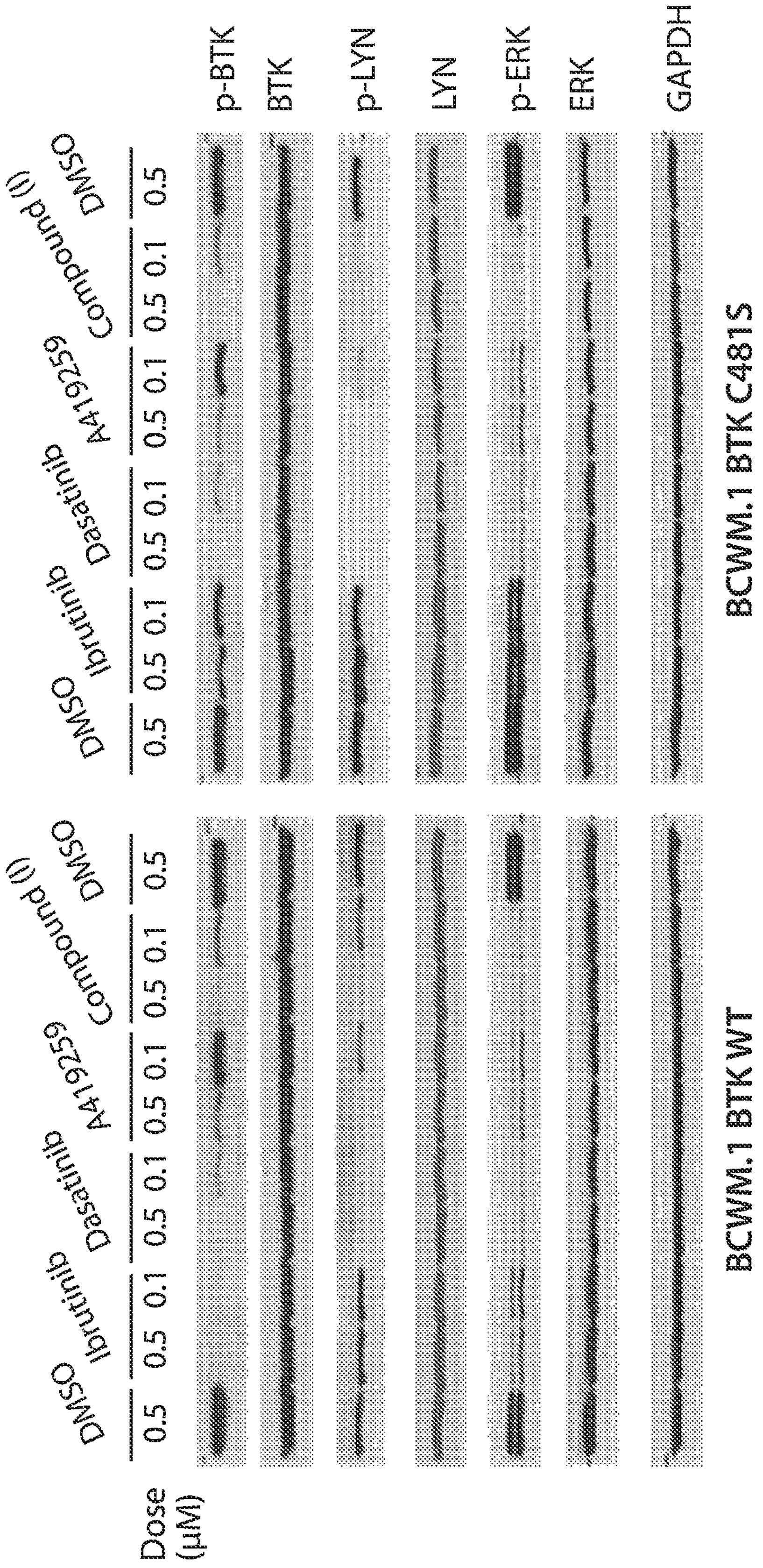
FIG. 21 shows western blot analysis on the phosphorylation levels of BTK, LYN and ERK1/ERK2 following 1 hour incubation with ibrutinib, Dasatinib, A419259 and Compound (I) in BTK wild type and $BTK^{C481S}$ mutant expressing BCWM.1 cells.

Example 15. Western Blot Analysis of BTK, LYN, ERK1, and ERK2 Following Treatment with Ibrutinib, Dasatinib, A419259, or Compound (I) in $BTK^{WT}$ or $BTK^{C481S}$ BCWM.1 Cells FIG. 21 shows western blot analysis on the phosphorylation levels of BTK, LYN and ERK1/2 following treatment with ibrutinib, Dasatinib, A419259, and Compound (I) at the indicated concentrations for 1 hour in $BTK^{WT}$ or $BTK^{C481S}$ transduced BCWM.1 cells. Total proteins for each kinase and GAPDH were used for protein expression and loading controls. Compound (I) effectively blocked BTK, LYN and ERK1/ERK2 phosphorylation in both $BTK^{WT}$ and $BTK^{C481S}$ mutant expressing BCWM.1 cells.

Example 16. Synthesis of Compound (I)

Compound (I) was synthesized according the scheme below.

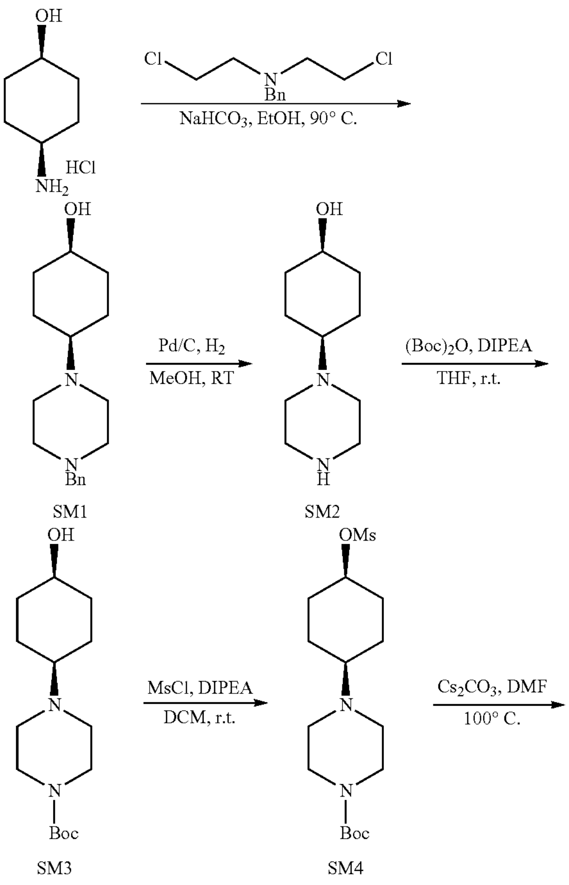

SM1 SM2 SM3 SM4

-continued

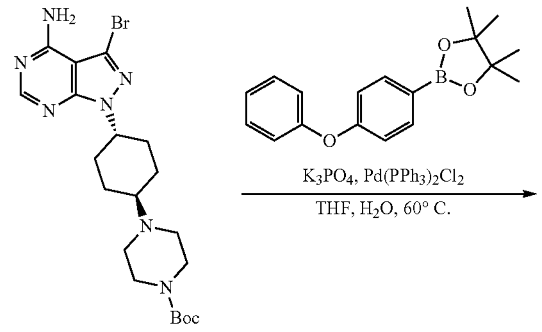

SM5

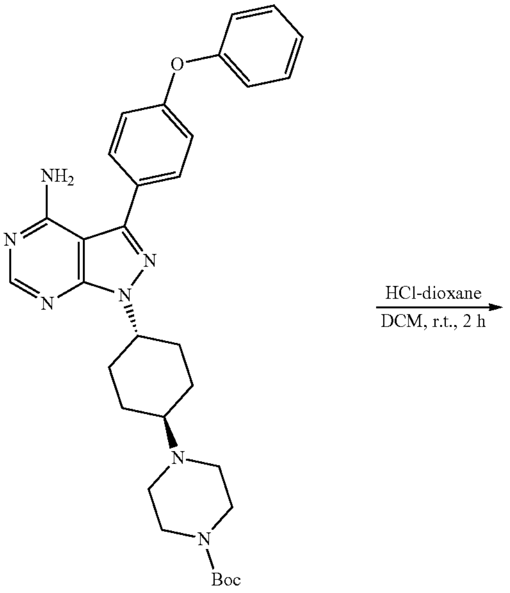

SM6

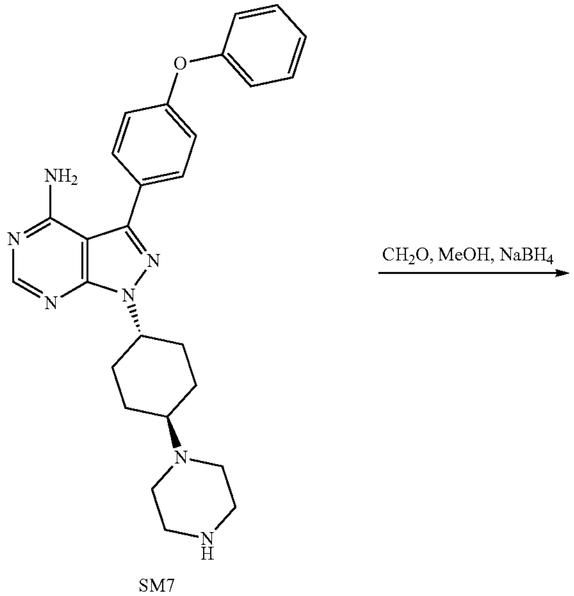

SM7

-continued

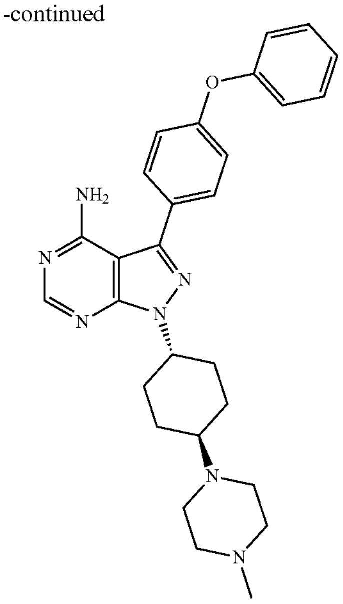

(I)

(1s,4s)-4-(4-benzylpiperazin-1-yl)cyclohexanol (SM1)

A mixture of cis-4-aminocyclohexanol hydrochloride (2.0 g, 17.3 mmol), N-benzyl-2-chloro-N-(2-chloroethyl) ethanamine (5.5 g, 20.76 mmol) and $NaHCO_3$ (5.7 g, 69.2 mmol) in EtOH (30 mL) was stirred at 90° C. for 5 hours. The mixture was then concentrated in vacuum, and the residue was diluted with water (100 mL) and extracted with ethyl acetate (150 mL×2). The combined organic phase was then washed with brine (50 mL×2), dried over anhydrous $Na_2SO_4$, concentrated, and purified by column chromatography on silica-gel (DCM/MeOH=10/1) to obtain SM1 as yellow oil (2.8 g, yield 57%). LCMS (m/z): 275.2 $[M+H]^+$.

(1s,4s)-4-(piperazin-1-yl)cyclohexanol (SM2)

A mixture of SM1 (2.7 g, 9.85 mmol), $CH_3COOH$ (0.5 mL) and Pd/C (10%, 270 mg) in i-PrOH (20 mL) was stirred at room temperature under $H_2$ (1 atm) for 24 hours. After this time, the mixture was filtered, the filtrate was concentrated to leave crude SM2 as yellow oil (1.5 g, yield 83%). LCMS (m/z): 185.1 $[M+H]^+$.

tert-butyl 4-((1s, 4s)-4-hydroxycyclohexyl)piperazine-1-carboxylate (SM3)

A mixture of SM2 (1.5 g, 8.1 mmol), $(Boc)_2O$ (4.0 mL, 16.2 mmol) and DIPEA (4.0 mL) in THF (20 mL) was stirred at room temperature for 2 hours. After this time, the mixture was concentrated to leave crude SM3 as brown oil (2.5 g, yield 80%). LCMS (m/z): 285.2 $[M+H]^+$.

tert-butyl 4-((1s, 4s)-4-(methylsulfonyloxy)cyclohexyl)piperazine-1-carboxylate (SM4)

To a mixture of SM3 (2.5 g, 8.1 mmol) and DIPEA (4.0 mL) in DCM (20 mL) was added dropwise MsCl (1.0 mL) at 0° C. The mixture was then stirred at room temperature for 4 hours and concentrated to remove the solvent, and the residue was diluted with water (100 mL) and extracted with ethyl acetate (150 mL×2). The combined organic extract was then washed with brine (50 mL×2), dried over anhydrous $Na_2SO_4$, filtered, and concentrated to leave crude SM4 as brown oil (600 mg, yield 20%). LCMS (m/z): 363.0 $[M+H]^+$.

tert-butyl 4-((1r, 4r)-4-(4-amino-3-bromo-1H-pyrazolo[3,4-d]pyrimidin-1-yl)cyclohexyl)piperazine-1-carboxylate (SM5)

A mixture of 3-bromo-1H-pyrazolo[3,4-d]pyrimidin-4-amine (353 mg, 1.65 mmol), SM4 (600 mg, 1.65 mmol), and $Cs_2CO_3$ (1.0 g, 3.3 mmol) in DMF (15 mL) was stirred at 100° C. for 16 hours. After this time, the reaction mixture was cooled down to room temperature, diluted with brine (100 mL), and extracted with ethyl acetate (50 mL×2). The combined organic extract was dried over anhydrous $Na_2SO_4$, filtered, concentrated and purified by column chromatography on silica-gel (DCM/MeOH=10/1) to obtain SM5 as yellow solid (300 mg, yield 38%). LCMS (m/z): 480.0 $[M+H]^+$. tert-butyl 4-((1r, 4r)-4-(4-amino-3-(4-phenoxyphenyl)-1H-pyrazolo[3,4-d]pyrimidin-1-yl)cyclohexyl)piperazine-1-carboxylate (SM6)

A mixture of SM5 (60 mg, 0.12 mmol), 4,4,5,5-tetramethyl-2-(4-phenoxyphenyl)-1,3,2-dioxaborolane (56 mg, 0.18 mmol), $Pd(PPh_3)_2Cl_2$ (9.0 mg, 0.012 mmol), and $K_3PO_4$ (51 mg, 0.24 mmol) in THE (2.0 mL) and $H_2O$ (0.5 mL) was stirred at 60° C. for 16 hours. After this time, the mixture was filtered, and the filtrate was diluted with brine (50 mL) and extracted with ethyl acetate (50 mL×2). The combined organic extracts were then dried over anhydrous $Na_2SO_4$, filtered, concentrated and purified by column chromatography on silica-gel (DCM/MeOH=10/1) to obtain SM6 as brown oil (40 mg, yield 58%). LCMS (m/z): 570.4 $[M+H]^+$.

3-(4-phenoxyphenyl)-1-((1r, 4r)-4-(piperazin-1-yl)cyclohexyl)-1H-pyrazolo[3,4-d]pyrimidin-4-amine (SM7)

To a solution of SM6 (40 mg, 0.07 mmol) in DCM (5.0 mL) was added HCl solution in 1,4-dioxane (4M, 2.0 mL), the mixture was stirred at room temperature for 2 hours. After this time, the reaction mixture was concentrated in vacuum, and the residue was diluted with DCM (30 mL). The pH was adjusted to pH 8 with saturated $Na_2CO_3$ solution and filtered, the filtrate was concentrated and purified by preparative HPLC (C18 column, $CH_3CN/H_2O$, containing 0.05% TFA) to give SM7 as white solid (15.2 mg, yield 47.5%). LCMS (m/z): 470.1 $[M+H]^+$; 1H NMR (400 MHz, DMSO-d6): δ 8.23 (s, 1H), 7.64 (d, J=8.8 Hz, 2H), 7.45-7.41 (m, 2H), 7.20-7.11 (m, 5H), 4.64-4.63 (m, 1H), 2.85-2.81 (m, 4H), 2.57 (s, 2H), 2.49-2.39 (m, 2H), 2.04-1.90 (m, 6H), 1.50-1.47 (m, 2H).

1-((1r,4r)-4-(4-methylpiperazin-1-yl)cyclohexyl)-3-(4-phenoxyphenyl)-1H-pyrazolo[3,4-d]pyrimidin-4-amine (I)

A mixture of SM7 (400 mg, 0.85 mmol), $(CH_2O)_n$(76 mg, 0.85 mmol), and $CH_3COOH$ (0.5 mL) in MeOH (10.0 mL) was stirred at room temperature for 3 hours, and then $NaBH_4$ (97 mg, 2.55 mmol) was added, the mixture was stirred at room temperature for 16 hours and concentrated in vacuum, the residue was diluted with brine (100 mL) and extracted with ethyl acetate (150 mL×2), the combined organic was dried over anhydrous $Na_2SO_4$, filtered, concentrated and purified by preparative HPLC to afford Compound (I) as white solid (150 mg, yield 36%). LCMS (m/z): 484.1 $[M+H]^+$; $^1$H-NMR (400 MHz, DMSO-$d_6$): δ 8.23 (s, 1H), 7.64 (d, J=8.8 Hz, 2H), 7.43 (t, J=8.0 Hz, 2H), 7.20-7.11 (m, 5H), 4.63 (m, 1H), 2.52 (m, 3H), 2.37-2.30 (m, 6H), 2.13 (s, 3H), 2.03-1.91 (m, 6H), 1.47-1.43 (m, 2H).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein.

The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method of treating one or more of Waldenstrom's macroglobulinemia (WM) and activated B-cell-like diffuse large B-cell lymphoma (ABC-DLBCL), wherein either one or more of the WM and ABC-DLBCL is associated with a mutation in a MYD88 protein, comprising administering to the subject in need thereof, a Compound (I) of the formula:

(I)

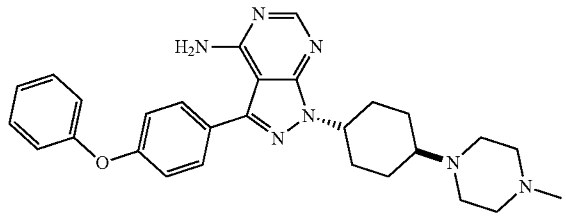

or a pharmaceutically acceptable salt thereof, and wherein the administration effectively inhibits each of:

a) a hematopoietic cell kinase (HCK); and b) a Bruton's tyrosine kinase (BTK), at a similar level.

2. The method of claim 1, wherein the HCK is a mutated HCK.

3. The method of claim 1, wherein the administration of the Compound (I) further effectively inhibits a LYN proto-oncogene tyrosine kinase (LYN).

4. The method of claim 1, wherein the BTK is a mutated BTK.

5. The method of claim 1, wherein the BTK is mutated at Cys481.

6. The method of claim 1, wherein the BTK is a C481S mutated BTK.

7. The method of claim 1, wherein the subject is resistant to treatment with a BTK inhibitor.

8. The method of claim 7, wherein the BTK inhibitor is ibrutinib, CC-292, ONO-4059, evobrutinib, spebrutinib, BGB-3111, HM71224, or ACP-196, or a pharmaceutically acceptable salt, solvate, hydrate, polymorph, co-crystal, isotopically-labeled derivative, or stereoisomer thereof.

9. The method of claim 1, wherein the subject is a mammal.

10. The method of claim 1, wherein the subject is a human.

11. The method of claim 1, wherein the subject has previously undergone treatment with a BTK inhibitor.

12. The method of claim 1, wherein the administration of the Compound (I) inhibits the activity of each of the HCK and the BTK by at least 1%.

13. The method of claim 12, wherein the administration of the Compound (I) inhibits the activity of each of the HCK and the BTK by at least 10%.

14. The method of claim 1, wherein the administration has nanomolar activity against each of: a) a hematopoietic cell kinase (HCK); and b) a Bruton's tyrosine kinase (BTK).

15. The method of claim 1, wherein the administration inhibits each of: a) a hematopoietic cell kinase (HCK); and b) a Bruton's tyrosine kinase (BTK), with an $IC_{50}$ of less than about 1 nM.

16. A method of treating Waldenstrom's macroglobulinemia (WM) wherein the WM is associated with a mutation in a MYD88 protein, comprising administering to the subject in need thereof, a Compound (I) of the formula:

(I)

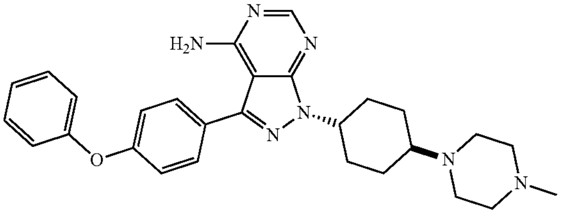

or a pharmaceutically acceptable salt thereof, wherein the administration of the Compound (I) effectively inhibits each of:

a) a hematopoietic cell kinase (HCK); and b) a Bruton's tyrosine kinase (BTK), at a similar level.

17. A method of treating activated B-cell-like diffuse large B-cell lymphoma (ABC-DLBCL) wherein the ABC-DLBCL is associated with a mutation in a MYD88 protein, comprising administering to the subject in need thereof, a Compound (I) of the formula:

(I)

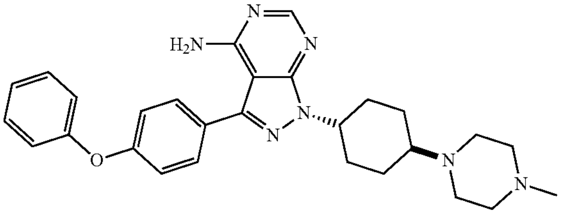

or a pharmaceutically acceptable salt thereof, wherein the administration of the Compound (I) effectively inhibits each of:

a) a hematopoietic cell kinase (HCK); and b) a Bruton's tyrosine kinase (BTK), at a similar level.

* * * * *